US009133515B2

(12) United States Patent
Giese et al.

(10) Patent No.: US 9,133,515 B2
(45) Date of Patent: Sep. 15, 2015

(54) USE OF VEGFR1 AS A BIOMARKER

(71) Applicant: SILENCE THERAPEUTICS AG, Berlin (DE)

(72) Inventors: Klaus Giese, Berlin (DE); Joerg Kaufmann, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 13/894,650

(22) Filed: May 15, 2013

(65) Prior Publication Data

US 2014/0179755 A1 Jun. 26, 2014

(30) Foreign Application Priority Data

May 16, 2012 (EP) .................................... 12003888

(51) Int. Cl.

| | |
|---|---|
| ***C12N 15/113*** | (2010.01) |
| ***C12Q 1/68*** | (2006.01) |
| ***G01N 33/574*** | (2006.01) |
| ***G01N 33/569*** | (2006.01) |

(52) U.S. Cl.

CPC ........ *C12Q 1/6881* (2013.01); *G01N 33/56966* (2013.01); *G01N 33/574* (2013.01); *C12N 15/1135* (2013.01); *C12N 2310/321* (2013.01); *C12N 2310/343* (2013.01); *G01N 2333/71* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 5,849,902 | A | 12/1998 | Arrow et al. |
| 5,989,912 | A | 11/1999 | Arrow et al. |
| 6,605,713 | B1 | 8/2003 | Fürste et al. |
| 8,168,776 | B2 | 5/2012 | Kreutzer et al. |

FOREIGN PATENT DOCUMENTS

| | | |
|---|---|---|
| EP | 0533838 | 6/1991 |
| WO | WO 98/08856 | 3/1998 |
| WO | WO 00/44895 | 8/2000 |
| WO | WO 01/75164 | 10/2001 |
| WO | WO 2004/019973 | 3/2004 |
| WO | WO 2008/009477 | 1/2008 |

OTHER PUBLICATIONS

Barleon, B. et al. "Soluble VEGFR-1 secreted by endothelial cells and monocytes is present in human serum and plasma from healthy donors" *Angiogenesis,* 2001, vol. 4, pp. 143-154.

Caine, G.J. et al. "Plasma angiopoietin-I, angiopoietin-2 and Tie-2 in breast and prostate cancer: a comparison with VEGF and Flt-I" *European Journal of Clinical Investigation,* 2003, vol. 33, pp. 883-890.

Doherty, E.A. et al. "Ribozyme Structures and Mechanisms" *Annual Review of Biophysics and Biomolecular Structure,* 2001, vol. 30, pp. 457-475.

Ellisen, L.W. et al. "Hereditary Breast Cancer" *Annual Review of Medicine,* 1998, vol. 49, pp. 425-436.

Fearon, E.R. et al. "A Genetic Model for Colorectal Tumorigenesis" *Cell,* Jun. 1, 1990, vol. 61, pp. 759-767.

Foulds, L. "The Natural History of Cancer" *Journal of Chronic Disease,* Jul. 1958, vol. 8, No. 1, pp. 2-37.

Lee, W.-H. et al. "Human Retinoblastoma Susceptibility Gene: Cloning, Identification, and Sequence" *Science,* Mar. 13, 1987, vol. 235, No. 4794, pp. 1394-1399.

Lewin, A.S. et al. "Ribozyme gene therapy: applications for molecular medicine" *Trends in Molecular Medicine,* May 2001, vol. 7, No. 5, pp. 221-228.

Oishi, K. et al. "Identification and Characterization of PKNβ, a Novel Isoform of Protein Kinase PKN: Expression and Arachidonic Acid Dependency Are Different from Those of PKNα" *Biochemical and Biophysical Research Communications,* 1999, vol. 261, No. 3, pp. 808-814.

Santel, A. et al. "A novel siRNA-lipoplex technology for RNA interference in the mouse vascular endothelium" *Gene Therapy,* 2006, vol. 13, pp. 1222-1234.

Shibata, H. et al. "PKNβ interacts with the SH3 Domains of Graf and a Novel Graf Related Protein, Graf2, Which are GTPase Activating Proteins for Rho Family" *Journal of Biochemistry*, 2001, vol. 130, No. 1., pp. 23-31.

Soifer, H.S. et al. "MicroRNAs in Disease and Potential Therapeutic Applications" *Molecular Therapy,* Dec. 12, 2007, vol. 15, No. 12, pp. 2070-2079.

Stenvang, J. et al. "MicroRNAs as targets for antisense-based therapeutics" *Expert Opin. Biol. Ther.,* 2008, vol. 8, No. 1, pp. 59-81.

Weinberg, R.A. "Oncogenes, Antioncogenes, and the Molecular Bases of Multistep Carcinogenesis" *Cancer Research,* 1989, vol. 49, pp. 3713-3721.

*Primary Examiner* — Tracy Vivlemore

(74) *Attorney, Agent, or Firm* — Saliwanchik, Lloyd & Eisenschenk

(57) ABSTRACT

The present invention is related to the use of VEGFR1 or of a nucleic acid coding for VEGFR1 as a biomarker in a method for the treatment of a subject, wherein the method for the treatment comprises administering to the subject a PKN3 inhibitor.

4 Claims, 29 Drawing Sheets

VEGFR1 biomarker in response to PKN3 knock down in PC-3 cells
PKN3 knock down
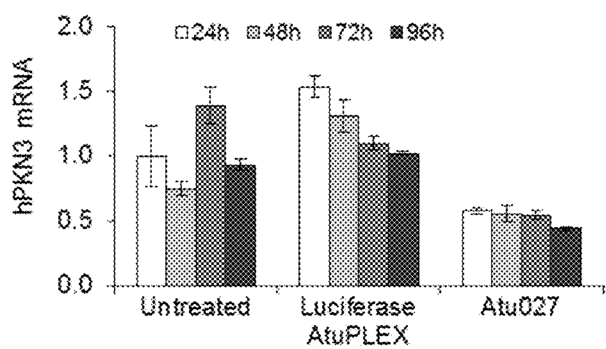
VEGFR-1 expression
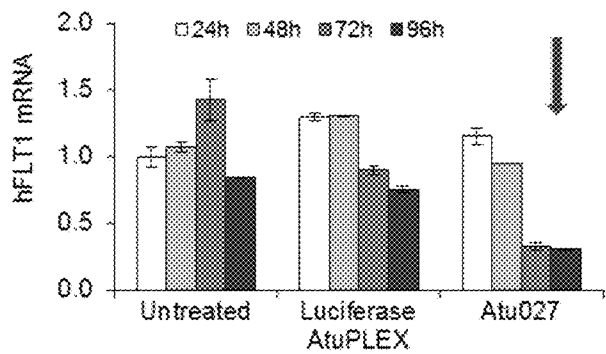
VEGFR-2 expression
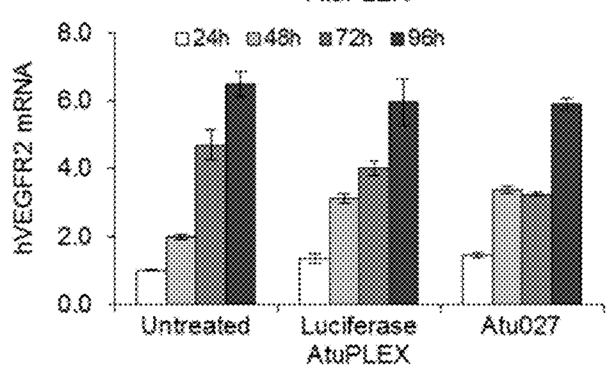
Fig. 1

VEGFR1 biomarker in response to PKN3 knock down in MDA-MB-435 cells
PKN3 knock down
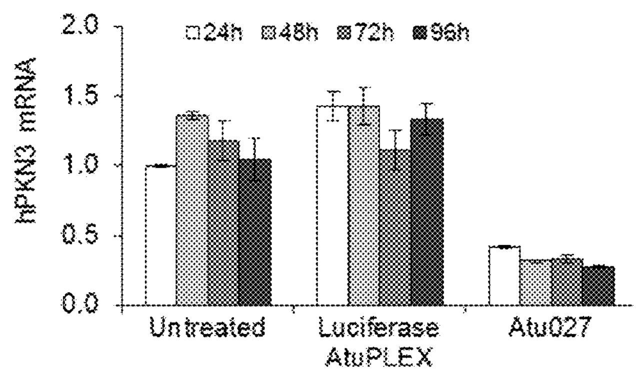
VEGFR-1 expression
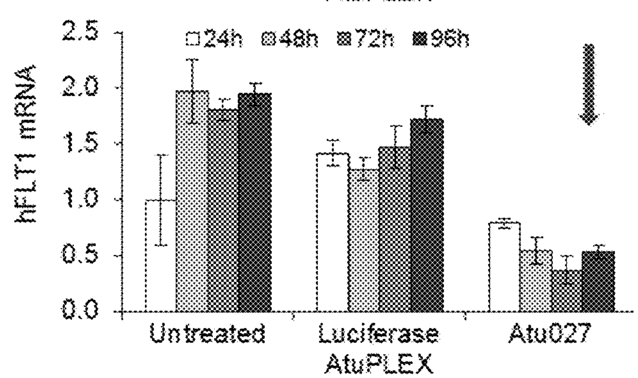
VEGFR-2 expression
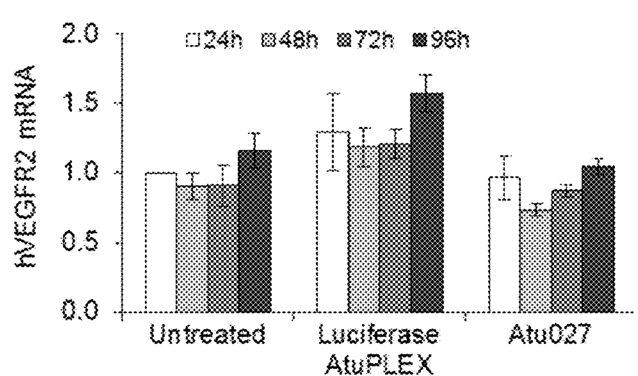
Fig. 2

| Dose level | Atu027 - Dose [mg/kg] based on the siRNA content |
|---|---|
| 6 | 0.072 |
| 7 | 0.120 |
| 8 | 0.180 |
| 9 | 0.253 |

| Dose level | Atu027 - Dose [mg/kg] based on the siRNA content |
|---|---|
| 6 | 0.072 |
| 7 | 0.120 |
| 8 | 0.180 |
| 9 | 0.253 |

Biomarker analysis in plasma from humans treated with Atu027

Single analytes- VEGF-C

| Dose level | Atu027 - Dose [mg/kg] based on the siRNA content |
|---|---|
| 6 | 0.072 |
| 7 | 0.120 |
| 8 | 0.180 |
| 9 | 0.253 |

| Dose level | Atu027 - Dose [mg/kg] based on the siRNA content |
|---|---|
| 6 | 0.072 |
| 7 | 0.120 |
| 8 | 0.180 |
| 9 | 0.253 |

Biomarker analysis in plasma from humans treated with Atu027

Single analytes- VEGFR-1

| Dose level | Atu027 - Dose [mg/kg] based on the siRNA content |
|---|---|
| 6 | 0.072 |
| 7 | 0.120 |
| 8 | 0.180 |
| 9 | 0.253 |

Biomarker analysis in plasma from humans treated with Atu027

Single analytes- VEGFR-2

Least detectable dose: 0.041 ng/mL

| Dose level | Atu027 - Dose [mg/kg] based on the siRNA content |
|---|---|
| 6 | 0.072 |
| 7 | 0.120 |
| 8 | 0.180 |
| 9 | 0.253 |

| Dose level | Atu027 - Dose [mg/kg] based on the siRNA content |
|---|---|
| 6 | 0.072 |
| 7 | 0.120 |
| 8 | 0.180 |
| 9 | 0.253 |

Fig. 13

SEQ ID NO: 1

MVSYWDTGVLLCALLSCLLLTGSSSGSKLKDPELSLKGTQHIMQ

AGQTLHLQCRGEAAHKWSLPEMVSKESERLSITKSACGRNGKQFCSTLTLNTAQANHT

GFYSCKYLAVPTSKKKETESAIYIFISDTGRPFVEMYSEIPEIIHMTEGRELVIPCRV

TSPNITVTLKKFPLDTLIPDGKRIIWDSRKGFIISNATYKEIGLLTCEATVNGHLYKT

NYLTHRQTNTIIDVQISTPRPVKLLRGHTLVLNCTATTPLNTRVQMTWSYPDEKNKRA

SVRRRIDQSNSHANIFYSVLTIDKMQNKDKGLYTCRVRSGPSFKSVNTSVHIYDKAFI

TVKHRKQQVLETVAGKRSYRLSMKVKAFPSPEVVWLKDGLPATEKSARYLTRGYSLII

KDVTEEDAGNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGNRIESITQR

MAIIEGKNKMASTLVVADSRISGIYICIASNKVGTVGRNISFYITDVPNGFHVNLEKM

PTEGEDLKLSCTVNKFLYRDVTWILLRTVNNRTMHYSISKQKMAITKEHSITLNLTIM

NVSLQDSGTYACRARNVYTGEEILQKKEITIRGEHCNKKAVFSRISKFKSTRNDCTTQ

SNVKH

Fig. 14

SEQ ID NO: 2

```
   1 atcgaggtcc gcgggaggct cggagcgcgc caggcggaca ctcctctcgg ctcctccccg
  61 gcagcggcgg cggctcggag cgggctccgg ggctcgggtg cagcggccag cgggcgcctg
 121 gcggcgagga ttacccgggg aagtggttgt ctcctggctg gagccgcgag acgggcgctc
 181 agggcgcggg gccggcggcg gcgaacgaga ggacggactc tggcggccgg gtcgttggcc
 241 gcggggagcg cgggcaccgg gcgagcaggc cgcgtcgcgc tcaccatggt cagctactgg
 301 gacaccgggg tcctgctgtg cgcgctgctc agctgtctgc ttctcacagg atctagttca
 361 ggttcaaaat taaaagatcc tgaactgagt ttaaaaggca cccagcacat catgcaagca
 421 ggccagacac tgcatctcca atgcaggggg gaagcagccc ataaatggtc tttgcctgaa
 481 atggtgagta aggaaagcga aaggctgagc ataactaaat ctgcctgtgg aagaaatggc
 541 aaacaattct gcagtacttt aaccttgaac acagctcaag caaaccacac tggcttctac
 601 agctgcaaat atctagctgt acctacttca aagaagaagg aaacagaatc tgcaatctat
 661 atatttatta gtgatacagg tagacctttc gtagagatgt acagtgaaat ccccgaaatt
 721 atacacatga ctgaaggaag ggagctcgtc attccctgcc gggttacgtc acctaacatc
 781 actgttactt taaaaaagtt tccacttgac actttgatcc ctgatggaaa acgcataatc
 841 tgggacagta gaaagggctt catcatatca aatgcaacgt acaaagaaat agggcttctg
 901 acctgtgaag caacagtcaa tgggcatttg tataagacaa actatctcac acatcgacaa
 961 accaatacaa tcatagatgt ccaaataagc acaccacgcc cagtcaaatt acttagaggc
1021 catactcttg tcctcaattg tactgctacc actcccttga acacgagagt tcaaatgacc
1081 tggagttacc ctgatgaaaa aaataagaga gcttccgtaa ggcgacgaat tgaccaaagc
1141 aattcccatg ccaacatatt ctacagtgtt cttactattg acaaaatgca gaacaaagac
1201 aaaggacttt atacttgtcg tgtaaggagt ggaccatcat tcaaatctgt taacacctca
1261 gtgcatatat atgataaagc attcatcact gtgaaacatc gaaaacagca ggtgcttgaa
1321 accgtagctg gcaagcggtc ttaccggctc tctatgaaag tgaaggcatt tccctcgccg
1381 gaagttgtat ggttaaaaga tgggttacct gcgactgaga aatctgctcg ctatttgact
1441 cgtggctact cgttaattat caaggacgta actgaagagg atgcagggaa ttatacaatc
1501 ttgctgagca taaaacagtc aaatgtgttt aaaaacctca ctgccactct aattgtcaat
1561 gtgaaacccc agatttacga aaaggccgtg tcatcgtttc cagacccggc tctctaccca
1621 ctgggcagca gacaaatcct gacttgtacc gcatatggta tccctcaacc tacaatcaag
1681 tggttctggc acccctgtaa ccataatcat tccgaagcaa ggtgtgactt ttgttccaat
1741 aatgaagagt cctttatcct ggatgctgac agcaacatgg gaaacagaat tgagagcatc
1801 actcagcgca tggcaataat agaaggaaag aataagatgg ctagcacctt ggttgtggct
1861 gactctagaa tttctggaat ctacatttgc atagcttcca ataaagttgg gactgtggga
1921 agaaacataa gcttttatat cacagatgtg ccaaatgggt ttcatgttaa cttggaaaaa
1981 atgccgacgg aaggagagga cctgaaactg tcttgcacag ttaacaagtt cttatacaga
2041 gacgttactt ggattttact gcggacagtt aataacagaa caatgcacta cagtattagc
2101 aagcaaaaaa tggccatcac taaggagcac tccatcactc ttaatcttac catcatgaat
2161 gtttccctgc aagattcagg cacctatgcc tgcagagcca ggaatgtata cacaggggaa
2221 gaaatcctcc agaagaaaga aattacaatc agaggtgagc actgcaacaa aaaggctgtt
2281 ttctctcgga tctccaaatt taaaagcaca aggaatgatt gtaccacaca aagtaatgta
2341 aaacattaaa ggactcatta aaaagtaaca gttgtctcat atcatcttga tttattgtca
2401 ctgttgctaa ctttcaggct cggaggagat gctcctccca aaatgagttc ggagatgata
2461 gcagtaataa tgagaccccc gggccccagc tctgggcccc ccattcaggc cgagggggct
2521 gctccggggg gccgacttgg tgcacgtttg gatttggagg atccctgcac tgccttctct
2581 gtgtttgttg ctcttgctgt ttctcctgc ctgataaaca acaacttggg atgatccttt
2641 ccttccattt tgatgccaac ctctttttat ttttaagtgt tgaagctgca caaactgaat
2701 aatttaaaca aatgctggtt tctgccaaag atggacacga ataagttaat tttccagctc
2761 agaatgagta cagttgaatt tgagactctg tcggacttct gcctggtttt atttgggact
2821 atttcatctg ctcttgattt gtaaatagca cctggatagc aagttataat gcttatttat
2881 ttgaaaatgc tttttttttt tttacgttaa gcacatttat cttgaactgg agcttctaaa
2941 atgggcccca ggggtgcaag atgttggtgt aattcagaga tagtaaaggt ttatcgcagt
3001 gtgaattata agagtccatc caaatcaacg tcccctccct cctctcatgc gatccaggta
```

Fig. 14 (continued)

```
3061 attatgcagt tagtgccaca gtagactagc ctagcaaagg gtttgctcct tgctgtctct
3121 gactgcacca cacagctatt gatggcagct gaaagaaagt ggatcatgcc ttaattttaa
3181 atattcctgt cctctggtta ttattttaag gaacttcatc atgttaaaat gacagcattc
3241 aaaggtgtac cacaatcaat ttatcaagga aataaaggct attgtaacca gagatttaat
3301 gcattcttct aaatgtaaat ttaaaatttg ccctttaaaa aagtccactt tccccatatg
3361 caaatgttaa taggattttt atggggatta agaagcggca aaactacaga agcagaattc
3421 aaagtaattt aaaaaataca caccagtttt aaatcaagag aagttgtaat ctcttgtttt
3481 aagcttgcgt ttgagggaaa atgacttttt caccaattta atatgcattg ttctgttgtt
3541 tttatttatg attgatcatt atatgtgact tgcataaact atttaaaaaa aaaaactata
3601 atgaccaaaa tagccatggc tgagaaacac agtggctggg cagttcaata ggaggtgaca
3661 atatgacaac ttctcaagct tgggaactca ccagactgtt tcctccttta ggtaacagat
3721 tctgtcccac ggctaaactt gtctttcacg tgggaattgc ttttgtcaaa cgtgaaagag
3781 taaacaatag catttcccca gaatgccagt tttatggagc cccaaatgct ctgaaaacaa
3841 ttagtaacct ggaagttgtc agcccaaagg aaagaaaaat caattgtatc ttgaaatttt
3901 acctatggct ctttggcctg gcttctttgt tcattataag ttagtgtgtt ccttcaggaa
3961 acaatgcctt aataccatag aacatggggg ccttaatagt tgctaacatt aaaaaagcaa
4021 acagaatgat tgaggatcc ttatgaaaac aaaatggtga attggacatg cagaacctac
4081 catttccttc ccctgtttgc aatttttgtg gggaggggag gatgttagta tttacaaaag
4141 atgattttaa gaacttccaa gagatgagtt taagaattcc atagagtatt agttgttcac
4201 tgtgtaatta atccttccgg agagtctttt tttttttttt taaagaaact tttgggtggg
4261 ttttgttttt tattagttac cctaggggta tgttaccctg ggtatgaag ggaggtgaag
4321 ataacggagg ggggagaaaa aaaaaaggag aaaaaaggag cctaaaatgg ggaataattg
4381 aaatggaaca gggggtgtga ggctggttcc tcagtcccca ttccaaacgg aggatagaag
4441 ctgtgtattt atgtgacctg gcagatctct ggggccataa cactgaaaag tgaaagaacc
4501 tggtgggcag ctatctttgg ctactgataa ccagcagaaa tgtctgttaa ttctgatttt
4561 ctcaatttga agggatcagc tacactgtta aattttggaa agccactacc tacttccatc
4621 aagtaactta ggtttcgaaa tatgggttca acgcacctcc cttattcaaa atgtcaaaat
4681 agattattat aatgtataaa gtaagaattg acaaaatatg attcttgggt tgattggtca
4741 tttagaaact agccaaaagt gagactttta atgtagaaca tttttcagaa atgggtacaa
4801 agaaaaatgc atattactgt atatttcaga gtgtttatgt gaaccttgta tttaattgag
4861 agtcccatgt acgttctgca gccttttttgc tgcttctatc atctgaagtt tgtgtagtac
4921 aaataaggcc tttgggattc ttaatgacat ttatgttaaa atgttctctt ctctttaaac
4981 accgttttcc aatccacctg tcagggagtc caaatcgtgt ctgtgttgat gatgctatac
5041 tttgtagcta gaaaaacaat tttagtgttg tgggctctgt attcagactt cctttttaca
5101 agaccgatgg gcagtgatag attattttat catatttaat gcatgggaaa tagtgtgctg
5161 aggaagctat taaaagtata actcagtgaa ttgggtctga gttttaaatg agatatttca
5221 aaattggctt gccactgtaa aagcgactaa ataataatat gatactgttc tttatgatct
5281 tgtcatgttt cactgatatg tttggggtct tcactatgta aaaaatgtca aaattgtaat
5341 gagcaagcat gtacaagtag tcgtaaatca aaggttttaa acaggactgc attttcaatt
5401 aggaaaagct gtttggcaga tagcatccaa tgcaaaaaca gaaatatcgt aacgttctgc
5461 ttagtgggca agataagata ggaaagacat gctcaaagag gcaaaagaat cattgctatc
5521 attcattcta cactagtttg aagaagtttt tgtacatcag agcacttcct tcagcacact
5581 tttttgcctt cagatttcat tttttataaa atgagaagac taatgataaa ctgtagaaat
5641 caaaatttat tgagaaatct gtttctccta acagatagta accctgccat gatatactac
5701 ttcaacaatg ttataaaatt tatgtgataa tatacatttt aacctgggat ttctaaattg
5761 ctttaacaaa tgctaatcct gagagttgcc ctgcaggact caaaagggaa aggttttggg
5821 acgtggcaga accctgcagg gacatggaat taaggccatt gcaatgtatc atctttgtag
5881 cattgtcatc actcctaagc tgccttcaca gttttagtac actaagatga ggaaatcgaa
5941 aatgggcaga gaaagctcat actgtataat tgaagacagt gacagagaac gtgtcagtta
6001 tgccaaaact cttttgattt ctgttccagg atttccaaca agaggggaaa ggaatgactt
6061 gggagggtgg gaaagacatt aggagttgtt tttattttt accttggaag ctttagctac
6121 caatccagta ccctcctaac tagaatgtat acacatcagc aggactgact gactacttca
6181 ttagagatat actgtactca ttgggggcct tgggggtact gctgttctta tgtgggattt
6241 taatgttgta atgtattgca tcttaatgta ttgaattcat tttgttgtac tatattggtt
6301 ggcattttat taaaataaat tgtattgtat catatttgta tgttttaaga gaaaataata
6361 taaaatacaa tatttgtact attatatagt gcaaaaacta caaatctgtg cctctgcctc
6421 ttgaattaat tctttggttg cttgcatttg ggaagggaat ggagaaagga aagaaccaat
6481 aaagctttca aagttcaag
```

Fig. 15

SEQ ID NO: 3

MVSYWDTGVLLCALLSCLLLTGSSSGSKLKDPELSLKGTQHIMQ

AGQTLHLQCRGEAAHKWSLPEMVSKESERLSITKSACGRNGKQFCSTLTLNTAQANHT

GFYSCKYLAVPTSKKKETESAIYIFISDTGRPFVEMYSEIPEIIHMTEGRELVIPCRV

TSPNITVTLKKFPLDTLIPDGKRIIWDSRKGFIISNATYKEIGLLTCEATVNGHLYKT

NYLTHRQTNTIIDVQISTPRPVKLLRGHTLVLNCTATTPLNTRVQMTWSYPDEKNKRA

SVRRRIDQSNSHANIFYSVLTIDKMQNKDKGLYTCRVRSGPSFKSVNTSVHIYDKAFI

TVKHRKQQVLETVAGKRSYRLSMKVKAFPSPEVVWLKDGLPATEKSARYLTRGYSLII

KDVTEEDAGNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGNRIESITQR

MAIIEGKNKMASTLVVADSRISGIYICIASNKVGTVGRNISFYITDVPNGFHVNLEKM

PTEGEDLKLSCTVNKFLYRDVTWILLRTVNNRTMHYSISKQKMAITKEHSITLNLTIM

NVSLQDSGTYACRARNVYTGEEILQKKEITIRDQEAPYLLRNLSDHTVAISSSTTLDC

HANGVPEPQITWFKNNHKIQQEPGIILGPGSSTLFIERVTEEDEGVYHCKATNQKGSV

ESSAYLTVQGTSDKSNLELITLTCTCVAATLFWLLLTLFIRKMKRSSSEIKTDYLSII

MDPDEVPLDEQCERLPYDASKWEFARERLKLGKSLGRGAFGKVVQASAFGIKKSPTCR

TVAVKMLKEGATASEYKALMTELKILTHIGHHLNVVNLLGACTKQGGPLMVIVEYCKY

GNLSNYLKSKRDLFFLNKDAALHMEPKKEKMEPGLEQGKKPRLDSVTSSESFASSGFQ

EDKSLSDVEEEEDSDGFYKEPITMEDLISYSFQVARGMEFLSSRKCIHRDLAARNILL

SENNVVKICDFGLARDIYKNPDYVRKGDTRLPLKWMAPESIFDKIYSTKSDVWSYGVL

LWEIFSLGGSPYPGVQMDEDFCSRLREGMRMRAPEYSTPEIYQIMLDCWHRDPKERPR

FAELVEKLGDLLQANVQQDGKDYIPINAILTGNSGFTYSTPAFSEDFFKESISAPKFN

SGSSDDVRYVNAFKFMSLERIKTFEELLPNATSMFDDYQGDSSTLLASPMLKRFTWTD

SKPKASLKIDLRVTSKSKESGLSDVSRPSFCHSSCGHVSEGKRRFTYDHAELERKIAC

CSPPPDYNSVVLYSTPPI

Fig. 16

SEQ ID NO: 4

```
   1 atcgaggtcc gcgggaggct cggagcgcgc caggcggaca ctcctctcgg ctcctccccg
  61 gcagcggcgg cggctcggag cgggctccgg ggctcgggtg cagcggccag cgggcgcctg
 121 gcggcgagga ttacccgggg aagtggttgt ctcctggctg gagccgcgag acgggcgctc
 181 agggcgcggg gccggcggcg gcgaacgaga ggacggactc tggcggccgg gtcgttggcc
 241 gcggggagcg cgggcaccgg gcgagcaggc cgcgtcgcgc tcaccatggt cagctactgg
 301 gacaccgggg tcctgctgtg cgcgctgctc agctgtctgc ttctcacagg atctagttca
 361 ggttcaaaat taaaagatcc tgaactgagt ttaaaaggca cccagcacat catgcaagca
 421 ggccagacac tgcatctcca atgcaggggg gaagcagccc ataaatggtc tttgcctgaa
 481 atggtgagta aggaaagcga aaggctgagc ataactaaat ctgcctgtgg aagaaatggc
 541 aaacaattct gcagtacttt aaccttgaac acagctcaag caaaccacac tggcttctac
 601 agctgcaaat atctagctgt acctacttca aagaagaagg aaacagaatc tgcaatctat
 661 atatttatta gtgatacagg tagacctttc gtagagatgt acagtgaaat ccccgaaatt
 721 atacacatga ctgaaggaag ggagctcgtc attccctgcc gggttacgtc acctaacatc
 781 actgttactt taaaaaagtt tccacttgac actttgatcc ctgatggaaa acgcataatc
 841 tgggacagta gaaagggctt catcatatca aatgcaacgt acaaagaaat agggcttctg
 901 acctgtgaag caacagtcaa tgggcatttg tataagacaa actatctcac acatcgacaa
 961 accaatacaa tcatagatgt ccaaataagc acaccacgcc cagtcaaatt acttagaggc
1021 catactcttg tcctcaattg tactgctacc actcccttga acacgagagt tcaaatgacc
1081 tggagttacc ctgatgaaaa aaataagaga gcttccgtaa ggcgacgaat tgaccaaagc
1141 aattcccatg ccaacatatt ctacagtgtt cttactattg acaaaatgca gaacaaagac
1201 aaaggacttt atacttgtcg tgtaaggagt ggaccatcat tcaaatctgt taacacctca
1261 gtgcatatat atgataaagc attcatcact gtgaaacatc gaaaacagca ggtgcttgaa
1321 accgtagctg gcaagcggtc ttaccggctc tctatgaaag tgaaggcatt tccctcgccg
1381 gaagttgtat ggttaaaaga tgggttacct gcgactgaga aatctgctcg ctatttgact
1441 cgtggctact cgttaattat caaggacgta actgaagagg atgcagggaa ttatacaatc
1501 ttgctgagca taaaacagtc aaatgtgttt aaaaacctca ctgccactct aattgtcaat
1561 gtgaaacccc agatttacga aaaggccgtg tcatcgtttc cagacccggc tctctaccca
1621 ctgggcagca gacaaatcct gacttgtacc gcatatggta tccctcaacc tacaatcaag
1681 tggttctggc accccctgtaa ccataatcat tccgaagcaa ggtgtgactt ttgttccaat
1741 aatgaagagt cctttatcct ggatgctgac agcaacatgg gaaacagaat tgagagcatc
1801 actcagcgca tggcaataat agaaggaaag aataagatgg ctagcacctt ggttgtggct
1861 gactctagaa tttctggaat ctacatttgc atagcttcca ataaagttgg gactgtggga
1921 agaaacataa gcttttatat cacagatgtg ccaaatgggt ttcatgttaa cttggaaaaa
1981 atgccgacgg aaggagagga cctgaaactg tcttgcacag ttaacaagtt cttatacaga
2041 gacgttactt ggattttact gcggacagtt aataacagaa caatgcacta cagtattagc
2101 aagcaaaaaa tggccatcac taaggagcac tccatcactc ttaatcttac catcatgaat
2161 gtttccctgc aagattcagg cacctatgcc tgcagagcca ggaatgtata cacaggggaa
2221 gaaatcctcc agaagaaaga aattacaatc agagatcagg aagcaccata cctcctgcga
2281 aacctcagtg atcacacagt ggccatcagc agttccacca ctttagactg tcatgctaat
2341 ggtgtccccg agcctcagat cacttggttt aaaaacaacc acaaaataca acaagagcct
2401 ggaattattt taggaccagg aagcagcacg ctgtttattg aaagagtcac agaagaggat
2461 gaaggtgtct atcactgcaa agccaccaac cagaagggct ctgtggaaag ttcagcatac
2521 ctcactgttc aaggaacctc ggacaagtct aatctggagc tgatcactct aacatgcacc
2581 tgtgtggctg cgactctctt ctggctccta ttaaccctct ttatccgaaa aatgaaaagg
2641 tcttcttctg aaataaagac tgactaccta tcaattataa tggacccaga tgaagttcct
2701 ttggatgagc agtgtgagcg gctcccttat gatgccagca agtgggagtt tgcccgggag
2761 agacttaaac tgggcaaatc acttggaaga ggggcttttg gaaaagtggt tcaagcatca
2821 gcatttggca ttaagaaatc acctacgtgc cggactgtgg ctgtgaaaat gctgaaagag
2881 ggggccacgg ccagcgagta caaagctctg atgactgagc taaaaatctt gacccacatt
2941 ggccaccatc tgaacgtggt taacctgctg ggagcctgca ccaagcaagg agggcctctg
3001 atggtgattg ttgaatactg caaatatgga aatctctcca actacctcaa gagcaaacgt
3061 gacttatttt ttctcaacaa ggatgcagca ctacacatgg agcctaagaa agaaaaaatg
3121 gagccaggcc tggaacaagg caagaaacca agactagata gcgtcaccag cagcgaaagc
3181 tttgcgagct ccggctttca ggaagataaa agtctgagtg atgttgagga agaggaggat
3241 tctgacggtt tctacaagga gcccatcact atggaagatc tgatttctta cagttttcaa
3301 gtggccagag gcatggagtt cctgtcttcc agaaagtgca ttcatcggga cctggcagcg
```

Fig. 16 (continued)

3361 agaaacattc ttttatctga gaacaacgtg gtgaagattt gtgattttgg ccttgcccgg
3421 gatatttata agaaccccga ttatgtgaga aaaggagata ctcgacttcc tctgaaatgg
3481 atggctcctg aatctatctt tgacaaaatc tacagcacca agagcgacgt gtggtcttac
3541 ggagtattgc tgtgggaaat cttctcctta ggtgggtctc catacccagg agtacaaatg
3601 gatgaggact tttgcagtcg cctgagggaa ggcatgagga tgagagctcc tgagtactct
3661 actcctgaaa tctatcagat catgctggac tgctggcaca gagacccaaa agaaaggcca
3721 agatttgcag aacttgtgga aaaactaggt gatttgcttc aagcaaatgt acaacaggat
3781 ggtaaagact acatcccaat caatgccata ctgacaggaa atagtgggtt tacatactca
3841 actcctgcct tctctgagga cttcttcaag gaaagtattt cagctccgaa gtttaattca
3901 ggaagctctg atgatgtcag atacgtaaat gctttcaagt tcatgagcct ggaaagaatc
3961 aaaacctttg aagaactttt accgaatgcc acctccatgt ttgatgacta ccagggcgac
4021 agcagcactc tgttggcctc tcccatgctg aagcgcttca cctggactga cagcaaaccc
4081 aaggcctcgc tcaagattga cttgagagta accagtaaaa gtaaggagtc ggggctgtct
4141 gatgtcagca ggcccagttt ctgccattcc agctgtgggc acgtcagcga aggcaagcgc
4201 aggttcacct acgaccacgc tgagctggaa aggaaaatcg cgtgctgctc cccgccccca
4261 gactacaact cggtggtcct gtactccacc ccacccatct agagtttgac acgaagcctt
4321 atttctagaa gcacatgtgt atttataccc ccaggaaact agcttttgcc agtattatgc
4381 atatataagt ttacaccttt atctttccat gggagccagc tgctttttgt gattttttta
4441 atagtgcttt tttttttttg actaacaaga atgtaactcc agatagagaa atagtgacaa
4501 gtgaagaaca ctactgctaa atcctcatgt tactcagtgt tagagaaatc cttcctaaac
4561 ccaatgactt ccctgctcca acccccgcca cctcagggca cgcaggacca gtttgattga
4621 ggagctgcac tgatcaccca atgcatcacg taccccactg ggccagccct gcagcccaaa
4681 acccagggca acaagcccgt tagccccagg gatcactggc tggcctgagc aacatctcgg
4741 gagtcctcta gcaggcctaa gacatgtgag gaggaaaagg aaaaaaagca aaaagcaagg
4801 gagaaaagag aaaccgggag aaggcatgag aaagaatttg agacgcacca tgtgggcacg
4861 gaggggggacg gggctcagca atgccatttc agtggcttcc cagctctgac ccttctacat
4921 ttgagggccc agccaggagc agatggacag cgatgagggg acattttctg gattctggga
4981 ggcaagaaaa ggacaaatat cttttttgga actaaagcaa atttagaac tttacctatg
5041 gaagtggttc tatgtccatt ctcattcgtg gcatgttttg atttgtagca ctgagggtgg
5101 cactcaactc tgagcccata cttttggctc ctctagtaag atgcactgaa aacttagcca
5161 gagttaggtt gtctccaggc catgatggcc ttacactgaa aatgtcacat tctattttgg
5221 gtattaatat atagtccaga cacttaactc aatttcttgg tattattctg ttttgcacag
5281 ttagttgtga aagaaagctg agaagaatga aaatgcagtc ctgaggagag gagttttctc
5341 catatcaaaa cgagggctga tggaggaaaa aggtcaataa ggtcaaggga aaaccccgtc
5401 tctataccaa ccaaaccaat tcaccaacac agttgggacc caaaacacag gaagtcagtc
5461 acgtttcctt ttcatttaat ggggattcca ctatctcaca ctaatctgaa aggatgtgga
5521 agagcattag ctggcgcata ttaagcactt taagctcctt gagtaaaaag gtggtatgta
5581 atttatgcaa ggtatttctc cagttgggac tcaggatatt agttaatgag ccatcactag
5641 aagaaaagcc cattttcaac tgctttgaaa cttgcctggg gtctgagcat gatgggaata
5701 gggagacagg gtaggaaagg gcgcctactc ttcagggtct aaagatcaag tgggccttgg
5761 atcgctaagc tggctctgtt tgatgctatt tatgcaagtt agggtctatg tatttatgat
5821 gtctgcacct tctgcagcca gtcagaagct ggagaggcaa cagtggattg ctgcttcttg
5881 gggagaagag tatgcttcct tttatccatg taatttaact gtagaacctg agctctaagt
5941 aaccgaagaa tgtatgcctc tgttcttatg tgccacatcc ttgtttaaag gctctctgta
6001 tgaagagatg ggaccgtcat cagcacattc cctagtgagc ctactggctc ctggcagcgg
6061 cttttgtgga agactcacta gccagaagag aggagtggga cagtcctctc caccaagatc
6121 taaatccaaa caaaagcagg ctagagccag aagagaggac aaatctttgt tcttcctctt
6181 ctttacatac gcaaaccacc tgtgacagct ggcaatttta taaatcaggt aactggaagg
6241 aggttaaaca cagaaaaaag aagacctcag tcaattctct actttttttt tttttccaa
6301 atcagataat agcccagcaa atagtgataa caaataaaac cttagctatt catgtcttga
6361 tttcaataat taattcttaa tcattaagag accataataa atactccttt tcaagagaaa
6421 agcaaaacca ttagaattgt tactcagctc cttcaaactc aggtttgtag catacatgag
6481 tccatccatc agtcaaagaa tggttccatc tggagtctta atgtagaaag aaaaatggag
6541 acttgtaata atgagctagt tacaaagtgc ttgttcatta aaatagcact gaaaattgaa
6601 acatgaatta actgataata ttccaatcat ttgccattta tgacaaaaat ggttggcact
6661 aacaaagaac gagcacttcc tttcagagtt tctgagataa tgtacgtgga acagtctggg
6721 tggaatgggg ctgaaaccat gtgcaagtct gtgtcttgtc agtccaagaa gtgacaccga
6781 gatgttaatt ttagggaccc gtgccttgtt tcctagccca caagaatgca aacatcaaac
6841 agatactcgc tagcctcatt taaattgatt aaaggaggag tgcatctttg gccgacagtg Fig. 16 (continued)

```
6901 gtgtaactgt atgtgtgtgt gtgtgtgtgt gtgtgtgtgt gtgtgtgggt gtatgtgtgt
6961 tttgtgcata actatttaag gaaactggaa ttttaaagtt acttttatac aaaccaagaa
7021 tatatgctac agatataaga cagacatggt ttggtcctat atttctagtc atgatgaatg
7081 tattttgtat accatcttca tataataaac ttccaaaaac aca
```

Fig. 17

SEQ ID NO: 5

MVSYWDTGVLLCALLSCLLLTGSSSGSKLKDPELSLKGTQHIMQ

AGQTLHLQCRGEAAHKWSLPEMVSKESERLSITKSACGRNGKQFCSTLTLNTAQANHT

GFYSCKYLAVPTSKKKETESAIYIFISDTGRPFVEMYSEIPEIIHMTEGRELVIPCRV

TSPNITVTLKKFPLDTLIPDGKRIIWDSRKGFIISNATYKEIGLLTCEATVNGHLYKT

NYLTHRQTNTIIDVQISTPRPVKLLRGHTLVLNCTATTPLNTRVQMTWSYPDEKNKRA

SVRRRIDQSNSHANIFYSVLTIDKMQNKDKGLYTCRVRSGPSFKSVNTSVHIYDKAFI

TVKHRKQQVLETVAGKRSYRLSMKVKAFPSPEVVWLKDGLPATEKSARYLTRGYSLII

KDVTEEDAGNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGNRIESITQR

MAIIEGKNKMASTLVVADSRISGIYICIASNKVGTVGRNISFYITDVPNGFHVNLEKM

PTEGEDLKLSCTVNKFLYRDVTWILLRTVNNRTMHYSISKQKMAITKEHSITLNLTIM

NVSLQDSGTYACRARNVYTGEEILQKKEITIRDQEAPYLLRNLSDHTVAISSSTTLDC

HANGVPEPQITWFKNNHKIQQEPELYTSTSPSSSSSSPLSSSSSSSSSSS

Fig. 18

SEQ ID NO: 6

```
   1 atcgaggtcc gcgggaggct cggagcgcgc caggcggaca ctcctctcgg ctcctccccg
  61 gcagcggcgg cggctcggag cgggctccgg ggctcgggtg cagcggccag cgggcgcctg
 121 gcggcgagga ttacccgggg aagtggttgt ctcctggctg gagccgcgag acgggcgctc
 181 agggcgcggg gccggcggcg gcgaacgaga ggacggactc tggcggccgg gtcgttggcc
 241 gcggggagcg cgggcaccgg gcgagcaggc cgcgtcgcgc tcaccatggt cagctactgg
 301 gacaccgggg tcctgctgtg cgcgctgctc agctgtctgc ttctcacagg atctagttca
 361 ggttcaaaat taaaagatcc tgaactgagt ttaaaaggca cccagcacat catgcaagca
 421 ggccagacac tgcatctcca atgcaggggg gaagcagccc ataaatggtc tttgcctgaa
 481 atggtgagta aggaaagcga aaggctgagc ataactaaat ctgcctgtgg aagaaatggc
 541 aaacaattct gcagtacttt aaccttgaac acagctcaag caaaccacac tggcttctac
 601 agctgcaaat atctagctgt acctacttca aagaagaagg aaacagaatc tgcaatctat
 661 atatttatta gtgatacagg tagacctttc gtagagatgt acagtgaaat ccccgaaatt
 721 atacacatga ctgaaggaag ggagctcgtc attccctgcc gggttacgtc acctaacatc
 781 actgttactt taaaaaagtt tccacttgac actttgatcc ctgatggaaa acgcataatc
 841 tgggacagta gaaagggctt catcatatca aatgcaacgt acaaagaaat agggcttctg
 901 acctgtgaag caacagtcaa tgggcatttg tataagacaa actatctcac acatcgacaa
 961 accaatacaa tcatagatgt ccaaataagc acaccacgcc cagtcaaatt acttagaggc
1021 catactcttg tcctcaattg tactgctacc actcccttga acacgagagt tcaaatgacc
1081 tggagttacc ctgatgaaaa aaataagaga gcttccgtaa ggcgacgaat tgaccaaagc
1141 aattcccatg ccaacatatt ctacagtgtt cttactattg acaaaatgca gaacaaagac
1201 aaaggacttt atacttgtcg tgtaaggagt ggaccatcat tcaaatctgt taacacctca
1261 gtgcatatat atgataaagc attcatcact gtgaaacatc gaaaacagca ggtgcttgaa
1321 accgtagctg gcaagcggtc ttaccggctc tctatgaaag tgaaggcatt tccctcgccg
1381 gaagttgtat ggttaaaaga tgggttacct gcgactgaga aatctgctcg ctatttgact
1441 cgtggctact cgttaattat caaggacgta actgaagagg atgcagggaa ttatacaatc
1501 ttgctgagca taaaacagtc aaatgtgttt aaaaacctca ctgccactct aattgtcaat
1561 gtgaaacccc agatttacga aaaggccgtg tcatcgtttc cagacccggc tctctaccca
1621 ctgggcagca gacaaatcct gacttgtacc gcatatggta tccctcaacc tacaatcaag
1681 tggttctggc acccctgtaa ccataatcat tccgaagcaa ggtgtgactt ttgttccaat
1741 aatgaagagt cctttatcct ggatgctgac agcaacatgg gaaacagaat tgagagcatc
1801 actcagcgca tggcaataat agaaggaaag aataagatgg ctagcacctt ggttgtggct
1861 gactctagaa tttctggaat ctacatttgc atagcttcca ataaagttgg gactgtggga
1921 agaaacataa gcttttatat cacagatgtg ccaaatgggt ttcatgttaa cttggaaaaa
1981 atgccgacgg aaggagagga cctgaaactg tcttgcacag ttaacaagtt cttatacaga
2041 gacgttactt ggattttact gcggacagtt aataacagaa caatgcacta cagtattagc
2101 aagcaaaaaa tggccatcac taaggagcac tccatcactc ttaatcttac catcatgaat
2161 gtttccctgc aagattcagg cacctatgcc tgcagagcca ggaatgtata cacaggggaa
2221 gaaatcctcc agaagaaaga aattacaatc agagatcagg aagcaccata cctcctgcga
2281 aacctcagtg atcacacagt ggccatcagc agttccacca ctttagactg tcatgctaat
2341 ggtgtccccg agcctcagat cacttggttt aaaaacaacc acaaaataca acaagagcct
2401 gaactgtata catcaacgtc accatcgtca tcgtcatcat caccattgtc atcatcatca
```

Fig. 18 (continued)

```
2461 tcatcgtcat catcatcatc atcatagcta tcatcattat catcatcatc atcatcatca
2521 tcatagctac catttattga aaactattat gtgtcaactt caaagaactt atcctttagt
2581 tggagagcca agacaatcat aacaataaca aatggccggg catggtggct cacgcctgta
2641 atcccagcac tttgggaggc caaggcaggt ggatcatttg aggtcaggag ttcaagacca
2701 gcctgaccaa gatggtgaaa tgctgtctct attaaaaata caaaattagc caggcatggt
2761 ggctcatgcc tgtaatgcca gctactcggg aggctgagac aggagaatca cttgaaccca
2821 ggaggcagag gttgcaggga gccgagatcg tgtactgcac tccagcctgg gcaacaagag
2881 cgaaactccg tctcaaaaaa caaataaata aataaataaa taaacagaca aaattcactt
2941 tttattctat taaacttaac atacatgc
```

Fig. 19

SEQ ID NO: 7

MVSYWDTGVLLCALLSCLLLTGSSSGSKLKDPELSLKGTQHIMQ

AGQTLHLQCRGEAAHKWSLPEMVSKESERLSITKSACGRNGKQFCSTLTLNTAQANHT

GFYSCKYLAVPTSKKKETESAIYIFISDTGRPFVEMYSEIPEIIHMTEGRELVIPCRV

TSPNITVTLKKFPLDTLIPDGKRIIWDSRKGFIISNATYKEIGLLTCEATVNGHLYKT

NYLTHRQTNTIIDVQISTPRPVKLLRGHTLVLNCTATTPLNTRVQMTWSYPDEKNKRA

SVRRRIDQSNSHANIFYSVLTIDKMQNKDKGLYTCRVRSGPSFKSVNTSVHIYDKAFI

TVKHRKQQVLETVAGKRSYRLSMKVKAFPSPEVVWLKDGLPATEKSARYLTRGYSLII

KDVTEEDAGNYTILLSIKQSNVFKNLTATLIVNVKPQIYEKAVSSFPDPALYPLGSRQ

ILTCTAYGIPQPTIKWFWHPCNHNHSEARCDFCSNNEESFILDADSNMGNRIESITQR

MAIIEGKNKLPPANSSFMLPPTSFSSNYFHFLP

Fig. 20

SEQ ID NO: 8

```
   1 atcgaggtcc gcgggaggct cggagcgcgc caggcggaca ctcctctcgg ctcctccccg
  61 gcagcggcgg cggctcggag cgggctccgg ggctcgggtg cagcggccag cgggcgcctg
 121 gcggcgagga ttacccgggg aagtggttgt ctcctggctg gagccgcgag acgggcgctc
 181 agggcgcggg gccggcggcg gcgaacgaga ggacggactc tggcggccgg gtcgttggcc
 241 gcggggagcg cgggcaccgg gcgagcaggc cgcgtcgcgc tcaccatggt cagctactgg
 301 gacaccgggg tcctgctgtg cgcgctgctc agctgtctgc ttctcacagg atctagttca
 361 ggttcaaaat taaaagatcc tgaactgagt ttaaaaggca cccagcacat catgcaagca
 421 ggccagacac tgcatctcca atgcaggggg gaagcagccc ataaatggtc tttgcctgaa
 481 atggtgagta aggaaagcga aaggctgagc ataactaaat ctgcctgtgg aagaaatggc
 541 aaacaattct gcagtacttt aaccttgaac acagctcaag caaaccacac tggcttctac
 601 agctgcaaat atctagctgt acctacttca aagaagaagg aaacagaatc tgcaatctat
 661 atatttatta gtgatacagg tagacctttc gtagagatgt acagtgaaat ccccgaaatt
 721 atacacatga ctgaaggaag ggagctcgtc attccctgcc gggttacgtc acctaacatc
 781 actgttactt taaaaaagtt tccacttgac actttgatcc ctgatggaaa acgcataatc
 841 tgggacagta gaaagggctt catcatatca aatgcaacgt acaaagaaat agggcttctg
 901 acctgtgaag caacagtcaa tgggcatttg tataagacaa actatctcac acatcgacaa
 961 accaatacaa tcatagatgt ccaaataagc acaccacgcc cagtcaaatt acttagaggc
1021 catactcttg tcctcaattg tactgctacc actcccttga acacgagagt tcaaatgacc
1081 tggagttacc ctgatgaaaa aaataagaga gcttccgtaa ggcgacgaat tgaccaaagc
1141 aattcccatg ccaacatatt ctacagtgtt cttactattg acaaaatgca gaacaaagac
1201 aaaggacttt atacttgtcg tgtaaggagt ggaccatcat tcaaatctgt taacacctca
1261 gtgcatatat atgataaagc attcatcact gtgaaacatc gaaaacagca ggtgcttgaa
1321 accgtagctg gcaagcggtc ttaccggctc tctatgaaag tgaaggcatt tccctcgccg
1381 gaagttgtat ggttaaaaga tgggttacct gcgactgaga aatctgctcg ctatttgact
1441 cgtggctact cgttaattat caaggacgta actgaagagg atgcagggaa ttatacaatc
1501 ttgctgagca taaaacagtc aaatgtgttt aaaaacctca ctgccactct aattgtcaat
1561 gtgaaacccc agatttacga aaaggccgtg tcatcgtttc cagacccggc tctctaccca
1621 ctgggcagca gacaaatcct gacttgtacc gcatatggta tccctcaacc tacaatcaag
1681 tggttctggc accccctgtaa ccataatcat tccgaagcaa ggtgtgactt ttgttccaat
1741 aatgaagagt cctttatcct ggatgctgac agcaacatgg gaaacagaat tgagagcatc
1801 actcagcgca tggcaataat agaaggaaag aataagcttc caccagctaa cagttctttc
1861 atgttgccac ctacaagctt ctcttccaac tacttccatt tccttccgtg a
```

Fig. 21

SEQ ID NO: 9

Met Glu Glu Gly Ala Pro Arg Gln Pro Gly Pro Ser Gln Trp Pro Pro

Glu Asp Glu Lys Glu Val Ile Arg Arg Ala Ile Gln Lys Glu Leu Lys

Ile Lys Glu Gly Val Glu Asn Leu Arg Arg Val Ala Thr Asp Arg Arg

His Leu Gly His Val Gln Gln Leu Leu Arg Ser Ser Asn Arg Arg Leu

Glu Gln Leu His Gly Glu Leu Arg Glu Leu His Ala Arg Ile Leu Leu

Pro Gly Pro Gly Pro Gly Pro Ala Glu Pro Val Ala Ser Gly Pro Arg

Pro Trp Ala Glu Gln Leu Arg Ala Arg His Leu Glu Ala Leu Arg Arg

Gln Leu His Val Glu Leu Lys Val Lys Gln Gly Ala Glu Asn Met Thr

His Thr Cys Ala Ser Gly Thr Pro Lys Glu Arg Lys Leu Leu Ala Ala

Ala Gln Gln Met Leu Arg Asp Ser Gln Leu Lys Val Ala Leu Leu Arg

Met Lys Ile Ser Ser Leu Glu Ala Ser Gly Ser Pro Glu Pro Gly Pro

Glu Leu Leu Ala Glu Glu Leu Gln His Arg Leu His Val Glu Ala Ala

Val Ala Glu Gly Ala Lys Asn Val Val Lys Leu Leu Ser Ser Arg Arg

Thr Gln Asp Arg Lys Ala Leu Ala Glu Ala Gln Ala Gln Leu Gln Glu

Ser Ser Gln Lys Leu Asp Leu Leu Arg Leu Ala Leu Glu Gln Leu Leu

Glu Gln Leu Pro Pro Ala His Pro Leu Arg Ser Arg Val Thr Arg Glu

Leu Arg Ala Ala Val Pro Gly Tyr Pro Gln Pro Ser Gly Thr Pro Val

Lys Pro Thr Ala Leu Thr Gly Thr Leu Gln Val Arg Leu Leu Gly Cys

Glu Gln Leu Leu Thr Ala Val Pro Gly Arg Ser Pro Ala Ala Ala Leu

Ala Ser Ser Pro Ser Glu Gly Trp Leu Arg Thr Lys Ala Lys His Gln

Arg Gly Arg Gly Glu Leu Ala Ser Glu Val Leu Ala Val Leu Lys Val

Asp Asn Arg Val Val Gly Gln Thr Gly Trp Gly Gln Val Ala Glu Gln

Ser Trp Asp Gln Thr Phe Val Ile Pro Leu Glu Arg Ala Arg Glu Leu

Glu Ile Gly Val His Trp Arg Asp Trp Arg Gln Leu Cys Gly Val Ala

Fig. 21 (continued)

Phe Leu Arg Leu Glu Asp Phe Leu Asp Asn Ala Cys His Gln Leu Ser

Leu Ser Leu Val Pro Gln Gly Leu Leu Phe Ala Gln Val Thr Phe Cys

Asp Pro Val Ile Glu Arg Arg Pro Arg Leu Gln Arg Gln Glu Arg Ile

Phe Ser Lys Arg Arg Gly Gln Asp Phe Leu Arg Arg Ser Gln Met Asn

Leu Gly Met Ala Ala Trp Gly Arg Leu Val Met Asn Leu Leu Pro Pro

Cys Ser Ser Pro Ser Thr Ile Ser Pro Pro Lys Gly Cys Pro Arg Thr

Pro Thr Thr Leu Arg Glu Ala Ser Asp Pro Ala Thr Pro Ser Asn Phe

Leu Pro Lys Lys Thr Pro Leu Gly Glu Glu Met Thr Pro Pro Pro Lys

Pro Pro Arg Leu Tyr Leu Pro Gln Glu Pro Thr Ser Glu Glu Thr Pro

Arg Thr Lys Arg Pro His Met Glu Pro Arg Thr Arg Arg Gly Pro Ser

Pro Pro Ala Ser Pro Thr Arg Lys Pro Pro Arg Leu Gln Asp Phe Arg

Cys Leu Ala Val Leu Gly Arg Gly His Phe Gly Lys Val Leu Leu Val

Gln Phe Lys Gly Thr Gly Lys Tyr Tyr Ala Ile Lys Ala Leu Lys Lys

Gln Glu Val Leu Ser Arg Asp Glu Ile Glu Ser Leu Tyr Cys Glu Lys

Arg Ile Leu Glu Ala Val Gly Cys Thr Gly His Pro Phe Leu Leu Ser

Leu Leu Val Cys Phe Gln Thr Ser Ser His Ala Arg Phe Val Thr Glu

Phe Val Pro Gly Gly Asp Leu Met Met Gln Ile His Glu Asp Val Phe

Pro Glu Pro Gln Ala Arg Phe Tyr Val Ala Cys Val Val Leu Gly Leu

Gln Phe Leu His Glu Lys Lys Ile Ile Tyr Arg Asp Leu Lys Leu Asp

Asn Leu Leu Leu Asp Ala Gln Gly Phe Leu Lys Ile Ala Asp Phe Gly

Leu Cys Lys Glu Gly Ile Gly Phe Gly Asp Arg Thr Ser Thr Phe Cys

Gly Thr Pro Glu Phe Leu Ala Pro Glu Val Leu Thr Gln Glu Ala Tyr

Thr Gln Ala Val Asp Trp Trp Ala Leu Gly Val Leu Leu Tyr Glu Met

Leu Val Gly Glu Cys Pro Phe Pro Gly Asp Thr Glu Glu Glu Val Phe

Asp Cys Ile Val Asn Met Asp Ala Pro Tyr Pro Gly Phe Leu Ser Val

Gln Gly Leu Glu Phe Ile Gln Lys Leu Leu Gln Lys Cys Pro Glu Lys

Fig. 21 (continued)

Arg Leu Gly Ala Gly Glu Gln Asp Ala Glu Glu Ile Lys Val Gln Pro

Phe Phe Arg Thr Thr Asn Trp Gln Ala Leu Leu Ala Arg Thr Ile Gln

Pro Pro Phe Val Pro Thr Leu Cys Gly Pro Ala Asp Leu Arg Tyr Phe

Glu Gly Glu Phe Thr Gly Leu Pro Pro Ala Leu Thr Pro Pro Ala Pro

His Ser Leu Leu Thr Ala Arg Gln Gln Ala Ala Phe Arg Asp Phe Asp

Phe Val Ser Glu Arg Phe Leu Glu Pro

Fig. 22

SEQ ID NO: 10

```
atggaggagg gggcgccgcg gcagcctggg ccgagccagt ggcccccaga ggatgagaag      60
gaggtgatcc gccgggccat ccagaaagag ctgaagatca aggagggggt ggagaacctg     120
cggcgcgtgg ccacagaccg ccgccacttg ggccatgtgc agcagctgct gcggtcctcc     180
aaccgccgcc tggagcagct gcatggcgag ctgcgggagc tgcacgcccg aatcctgctg     240
cccggccctg ggcctggccc agctgagcct gtggcctcag gaccccggcc gtgggcagag     300
cagctcaggg ctcggcacct agaggctctc cggaggcagc tgcatgtgga gctgaaggtg     360
aaacaggggg ctgagaacat gacccacacg tgcgccagtg gcacccccaa ggagaggaag     420
ctccttgcag ctgcccagca gatgctgcgg gacagccagc tgaaggtggc cctgctgcgg     480
atgaagatca gcagcctgga ggccagtggg tccccggagc cagggcctga gctactggcg     540
gaggagctac agcatcgact gcacgttgag gcagcggtgg ctgagggcgc caagaacgtg     600
gtgaaactgc ttagtagccg gagaacacag gaccgcaagg cactggctga ggcccaggcc     660
cagctacagg agtcctctca gaaactggac ctcctgcgcc tggccttgga gcagctgctg     720
gagcaactgc ctcctgccca ccctttgcgc agcagagtga cccgagagtt gcgggctgcg     780
gtgcctggat acccccagcc ttcagggaca cctgtgaagc ccaccgccct aacagggaca     840
ctgcaggtcc gcctcctggg ctgtgaacag ttgctgacag ccgtgcctgg gcgctcccca     900
gcggccgcac tggccagcag cccctccgag ggctggcttc ggaccaaggc caagcaccag     960
cgtggccgag gcgagcttgc cagtgaggtg ctggctgtgc taaaggtgga caaccgtgtt    1020
gtggggcaga cgggctgggg gcaggtggcc gaacagtcct gggaccagac ctttgtcatc    1080
ccactggagc gagcccgtga gctggagatt ggggtacact ggcgggactg gcggcagcta    1140
tgtggcgtgg ccttcctgag acttgaagac ttcctggaca atgcctgtca ccaactgtcc    1200
ctcagcctgg taccgcaggg actgcttttt gcccaggtga ccttctgcga tcctgtcatt    1260
gagaggcggc cccggctgca gaggcaggaa cgcatcttct ctaaacgcag aggccaggac    1320
ttcctgaggc gttcgcagat gaacctcggc atggcggcct gggggcgcct cgtcatgaac    1380
ctgctgcccc cctgcagctc cccgagcaca atcagccccc ctaaaggatg ccctcggacc    1440
ccaacaacac tgcgagaggc ctctgaccct gccactccca gtaatttcct gcccaagaag    1500
acccccttgg gtgaagagat gacaccccca cccaagcccc cacgcctcta cctcccccag    1560
gagccaacat ccgaggagac tccgcgcacc aaacgtcccc atatggagcc taggactcga    1620
```

Fig. 22 (continued)

```
cgtgggccat ctccaccagc ctcccccacc aggaaacccc ctcggcttca ggacttccgc   1680
tgcttagctg tgctgggccg gggacacttt gggaaggtcc tcctggtcca gttcaagggg   1740
acagggaaat actacgccat caaagcactg aagaagcagg aggtgctcag ccgggacgag   1800
atagagagcc tgtactgcga gaagcggatc ctggaggctg tgggctgcac agggcacccct  1860
ttcctgctct ccctccttgt ctgcttccag acctccagcc atgcccgctt tgtgactgag   1920
tttgtgcctg gtggtgacct catgatgcag atccacgagg atgtcttccc cgagccccag   1980
gcccgcttct acgtggcttg tgttgtcctg ggctgcagt tcttacacga gaagaagatc    2040
atttacaggg acctgaagtt ggataacctt ctgctggatg cccagggatt cctgaagatc   2100
gcagactttg gactctgcaa ggaagggatc ggcttcgggg accggactag caccttctgt   2160
ggcaccccgg agttcctggc tcccgaggtg ctgacccagg aggcatacac acaggccgtc   2220
gactggtggg cgctgggtgt gctgctctac gagatgctgg tgggtgagtg cccgttccca   2280
ggggacacag aggaagaggt gtttgactgc atcgtcaaca tggacgcccc ctaccccggc   2340
tttctgtcgg tgcaagggct tgagttcatt cagaagctcc tccagaagtg cccggagaag   2400
cgcctcgggg caggtgagca ggatgccgag gagatcaagg tccagccatt cttcaggacc   2460
accaactggc aagccctgct cgcccgcacc atccagcccc ccttcgtgcc taccctgtgt   2520
ggccctgcgg acctgcgcta ctttgagggc gagttcacag ggctgccgcc tgccctgacc   2580
ccacctgcac cccacagcct cctcactgcc cgccaacagg ccgccttccg ggacttcgac   2640
tttgtgtcag agcgattcct ggaaccctga                                   2670
```

USE OF VEGFR1 AS A BIOMARKER

The Sequence Listing for this application is labeled "29V9763.TXT" which was created on Jul. 19, 2013 and is 71 KB. The entire contents of the sequence listing is incorporated herein by reference in its entirety.

The present invention is related to the use of vascular endothelial growth factor receptor 1 (VEGFR1) or of a nucleic acid coding for VEGFR1 as a biomarker, a method for deciding whether a subject is a responder to a method of treatment, a method for deciding whether a subject having undergone a first method of treatment, wherein the first method of treatment comprises administering to the subject a PKN3 inhibitor, shall be subject to a second method of treatment, wherein the second method of treatment comprises administering to the subject a PKN3 inhibitor, a method for deciding whether a subject shall undergo a method of treatment, whereby the method of treatment comprises the administration of a PKN3 inhibitor, and a PKN3 inhibitor for use in a method for the treatment of a subject suffering from or being at risk of suffering from a disease.

Oncogenesis was described by Foulds (Foulds, L. (1958), *J Chronic Dis*, 8, 2-37) as a multistep biological process, which is presently known to occur by the accumulation of genetic damage. On a molecular level, the multistep process of tumorigenesis involves the disruption of both positive and negative regulatory effectors (Weinberg, R. A. (1989); Cancer Res, 49, 3713-3721). The molecular basis for human colon carcinomas has been postulated, by Vogelstein and coworkers (Fearon, E. R. and Vogelstein, B. (1990), Cell, 61, 759-767), to involve a number of oncogenes, tumor suppressor genes and repair genes. Similarly, defects leading to the development of retinoblastoma have been linked to another tumor suppressor gene (Lee, W. H., et al. (1987) Science, 235, 1394-1399). Still other oncogenes and tumor suppressors have been identified in a variety of other malignancies. Unfortunately, there remains an inadequate number of treatable cancers, and the effects of cancer are catastrophic—over half a million deaths per year in the United States alone.

Cancer is fundamentally a genetic disease in which damage to cellular DNA leads to disruption of the normal mechanisms that control cellular proliferation. Two of the mechanisms of action by which tumor suppressors maintain genomic integrity is by cell arrest, thereby allowing for repair of damaged DNA, or removal of the damaged DNA by apoptosis (Ellisen, L. W. and Haber, D. A. (1998), Annu Rev Med, 49, 425-436). Apoptosis, otherwise called "programmed cell death," is a carefully regulated network of biochemical events which act as a cellular suicide program aimed at removing irreversibly damaged cells. Apoptosis can be triggered in a number of ways including binding of tumor necrosis factor, DNA damage, withdrawal of growth factors, and antibody cross-linking of Fas receptors. Although several genes have been identified that play a role in the apoptotic process, the pathways leading to apoptosis have not been fully elucidated. Many investigators have attempted to identify novel apoptosis-promoting genes with the objective that such genes would afford a means to induce apoptosis selectively in neoplastic cells to treat lancer in a patient.

An alternative approach to treating cancer involves the suppression of angiogenesis with an agent such as Endostatin™ or anti-VEGF antibodies. In this approach, the objective is to prevent further vascularization of the primary tumor and potentially to constrain the size of metastatic lesions to that which can support neoplastic cell survival without substantial vascular growth.

A particular group of cancer diseases are those cancer diseases which are aggressive in terms of growth rate of the tumor, invasion into normal tissue, resistance to chemotherapy or other conventional treatments and the formation of metastasis throughout the body. In the case of more aggressive cancer, the cancer tissue is more different from the normal tissue and the tumor is more likely to spread. Therefore one objective in current cancer research is to develop agents which are inhibiting tumor growth and/or reducing the spreading of cancer cells throughout the body.

Definitions for what is an aggressive cancer disease may be taken from the homepage of the National Cancer Institute which is Worldwide Website: cancer.gov/Templates/db_alpha.aspx?CdrID=46053. Also, for the description of the aggressivity of a cancer disease, typically grading is used which is a system for classifying cancer cells in terms of how abnormal they appear when examined under a microscope. The objective of a grading system is to provide information about the probable growth rate of the tumor and its tendency to spread. The systems used to grade tumors vary with each type of cancer. Grading plays a role in treatment decisions.

Such grading systems are known to the ones skilled in the art. One of them is the Gleason score which is a system of grading prostate cancer tissue based on how it looks under a microscope. Gleason scores range from 2 to 10 and indicate how likely it is that a tumor will spread. A low Gleason score means the cancer tissue is similar to normal prostate tissue and the tumor is less likely to spread; a high Gleason score means the cancer tissue is very different from normal and the tumor is more likely to spread.

PKN3 which is also referred to as protein kinase N beta or PKN beta has been, among others, described by Oishi K, et al. (Oishi K. et al. *Biochem. Biophys. Res. Commun.* 261 (3): 808-14) or Shibata, H et al. (Shibata, H. et al.; *J. Biochem.* (Japan) 130 (1): 23-31). PKN3 has also been identified as a target molecule in tumors, in particular solid tumors, cancers, in particular metastatic cancers, and in pre-eclampsia. Also, as described in international patent application WO 2004/019973 protein kinase N beta is a downstream target of the PI-3 kinase/PTEN pathway which is linked to tumorigenesis and metastasis. Particularly the latter effect seems to be strongly related to the loss of suppressor function, more particularly PTEN tumour suppressor function.

The treatment of any disease is intended to provide relief or even cure to a patient while avoiding any undesired side effects or any adverse effects. In order to comply with this task there is a need for biomarkers which allow, in the broadest sense, to distinguish responders to a therapy from non-responders to such therapy. Furthermore, biomarkers are, for example, needed and useful as inclusion criterion for clinical trials, establishment or identification of optimum drug, dose and schedule of therapy and for identifying patients at high risk for adverse effects.

In the light of the above, there is a need for identifying biomarkers which can be used in the context of diseases and more specifically of diseases which can be treated by administering to a patient suffering from or being at risk of suffering from a disease which can be treated by a PKN3 inhibitor. Insofar, one problem underlying the present invention is the identification of such biomarkers.

A further problem underlying the present invention is the provision of a medicament for a particular group of patients suffering from or being at risk of suffering from a diseases which can be treated by administering to such patients a PKN3 inhibitor, whereby preferably such particular group of patients comprises a very high percentage of responders to such therapy comprising administering to the patients a PKN3 inhibitor.

These and further problems are solved by the subject matter of the attached independent claims. Particularly preferred embodiments may be taken from the attached dependent claims.

The problem underlying the present invention is also solved in a first aspect which is also the first embodiment of the first aspect by the use of VEGFR1 or of a nucleic acid coding for VEGFR1 as a biomarker in a method for the treatment of a subject, wherein the method for the treatment comprises administering to the subject a PKN3 inhibitor.

In a second embodiment of the first aspect which is also an embodiment of the first embodiment of the first aspect, the expression level of VEGFR1 or of a nucleic acid coding for VEGFR1 is a or the biomarker.

The problem underlying the present invention is also solved in a second aspect which is also the first embodiment of the second aspect by the use of VEGFR1 or of a nucleic acid coding for VEGFR1 as a biomarker in designing a method for the treatment of a subject, wherein the method for the treatment comprises administering to the subject a PKN3 inhibitor.

In a second embodiment of the second aspect which is also an embodiment of the first embodiment of the second aspect, the expression level of VEGFR1 or of a nucleic acid coding for VEGFR1 is a or the biomarker.

In a third embodiment of the first aspect which is also an embodiment of the first and the second embodiment of the first aspect, and in a third embodiment of the second aspect which is also an embodiment of the first and the second embodiment of the second aspect the VEGFR1 is selected from the group comprising VEGFR1 variant 2, VEGFR1 variant 1, VEGFR1 variant 3 and VEGFR1 variant 4.

In a fourth embodiment of the first aspect which is also an embodiment of the first, second and third embodiment of the first aspect, and in a fourth embodiment of the second aspect which is also an embodiment of the first, second and third embodiment of the second aspect the nucleic acid coding for VEGFR1 is selected from the group comprising VEGFR1 transcript variant 2, VEGFR1 transcript variant 1, VEGFR1 transcript variant 3 and VEGFR1 transcript variant 4.

In a fifth embodiment of the first aspect which is also an embodiment of the first, second, third and fourth embodiment of the first aspect, and in a fifth embodiment of the second aspect which is also an embodiment of the first, second, third and fourth embodiment of the second aspect the VEGFR1 is soluble VEGFR1 or VEGFR1 variant 2.

In a sixth embodiment of the first aspect which is also an embodiment of the fifth embodiment of the first aspect, and in a sixth embodiment of the second aspect which is also an embodiment of the fifth embodiment of the second aspect the soluble VEGFR1 or VEGFR1 variant 2 comprises an amino acid sequence according to SEQ ID NO:1 or is encoded by a nucleotide sequence according to SEQ ID NO: 2.

In a seventh embodiment of the first aspect which is also an embodiment of the first, second, third and fourth embodiment of the first aspect, and in a seventh embodiment of the second aspect which is also an embodiment of the first, second, third and fourth embodiment of the second aspect the nucleic acid coding for VEGFR1 is a nucleic acid coding for soluble VEGFR1 or VEGFR1 variant 2.

In an eighth embodiment of the first aspect which is also an embodiment of the seventh embodiment of the first aspect, and in an eighth embodiment of the second aspect which is also an embodiment of the seventh embodiment of the second aspect the nucleic acid coding for soluble VEGFR1 or VEGFR1 variant 2 comprises a nucleotide sequence according to SEQ ID NO:2 or a nucleotide sequence encoding an amino acid sequence according to SEQ ID NO: 1.

In a ninth embodiment of the first aspect which is also an embodiment of the first, second, third and fourth embodiment of the first aspect, and in a ninth embodiment of the second aspect which is also an embodiment of the first, second, third and fourth embodiment of the second aspect the VEGFR1 is VEGFR1 variant 1.

In a tenth embodiment of the first aspect which is also an embodiment of the ninth embodiment of the first aspect, and in a tenth embodiment of the second aspect which is also an embodiment of the ninth embodiment of the second aspect the VEGFR1 variant 1 comprises an amino acid sequence according to SEQ ID NO: 3 or is encoded by a nucleotide sequence according to SEQ ID NO: 4.

In an eleventh embodiment of the first aspect which is also an embodiment of the first, second, third and fourth embodiment of the first aspect, and in an eleventh embodiment of the second aspect which is also an embodiment of the first, second, third and fourth embodiment of the second aspect the nucleic acid coding for VEGFR1 is a nucleic acid coding for VEGFR1 variant 1.

In a twelfth embodiment of the first aspect which is also an embodiment of the eleventh embodiment of the first aspect, and in a twelfth embodiment of the second aspect which is also an embodiment of the eleventh embodiment of the second aspect the nucleic acid coding for VEGFR1 variant 1 comprises a nucleotide sequence according to SEQ ID NO: 4 or a nucleotide sequence encoding an amino acid sequence according to SEQ ID NO: 3.

In a 13$^{th}$ embodiment of the first aspect which is also an embodiment of the first, second, third and fourth embodiment of the first aspect, and in a 13$^{th}$ embodiment of the second aspect which is also an embodiment of the first, second, third and fourth embodiment of the second aspect the VEGFR1 is VEGFR1 variant 3.

In a 14$^{th}$ embodiment of the first aspect which is also an embodiment of the 13$^{th}$ embodiment of the first aspect, and in a 14$^{th}$ embodiment of the second aspect which is also an embodiment of the 13$^{th}$ embodiment of the second aspect the VEGFR1 variant 3 comprises an amino acid sequence according to SEQ ID NO: 5 or is encoded by a nucleotide sequence according to SEQ ID NO: 6.

In a 15$^{th}$ embodiment of the first aspect which is also an embodiment of the first, second, third and fourth embodiment of the first aspect, and in a 15$^{th}$ embodiment of the second aspect which is also an embodiment of the first, second, third and fourth embodiment of the second aspect the nucleic acid coding for VEGFR1 is a nucleic acid coding for VEGFR1 variant 3.

In a 16$^{th}$ embodiment of the first aspect which is also an embodiment of the 15$^{th}$ embodiment of the first aspect, and in a 16$^{th}$ embodiment of the second aspect which is also an embodiment of the 15$^{th}$ embodiment of the second aspect the nucleic acid coding for VEGFR1 variant 3 comprises a nucleotide sequence according to SEQ ID NO: 6 or a nucleotide sequence encoding an amino acid sequence according to SEQ ID NO: 5.

In a 17$^{th}$ embodiment of the first aspect which is also an embodiment of the first, second, third and fourth embodiment of the first aspect, and in a 17$^{th}$ embodiment of the second aspect which is also an embodiment of the first, second, third and fourth embodiment of the second aspect the VEGFR1 is VEGFR1 variant 4.

In an 18$^{th}$ embodiment of the first aspect which is also an embodiment of the 17$^{th}$ embodiment of the first aspect, and in an 18$^{th}$ embodiment of the second aspect which is also an embodiment of the 17$^{th}$ embodiment of the second aspect the VEGFR1 variant 4 comprises an amino acid sequence according to SEQ ID NO: 7 or is encoded by a nucleotide sequence according to SEQ ID NO: 8.

In a 19$^{th}$ embodiment of the first aspect which is also an embodiment of the first, second, third and fourth embodiment of the first aspect, and in a 19$^{th}$ embodiment of the second aspect which is also an embodiment of the first, second, third and fourth embodiment of the second aspect the nucleic acid coding for VEGFR1 is a nucleic acid coding for VEGFR1 variant 4.

In a 20$^{th}$ embodiment of the first aspect which is also an embodiment of the 19$^{th}$ embodiment of the first aspect, and in a 20$^{th}$ embodiment of the second aspect which is also an embodiment of the 19$^{th}$ embodiment of the second aspect the nucleic acid coding for VEGFR1 variant 4 comprises a nucleotide sequence according to SEQ ID NO: 8 or a nucleotide sequence encoding an amino acid sequence according to SEQ ID NO: 7.

In a 21$^{st}$ embodiment of the first aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the first aspect, and in a 21$^{st}$ embodiment of the second aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the second aspect the biomarker is a pharmacodynamic biomarker.

In a 22$^{nd}$ embodiment of the first aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the first aspect, and in a 22$^{nd}$ embodiment of the second aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the second aspect the biomarker is a predictive biomarker.

In a 23$^{rd}$ embodiment of the first aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the first aspect, and in a 23$^{rd}$ embodiment of the second aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the second aspect the biomarker is a prognostic biomarker.

In a 24$^{th}$ embodiment of the first aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the first aspect, and in a 24$^{th}$ embodiment of the second aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$ embodiment of the second aspect the biomarker is a surrogate biomarker.

In a 25$^{th}$ embodiment of the first aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$ and 24$^{th}$ embodiment of the first aspect, and in a 25$^{th}$ embodiment of the second aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$ and 20$^{th}$, 21$^{st}$, 22$^{nd}$, 23$^{rd}$ and 24$^{th}$ embodiment of the second aspect the subject is suffering from or at risk of suffering from a disease, wherein the disease is a disease which can be treated, ameliorated and/or cured by a PKN3 inhibitor.

In a 26$^{th}$ embodiment of the first aspect which is also an embodiment of the 25$^{th}$ embodiment of the first aspect, and in a 26$^{th}$ embodiment of the second aspect which is also an embodiment of the 25$^{th}$ embodiment of the second aspect the disease is selected from the group comprising tumor diseases, cancer diseases and pre-eclampsia.

In a 27$^{th}$ embodiment of the first aspect which is also an embodiment of the 25$^{th}$ and 26$^{th}$ embodiment of the first aspect, and in a 27$^{th}$ embodiment of the second aspect which is also an embodiment of the 25$^{th}$ and 26$^{th}$ embodiment of the second aspect the disease is selected from the group comprising lung cancer, pancreas cancer, liver cancer, endometrial cancer, colorectal carcinomas, gliomas, adenocarcinomas, endometrial hyperplasias, hereditary non-polyposis colorectal carcinoma, breast-ovarian cancer, prostate cancer, gastrointestinal harmatomas, lipomas, thyroid adenomas, fibrocystic disease of the breast, cerebellar dysplastic gangliocytoma, breast and thyroid malignancies, large cell carcinoma, small cell carcinoma and squamous cell carcinoma.

In a 28$^{th}$ embodiment of the first aspect which is also an embodiment of the 25$^{th}$ and 26$^{th}$ embodiment of the first aspect, and in a 28$^{th}$ embodiment of the second aspect which is also an embodiment of the 25$^{th}$ and 26$^{th}$ embodiment of the second aspect the disease is a disease is selected from the group comprising cancers, metastatic cancers and any pathological conditions involving the PI 3-kinase pathway.

In a 29$^{th}$ embodiment of the first aspect which is also an embodiment of the 25$^{th}$ and 26$^{th}$ embodiment of the first aspect, and in a 29$^{th}$ embodiment of the second aspect which is also an embodiment of the 25$^{th}$ and 26$^{th}$ embodiment of the second aspect the disease is characterized in that the cells being involved in said disease lack PTEN activity, show an increased aggressive behavior, or are cells of a late stage tumor.

In a 30$^{th}$ embodiment of the first aspect which is also an embodiment of the 25$^{th}$ and 26$^{th}$ embodiment of the first aspect, and in a 30$^{th}$ embodiment of the second aspect which is also an embodiment of the 25$^{th}$ and 26$^{th}$ embodiment of the second aspect the disease is selected from the group comprising metastatic cancers and any pathological conditions involving the PI 3-kinase pathway, whereby such pathological condition consists of endometrial cancer, colorectal carcinomas, gliomas, adenocarcinomas, endometrial hyperplasias, Cowden's syndrome, hereditary non-polyposis colorectal carcinoma, Li-Fraumene's syndrome, breast-ovarian cancer, prostate cancer, Bannayan-Zonana syndrome, LDD (Lhermitte-Duklos' syndrome) hamartoma-macrocephaly diseases including Cow disease (CD) and Bannayan-Ruvalcaba-Rily syndrome (BRR), mucocutaneous lesions such as trichilemmonmas, macrocephaly, mental retardation, gastrointestinal harmatomas, lipomas, thyroid adenomas, fibrocystic disease of the breast, cerebellar dysplastic gangliocytoma, and breast and thyroid malignancies and large cell carcinoma, small cell carcinoma and squamous cell carcinoma.

In a 31$^{st}$ embodiment of the first aspect which is also an embodiment of the first, second, third, fourth, fifth, sixth, seventh, eighth, ninth tenth, eleventh, twelfth, 13$^{th}$, 14$^{th}$, 15$^{th}$, 16$^{th}$, 17$^{th}$, 18$^{th}$, 19$^{th}$, 20$^{th}$, 21$^{st}$, 22$^{nd}$, 23$^{rd}$, 24$^{th}$, 25$^{th}$, 26$^{th}$, 27$^{th}$, 28$^{th}$, 29$^{th}$ and 30$^{th}$ embodiment of the first aspect, and in a 31$^{st}$ embodiment of the second aspect which is also an embodiment of the first, second, third, fourth, fifth, sixth, seventh, eighth, ninth tenth, eleventh, twelfth, 13$^{th}$, 14$^{th}$, 15$^{th}$, 16th, 17th, 18th, 19th, 20th, 21st, 22nd, 23rd, 24th, 25th, 26th, 27th, 28th, 29th and 30th embodiment of the second aspect the PKN3 inhibitor is selected from the group comprising an siRNA directed against an mRNA coding for PKN3, an antisense oligonucleotide directed against an mRNA coding for PKN3, a ribozyme directed against an mRNA coding for PKN3, an shRNA directed against an mRNA coding for PKN3, an miRNA or antagomir directed against an mRNA coding for PKN3, an aptamer directed against PKN3, a spiegelmer directed against PKN3, an antibody directed against PKN3, an anticalin directed against PKN3, and a small molecule.

In a 32nd embodiment of the first aspect which is also an embodiment of the first, second, third, fourth, fifth, sixth, seventh, eighth, ninth tenth, eleventh, twelfth, 13th, 14th, 15th, 16th, 17th, 18th, 19th, 20th, 21st, 22nd, 23rd, 24th, 25th, 26th, 27th, 28th, 29th, 30th and 31st embodiment of the first aspect, and in a 32nd embodiment of the second aspect which is also an embodiment of the first, second, third, fourth, fifth, sixth, seventh, eighth, ninth tenth, eleventh, twelfth, 13th, 14th, 15th, 16th, 17th, 18th, 19th, 20th, 21st, 22nd, 23rd, 24th, 25th, 26th, 27th, 28th, 29th, 30th and 31st embodiment of the second aspect the PKN3 inhibitor is an siRNA wherein the siRNA is as follows:

```
                                    (SEQ ID NO: 11)
5' 5u8u7c6g8a6g5c7u7a6g5c5 3'

                                    (SEQ ID NO: 12)
3' a6c6g8u7c5u7a8g6g5u7a8a 5'
```

with unmodified ribonucleotides being as indicated and modified ribonucleotides being represented as follows:

5: 2'-O-Methyl-u,

6: 2'-O-Methyl-a,

7: 2'-O-Methyl-c,

8: 2'-O-Methyl-g.

In a 33rd embodiment of the first aspect which is also an embodiment of the first, second, third, fourth, fifth, sixth, seventh, eighth, ninth tenth, eleventh, twelfth, 13th, 14th, 15th, 16th, 17th, 18th, 19th, 20th, 21st, 22nd, 23rd, 24th, 25th, 26th, 27th, 28th, 29th and 30th, 31st and 32nd embodiment of the first aspect, and in a 33rd embodiment of the second aspect which is also an embodiment of the first, second, third, fourth, fifth, sixth, seventh, eighth, ninth tenth, eleventh, twelfth, 13th, 14th, 15th, 16th, 17th, 18th, 19th, 20th, 21st, 22nd, 23rd, 24th, 25th, 26th, 27th, 28th, 29th and 30th, 31st and 32nd embodiment of the second aspect PKN3 comprises an amino acid sequence according to SEQ ID NO: 9.

In a 34th embodiment of the first aspect which is also an embodiment of the first, second, third, fourth, fifth, sixth, seventh, eighth, ninth tenth, eleventh, twelfth, 13th, 14th, 15th, 16th, 17th, 18th, 19th, 20th, 21st, 22nd, 23rd, 24th, 25th, 26th, 27th, 28th, 29th and 30th, 31st and 32nd embodiment of the first aspect, and in a 34th embodiment of the second aspect which is also an embodiment of the first, second, third, fourth, fifth, sixth, seventh, eighth, ninth tenth, eleventh, twelfth, 13th, 14th, 15th, 16th, 17th, 18th, 19th, 20th, 21st, 22nd, 23rd, 24th, 25th, 26th, 27th, 28th, 29th and 30th, 31st and 32nd embodiment of the second aspect PKN3 is encoded by a nucleotide sequence according to SEQ ID NO: 10 or a nucleotide sequence coding for an amino acid sequence according to SEQ ID NO: 9.

Additional non-limiting embodiments provide:

1. Use of VEGFR1 or of a nucleic acid coding for VEGFR1 as a biomarker in a method for the treatment of a subject, wherein the method for the treatment comprises administering to the subject a PKN3 inhibitor.

2. Use according to embodiment 1, wherein the expression level of VEGFR1 or of a nucleic acid coding for VEGFR1 is a or the biomarker.

3. Use of VEGFR1 or of a nucleic acid coding for VEGFR1 as a biomarker in designing a method for the treatment of a subject, wherein the method for the treatment comprises administering to the subject a PKN3 inhibitor.

4. Use according to embodiment 3, wherein the expression level of VEGFR1 or of a nucleic acid coding for VEGFR1 is a or the biomarker.

5. Use according to any one of embodiments 1 to 4, wherein the VEGFR1 is selected from the group comprising VEGFR1 variant 2, VEGFR1 variant 1, VEGFR1 variant 3 and VEGFR1 variant 4.

6. Use according to any one of embodiments 1 to 4, wherein the nucleic acid coding for VEGFR1 is selected from the group comprising VEGFR1 transcript variant 2, VEGFR1 transcript variant 1, VEGFR1 transcript variant 3 and VEGFR1 transcript variant 4.

7. Use according to any one of embodiments 1 to 6, wherein the VEGFR1 is soluble VEGFR1 or VEGFR1 variant 2.

8. Use according to embodiment 7, wherein the soluble VEGFR1 or VEGFR1 variant 2 comprises an amino acid sequence according to SEQ ID NO:1 or is encoded by a nucleotide sequence according to SEQ ID NO: 2.

9. Use according to any one of embodiments 1 to 6, wherein the nucleic acid coding for VEGFR1 is a nucleic acid coding for soluble VEGFR1 or VEGFR1 variant 2.

10. Use according to embodiment 9, wherein the nucleic acid coding for soluble VEGFR1 or VEGFR1 variant 2 comprises a nucleotide sequence according to SEQ ID NO:2 or a nucleotide sequence encoding an amino acid sequence according to SEQ ID NO: 1.

11. Use according to any one of embodiments 1 to 6, wherein the VEGFR1 is VEGFR1 variant 1.

12. Use according to embodiment 11, wherein the VEGFR1 variant 1 comprises an amino acid sequence according to SEQ ID NO: 3 or is encoded by a nucleotide sequence according to SEQ ID NO: 4.

13. Use according to any one of embodiments 1 to 6, wherein the nucleic acid coding for VEGFR1 is a nucleic acid coding for VEGFR1 variant 1.

14. Use according to embodiment 13, wherein the nucleic acid coding for VEGFR1 variant 1 comprises a nucleotide sequence according to SEQ ID NO: 4 or a nucleotide sequence encoding an amino acid sequence according to SEQ ID NO: 3.

15. Use according to any one of embodiments 1 to 6, wherein the VEGFR1 is VEGFR1 variant 3.

16. Use according to embodiment 15, wherein the VEGFR1 variant 3 comprises an amino acid sequence according to SEQ ID NO: 5 or is encoded by a nucleotide sequence according to SEQ ID NO: 6.

17. Use according to any one of embodiments 1 to 6, wherein the nucleic acid coding for VEGFR1 is a nucleic acid coding for VEGFR1 variant 3.

18. Use according to embodiment 17, wherein the nucleic acid coding for VEGFR1 variant 3 comprises a nucleotide sequence according to SEQ ID NO: 6 or a nucleotide sequence encoding an amino acid sequence according to SEQ ID NO: 5.

19. Use according to any one of embodiments 1 to 6, wherein the VEGFR1 is VEGFR1 variant 4.

20. Use according to embodiment 19, wherein the VEGFR1 variant 4 comprises an amino acid sequence according to SEQ ID NO: 7 or is encoded by a nucleotide sequence according to SEQ ID NO: 8.

21. Use according to any one of embodiments 1 to 6, wherein the nucleic acid coding for VEGFR1 is a nucleic acid coding for VEGFR1 variant 4.

22. Use according to embodiment 21, wherein the nucleic acid coding for VEGFR1 variant 4 comprises a nucleotide sequence according to SEQ ID NO: 8 or a nucleotide sequence encoding an amino acid sequence according to SEQ ID NO: 7.

23. Use according to any one of embodiments 1 to 22, wherein the biomarker is a pharmacodynamic biomarker.

24. Use according to any one of embodiments 1 to 22, wherein the biomarker is a predictive biomarker.

25. Use according to any one of embodiments 1 to 22, wherein the biomarker is a prognostic biomarker.

26. Use according to any one of embodiments 1 to 22, wherein the biomarker is a surrogate biomarker.

27. Use according to any one of embodiments 1 to 26, wherein the subject is suffering from or at risk of suffering from a disease, wherein the disease is a disease which can be treated, ameliorated and/or cured by a PKN3 inhibitor.

28. Use according to embodiment 27, wherein the disease is selected from the group comprising tumor diseases, cancer diseases and pre-eclampsia.

29. Use according to any one of embodiments 27 to 28, wherein the disease is selected from the group comprising lung cancer, pancreas cancer, liver cancer, endometrial cancer, colorectal carcinomas, gliomas, adenocarcinomas, endometrial hyperplasias, hereditary non-polyposis colorectal carcinoma, breast-ovarian cancer, prostate cancer, gastrointestinal harmatomas, lipomas, thyroid adenomas, fibrocystic disease of the breast, cerebellar dysplastic gangliocytoma, breast and thyroid malignancies, large cell carcinoma, small cell carcinoma and squamous cell carcinoma.

30. Use according to any one of embodiments 27 to 28, wherein the disease is a disease is selected from the group comprising cancers, metastatic cancers and any pathological conditions involving the PI 3-kinase pathway.

31. Use according to any one of embodiments 27 to 28, wherein the disease is characterized in that the cells being involved in said disease lack PTEN activity, show an increased aggressive behavior, or are cells of a late stage tumor.

32. Use according to any one of embodiments 27 to 28, wherein the disease is selected from the group comprising metastatic cancers and any pathological conditions involving the PI 3-kinase pathway, whereby such pathological condition consists of endometrial cancer, colorectal carcinomas, gliomas, adenocarcinomas, endometrial hyperplasias, Cowden's syndrome, hereditary non-polyposis colorectal carcinoma, Li-Fraumene's syndrome, breast-ovarian cancer, prostate cancer, Bannayan-Zonana syndrome, LDD (Lhermitte-Duklos' syndrome) hamartoma-macrocephaly diseases including Cow disease (CD) and Bannayan-Ruvalcaba-Rily syndrome (BRR), mucocutaneous lesions such as trichilemmonmas, macrocephaly, mental retardation, gastrointestinal harmatomas, lipomas, thyroid adenomas, fibrocystic disease of the breast, cerebellar dysplastic gangliocytoma, and breast and thyroid malignancies and large cell carcinoma, small cell carcinoma and squamous cell carcinoma.

33. Use according to any one of embodiments 1 to 32, wherein the PKN3 inhibitor selected from the group comprising an siRNA directed against an mRNA coding for PKN3, an antisense oligonucleotide directed against an mRNA coding for PKN3, a ribozyme directed against an mRNA coding for PKN3, an shRNA directed against an mRNA coding for PKN3, an miRNA or antagomir directed against an mRNA coding for PKN3, an aptamer directed against PKN3, a spiegelmer directed against PKN3, an antibody directed against PKN3, an anticalin directed against PKN3, and a small molecule.

34. Use according to any one of embodiments 1 to 33, wherein the PKN3 inhibitor is an siRNA wherein the siRNA is as follows:

```
                                   (SEQ ID NO: 11)
5' 5u8u7c6g8a6g5c7u7a6g5c5 3'

                                   (SEQ ID NO: 12)
3' a6c6g8u7c5u7a8g6g5u7a8a 5'
```

with unmodified ribonucleotides being as indicated and modified ribonucleotides being represented as follows:

5: 2'-O-Methyl-u,
6: 2'-O-Methyl-a,
7: 2'-O-Methyl-c,
8: 2'-O-Methyl-g.

35. Use according to any one of embodiments 1 to 34, wherein PKN3 comprises an amino acid sequence according to SEQ ID NO: 9.

36. Use according to any one of embodiments 1 to 34, wherein PKN3 is encoded by a nucleotide sequence according to SEQ ID NO: 10 or a nucleotide sequence coding for an amino acid sequence according to SEQ ID NO: 9.

37. A method for deciding whether a subject is a responder to a method of treatment, wherein the method of treatment comprises administering to the subject a PKN3 inhibitor, comprising:

determining the level of VEGFR1 or of a nucleic acid coding for VEGFR1 in a sample from the subject prior to the subject being subjected to the method of treatment, determining the level of VEGFR1 or of a nucleic acid coding for VEGFR1 in a sample from the subject after the subject having been subjected to the method of treatment; wherein if the level of VEGFR1 or a nucleic acid coding for VEGFR1 in a sample from the subject after the subject having been subjected to the method of treatment is decreased compared to the level of VEGFR1 or a nucleic acid coding for VEGFR1 in a sample from the subject prior to the subject having being subjected to the method of treatment, the subject is a responder to the method of treatment.

38. The method according to embodiment 37, wherein the decrease is a decrease of 10% or more, of 20% or more, 40% or more, 60% or more or 80% or more.

39. The method according to any one of embodiments 37 to 38, wherein the subject is suffering from a disease or is at risk of suffering from a disease and wherein the method of treatment is a method of treatment for the disease.

40. A method for deciding whether a subject having undergone a first method of treatment, wherein the first method of treatment comprises administering to the subject a PKN3 inhibitor, shall be subject to a second method of treatment, wherein the second method of treatment comprises administering to the subject a PKN3 inhibitor, comprising:

determining the level of VEGFR1 or of a nucleic acid coding for VEGFR1 in a sample from the subject prior to a first method of treatment, determining the level of VEGFR1 or of a nucleic acid coding for VEGFR1 in a sample from the subject after a first period of time after the first method of treatment, and optionally determining the level of VEGFR1 or of a nucleic acid coding for VEGFR1 in a sample from the subject after a second period of time after the first method of treatment, wherein if the level of VEGFR1 or of a nucleic acid coding for VEGFR1 in a sample from the subject after the first or second period of time after the first method of treatment is increased compared to the level of VEGFR1 or of a nucleic acid coding for VEGFR1 in a sample from the subject prior to a first method of treatment, the subject is to be subjected to the second method of treatment.

41. The method according to embodiment 40, wherein the increase is 100% or more, 80% or more, 60% or more or 40% or more.

42. The method according to any one of embodiments 40 to 41, wherein the subject is suffering from a disease or is at risk of suffering from a disease and wherein the method of treatment is a method of treatment for the disease.

43. The method according to any one of embodiments 40 to 41, wherein first period of time after the first method of treatment is about 24 hours or 48 hours after the last administration of the PKN3 inhibitor being part of the first method of treatment.

44. The method according to any of embodiments 40 to 41, wherein the second period of time after the first method of treatment starts about 1 or two months after the first period of time after the first method of treatment.

45. The method according to any one of embodiments 40 to 44, wherein the first method of treatment is the same as the second method of treatment, or wherein the first method of treatment is different from the second method of treatment.

46. A method for deciding whether a subject shall undergo a method of treatment, whereby the method of treatment comprises the administration of a PKN3 inhibitor, comprising determining the level of VEGFR1 or of a nucleic acid coding for VEGFR1, or determining the expression level of VEGFR1 or of a nucleic acid coding for VEGFR1, wherein if the expression level of VEGFR1 or of a nucleic acid coding for VEGFR1, expressed as titre of VEGF1 in blood or plasma of the subject, is equal to or greater than 200 pg/ml, the patient is amenable to the method of treatment comprising administration of a PKN3 inhibitor.

47. The method according to embodiment 46, wherein if the expression level of VEGFR1 or of a nucleic acid coding for VEGFR1, expressed as titre of VEGF1 in blood or plasma of the subject, is equal to or greater than 400 pg/ml, preferably equal to or greater than 600 pg/ml, more preferably equal to or greater than 800 pg/ml, the patient is amenable to the method of treatment comprising administration of a PKN3 inhibitor.

48. The method according to any one of embodiments 37 to 47, wherein the disease is any disease as defined in any of the preceding embodiments.

49. The method according to any one of embodiments 37 to 48, wherein the PKN3 inhibitor is any PKN3 inhibitor as defined in any of the preceding embodiments.

50. The method according to any one of embodiments 37 to 49, wherein the VEGFR1 or a nucleic acid coding thereof is any VEGFR1 or a nucleic acid coding for the VEGFR1 as defined in any of the preceding embodiments.

51. A PKN3 inhibitor for use in a method for the treatment of a subject suffering from or being at risk of suffering from a disease, wherein the expression level of VEGFR1 or of a nucleic acid coding for VEGFR1, expressed as titre of VEGF1 in blood or plasma of the subject, is equal to or greater than 200 pg/ml.

52. The PKN3 inhibitor according to embodiment 51, wherein the expression level of VEGFR1 or of a nucleic acid coding for VEGFR1, expressed as titre of VEGF1 in blood or plasma of the subject, is equal to or greater than 400 pg/ml, preferably equal to or greater than 600 pg/ml and more preferably equal to or greater than 800 pg/ml.

The problem underlying the present invention is also solved in a third aspect which is also the first embodiment of the third aspect by a method for deciding whether a subject is a responder to a method of treatment, wherein the method of treatment comprises administering to the subject a PKN3 inhibitor, comprising:

determining the level of VEGFR1 or of a nucleic acid coding for VEGFR1 in a sample from the subject prior to the subject being subjected to the method of treatment, determining the level of VEGFR1 or of a nucleic acid coding for VEGFR1 in a sample from the subject after the subject having been subjected to the method of treatment;

wherein if the level of VEGFR1 or a nucleic acid coding for VEGFR1 in a sample from the subject after the subject having been subjected to the method of treatment is decreased compared to the level of VEGFR1 or a nucleic acid coding for VEGFR1 in a sample from the subject prior to the subject having being subjected to the method of treatment, the subject is a responder to the method of treatment.

In a second embodiment of the third aspect which is also an embodiment of the first embodiment of the third aspect, the decrease is a decrease of 10% or more, of 20% or more, 40% or more, 60% or more or 80% or more.

In a third embodiment of the third aspect which is also an embodiment of the first and the second embodiment of the third aspect, the subject is suffering from a disease or is at risk of suffering from a disease and wherein the method of treatment is a method of treatment for the disease.

The problem underlying the present invention is also solved in a fourth aspect which is also the first embodiment of the fourth aspect by a method for deciding whether a subject having undergone a first method of treatment, wherein the first method of treatment comprises administering to the subject a PKN3 inhibitor, shall be subject to a second method of treatment, wherein the second method of treatment comprises administering to the subject a PKN3 inhibitor, comprising:

determining the level of VEGFR1 or of a nucleic acid coding for VEGFR1 in a sample from the subject prior to a first method of treatment, determining the level of VEGFR1 or of a nucleic acid coding for VEGFR1 in a sample from the subject after a first period of time after the first method of treatment, and optionally determining the level of VEGFR1 or of a nucleic acid coding for VEGFR1 in a sample from the subject after a second period of time after the first method of treatment, wherein if the level of VEGFR1 or of a nucleic acid coding for VEGFR1 in a sample from the subject after the first or second period of time after the first method of treatment is increased compared to the level of VEGFR1 or of a nucleic acid coding for VEGFR1 in a sample from the subject prior to a first method of treatment, the subject is to be subjected to the second method of treatment.

In a second embodiment of the fourth aspect which is also an embodiment of the first embodiment of the fourth aspect, the increase is 100% or more, 80% or more, 60% or more or 40% or more.

In a third embodiment of the fourth aspect which is also an embodiment of the first and the second embodiment of the fourth aspect, the subject is suffering from a disease or is at risk of suffering from a disease and wherein the method of treatment is a method of treatment for the disease.

In a fourth embodiment of the fourth aspect which is also an embodiment of the first, second and third embodiment of the fourth aspect, the first period of time after the first method of treatment is about 24 hours or 48 hours after the last administration of the PKN3 inhibitor being part of the first method of treatment.

In a fifth embodiment of the fourth aspect which is also an embodiment of the first, second and third embodiment of the fourth aspect, the second period of time after the first method of treatment starts about 1 or two months after the first period of time after the first method of treatment.

In a sixth embodiment of the fourth aspect which is also an embodiment of the first, second, third, fourth and fifth embodiment of the fourth aspect, the first method of treatment is the same as the second method of treatment, or wherein the first method of treatment is different from the second method of treatment.

The problem underlying the present invention is also solved in a fifth aspect which is also the first embodiment of the fifth aspect by a method for deciding whether a subject shall undergo a method of treatment, whereby the method of treatment comprises the administration of a PKN3 inhibitor, comprising determining the level of VEGFR1 or of a nucleic acid coding for VEGFR1, or determining the expression level of VEGFR1 or of a nucleic acid coding for VEGFR1, wherein if the expression level of VEGFR1 or of a nucleic acid coding for VEGFR1, expressed as titre of VEGF1 in blood or plasma of the subject, is equal to or greater than 200 pg/ml, the patient is amenable to the method of treatment comprising administration of a PKN3 inhibitor.

In a second embodiment of the fifth aspect which is also an embodiment of the first embodiment of the fifth aspect, if the expression level of VEGFR1 or of a nucleic acid coding for VEGFR1, expressed as titre of VEGF1 in blood or plasma of the subject, is equal to or greater than 400 pg/ml, preferably equal to or greater than 600 pg/ml, more preferably equal to or greater than 800 pg/ml, the patient is amenable to the method of treatment comprising administration of a PKN3 inhibitor.

In an embodiment of any embodiment of the third, fourth and fifth aspect the disease is any disease as defined in any of the embodiments of any aspect of the present invention.

In an embodiment of any embodiment of the third, fourth and fifth aspect the PKN3 inhibitor is any PKN3 inhibitor as defined in any of the embodiments of any aspect of the present invention.

In an embodiment of any embodiment of the third, fourth and fifth aspect the VEGFR1 or a nucleic acid coding thereof is any VEGFR1 or a nucleic acid coding for the VEGFR1 as defined in any of the embodiments of any aspect of the present invention.

The problem underlying the present invention is also solved in a sixth aspect which is also the first embodiment of the sixth aspect by a PKN3 inhibitor for use in a method for the treatment of a subject suffering from or being at risk of suffering from a disease, wherein the expression level of VEGFR1 or of a nucleic acid coding for VEGFR1, expressed as titre of VEGF1 in blood or plasma of the subject, is equal to or greater than 200 pg/ml.

In a second embodiment of the sixth aspect which is also an embodiment of the sixth embodiment of the second aspect, the expression level of VEGFR1 or of a nucleic acid coding for VEGFR1, expressed as titre of VEGF1 in blood or plasma of the subject, is equal to or greater than 400 pg/ml, preferably equal to or greater than 600 pg/ml and more preferably equal to or greater than 800 pg/ml.

The present invention, in its various aspects, is based on the surprising finding that VEGFR1 or a nucleic acid coding for VEGFR1, i.e. VEGF receptor 1 which is also referred to as Flt-1, is a biomarker for therapies which are different from antiangiogenic therapy. More specifically, the present invention is based on the surprising finding that VEGFR1 is a biomarker in connection with methods for the treatment of a subject, wherein the method for the treatment comprises administering to the subject a PKN3 inhibitor. Based on this finding it is also within the present invention that VEGFR1 or a nucleic acid coding therefor are used as a biomarker in a method for the treatment of a subject or in connection with designing a method for the treatment of a subject, wherein the method for the treatment comprises administering to the subject a PKN3 inhibitor. Such designing may comprise, among other, at least one of the following: Identifying responders from non-responders to the method for the treatment comprising administering a PKN3 inhibitor, defining the establishment or identification of optimum drug, dose and schedule of such method for the treatment and for identifying patients at high risk for adverse effects in connection with such method for the treatment.

As preferably used herein, a method for the treatment means a therapy and a method for the treatment comprising administration to a subject a PKN3 inhibitor means an anti-PKN3 therapy.

As preferably used herein, a PKN3 inhibitor is a compound which addresses or targets PKN3 or a fragment thereof, whereby the targeting of PKN3 or a fragment thereof results in a therapeutic effect in a subject to which the PKN3 inhibitor is administered.

A subject as preferably used is a vertebrate, more preferably a mammal. A particular preferred subject is man.

It will be understood by a person skilled in the art that the use of VEGFR1 or of a nucleic acid coding for VEGFR1 as a biomarker can be realized or put into practice by using or referring to the expression level of VEGFR1 or the expression level of a nucleic acid coding for VEGFR1. Insofar, the present invention in its various aspects also relates to the use of the expression level of VEGFR1 or of a nucleic acid coding for VEGFR1 as a biomarker in a method for the treatment of a subject, wherein the method for the treatment comprises administering to the subject a PKN3 inhibitor, and to the use of the expression level of VEGFR1 or of a nucleic acid coding for VEGFR1 as a biomarker in a method for designing or in designing a method for the treatment of a subject, wherein the method for the treatment comprises administering to the subject a PKN3 inhibitor.

In accordance with the present invention, in its various aspects, either VEGFR1, i.e. the protein, or a nucleic acid which codes for VEGFR1 is used as a biomarker or is used in the methods and products of the present invention. It will be acknowledged by a person skilled in the art that, at the level of the nucleic acid, there are a total of four different transcript variants for VEGFR1, namely VEGFR1 transcript variant 2, VEGFR1 transcript variant 1, VEGFR1 transcript variant 3 and VEGFR1 transcript variant 4. It is understood that VEGFR1 transcript 2 codes for soluble VEGFR1 and VEGFR1 transcript 1 codes for the membrane-bound VEGFR1. VEGFR1 transcripts 3 and 4 code for fragments of VEGFR1. It is within the present invention that any of the VEGFR1 transcript variants 1 to 4 is, in principle, suitable for use in connection with the present invention. It is also within the present invention that any of the VEGFR1 variants 1 to 4 is, in principle suitable for use in connection with the various aspects of the present invention. As preferably used herein, a VEGFR1 variant 1 is a protein encoded by VEGFR1 splice variant 1, a VEGFR1 variant 2 is a protein encoded by VEGFR1 splice variant 2, a VEGFR1 variant 3 is a protein encoded by VEGFR1 splice variant 3, and a VEGFR1 variant 4 is a protein encoded by VEGFR1 splice variant 4.

As preferably used herein in connection with any aspect of the present invention a pharmacodynamics biomarker is a biomarker whose changes after treatment are associated with target modulation by a specific agent.

As preferably used herein in connection with any aspect of the present invention a predictive biomarker is a biomarker which can be used in advance of therapy to estimate response or survival of a specific patient on a specific treatment compared with another treatment.

As preferably used herein in connection with any aspect of the present invention a prognostic biomarker is a biomarker which provides information about the patient's overall disease outcome, regardless of therapy.

As preferably used herein in connection with any aspect of the present invention a surrogate biomarker is a biomarker intended to substitute for a clinical end point.

Whether a disease is a disease which can be treated, ameliorated and/or cured by a PKN3 inhibitor, can be determined by a person skilled in the art using routine methods and routine tests. For example, a person skilled in the art will use appropriate animal models, or any surrogate test system, and apply to such animal model or surrogate test system a PKN3 inhibitor and check whether the required read-out can be observed which goes along with the effect(s) of a PKN3 inhibitor. For example, such test may be the matrigel test described in international patent application WO 2008/009477, or any other tumor or cancer growth system involving PKN3 as a target molecule.

Preferably, a disease as used in the various aspects of the present invention is one which is selected from the group comprising:

A

Acute Lymphoblastic Leukemia (ALL)
Acute Myeloid Leukemia (AML)
Adolescents, Cancer in
Adrenocortical Carcinoma
  Childhood
AIDS-Related Cancers
  Kaposi Sarcoma
  Lymphoma
Anal Cancer
Appendix Cancer
Astrocytomas, Childhood
  Atypical Teratoid/Rhabdoid Tumor, Childhood, Central Nervous System

B

Basal Cell Carcinoma—see Skin Cancer (Nonmelanoma)
Bile Duct Cancer, Extrahepatic
Bladder Cancer
  Childhood
Bone Cancer, Osteosarcoma and Malignant Fibrous Histiocytoma
Brain Stem Glioma, Childhood
Brain Tumor
  Astrocytomas, Childhood
  Brain and Spinal Cord Tumors, Childhood
  Brain Stem Glioma, Childhood
  Central Nervous System Atypical Teratoid/Rhabdoid Tumor, Childhood
  Central Nervous System Embryonal Tumors, Childhood
  Central Nervous System Germ Cell Tumors, Childhood
  Craniopharyngioma, Childhood
  Ependymoblastoma, Childhood
  Ependymoma, Childhood
  Medulloblastoma, Childhood
  Medulloepithelioma, Childhood
  Pineal Parenchymal Tumors of Intermediate Differentiation, Childhood
  Supratentorial Primitive Neuroectodermal Tumors and Pineoblastoma, Childhood
Breast Cancer
  Childhood
  Male
  Pregnancy, Breast Cancer and
Bronchial Tumors, Childhood
Burkitt Lymphoma—see Non-Hodgkin Lymphoma

C

Carcinoid Tumor
  Childhood
  Gastrointestinal
Carcinoma of Unknown Primary
  Childhood
Central Nervous System
  Atypical Teratoid/Rhabdoid Tumor, Childhood
  Embryonal Tumors, Childhood
  Germ Cell Tumor, Childhood
  Lymphoma, Primary
Cervical Cancer
  Childhood
Childhood Cancers
Chordoma, Childhood
Chronic Lymphocytic Leukemia (CLL)
Chronic Myelogenous Leukemia (CML)
Chronic Myeloproliferative Disorders
Colon Cancer
Colorectal Cancer
  Childhood
Craniopharyngioma, Childhood
Cutaneous T-Cell Lymphoma—see Mycosis Fungoides and Sézary Syndrome

D

Duct, Bile, Extrahepatic
Ductal Carcinoma In Situ (DCIS)

E

Embryonal Tumors, Central Nervous System, Childhood
Endometrial Cancer
Ependymoblastoma, Childhood
Ependymoma, Childhood
Esophageal Cancer
  Childhood
Esthesioneuroblastoma, Childhood
Ewing Sarcoma Family of Tumors
Extracranial Germ Cell Tumor, Childhood
Extragonadal Germ Cell Tumor
Extrahepatic Bile Duct Cancer
Eye Cancer
  Intraocular Melanoma
  Retinoblastoma

F

Fibrous Histiocytoma of Bone, Malignant, and Osteosarcoma

G

Gallbladder Cancer
Gastric (Stomach) Cancer
  Childhood
Gastrointestinal Carcinoid Tumor
Gastrointestinal Stromal Tumors (GIST)—see Soft Tissue Sarcoma Germ Cell Tumor
  Central Nervous System, Childhood
  Extracranial, Childhood
  Extragonadal
  Ovarian
Gestational Trophoblastic Tumor
Glioma—see Brain Tumor
  Childhood Brain Stem
H
Hairy Cell Leukemia
Head and Neck Cancer
  Childhood
Heart Cancer, Childhood
Hepatocellular (Liver) Cancer
Histiocytosis, Langerhans Cell
Hodgkin Lymphoma
Hypopharyngeal Cancer
I
Intraocular Melanoma
Islet Cell Tumors, Pancreatic Neuroendocrine Tumors
K
Kaposi Sarcoma
Kidney
  Renal Cell
L
Langerhans Cell Histiocytosis
Laryngeal Cancer
  Childhood
Leukemia
  Acute Lymphoblastic (ALL)
  Acute Myeloid (AML)
  Chronic Lymphocytic (CLL)
  Chronic Myelogenous (CML)
  Hairy Cell
Lip and Oral Cavity Cancer
Liver Cancer (Primary)
Lobular Carcinoma In Situ (LCIS)
Lung Cancer
  Non-Small Cell
  Small Cell
Lymphoma
  AIDS-Related
  Burkitt—see Non-Hodgkin Lymphoma
  Cutaneous T-Cell—see Mycosis Fungoides and Sézary Syndrome
  Hodgkin
  Non-Hodgkin
  Primary Central Nervous System (CNS)
M
Macroglobulinemia, Waldenström
Male Breast Cancer
Malignant Fibrous Histiocytoma of Bone and Osteosarcoma
Medulloblastoma, Childhood
Medulloepithelioma, Childhood
Melanoma
  Childhood
  Intraocular (Eye)
Merkel Cell Carcinoma
Mesothelioma, Malignant
  Childhood
Metastatic Squamous Neck Cancer with Occult Primary
Midline Tract Carcinoma Involving NUT Gene
Mouth Cancer
Multiple Endocrine Neoplasia Syndromes, Childhood
Multiple Myeloma/Plasma Cell Neoplasm
Mycosis Fungoides
Myelodysplastic Syndromes
Myelodysplastic/Myeloproliferative Neoplasms
Myelogenous Leukemia, Chronic (CML)
Myeloid Leukemia, Acute (AML)
Myeloma, Multiple
Myeloproliferative Disorders, Chronic
N
Nasal Cavity and Paranasal Sinus Cancer
Nasopharyngeal Cancer
  Childhood
Neuroblastoma
Non-Hodgkin Lymphoma
Non-Small Cell Lung Cancer
O
Oral Cancer
  Childhood
Oral Cavity Cancer, Lip and
Oropharyngeal Cancer
Osteosarcoma and Malignant Fibrous Histiocytoma of Bone
Ovarian Cancer
  Childhood
  Epithelial
  Germ Cell Tumor
  Low Malignant Potential Tumor
P
Pancreatic Cancer
  Childhood
  Pancreatic Neuroendocrine Tumors (Islet Cell Tumors)
Papillomatosis, Childhood
Paraganglioma
Paranasal Sinus and Nasal Cavity Cancer
Parathyroid Cancer
Penile Cancer
Pharyngeal Cancer
Pheochromocytoma
Pineal Parenchymal Tumors of Intermediate Differentiation, Childhood
Pineoblastoma and Supratentorial Primitive Neuroectodermal Tumors, Childhood
Pituitary Tumor
Plasma Cell Neoplasm/Multiple Myeloma
Pleuropulmonary Blastoma, Childhood
Pregnancy and Breast Cancer
Primary Central Nervous System (CNS) Lymphoma
Prostate Cancer
R
Rectal Cancer
Renal Cell (Kidney) Cancer
Renal Pelvis and Ureter, Transitional Cell Cancer
Retinoblastoma
Rhabdomyosarcoma, Childhood
S
Salivary Gland Cancer
  Childhood
Sarcoma
  Ewing Sarcoma Family of Tumors
  Kaposi
  Soft Tissue
  Uterine
Sézary Syndrome
Skin Cancer
  Childhood
  Melanoma
  Merkel Cell Carcinoma
  Nonmelanoma
Small Cell Lung Cancer
Small Intestine Cancer
Soft Tissue Sarcoma Squamous Cell Carcinoma—see Skin Cancer (Nonmelanoma)
Squamous Neck Cancer with Occult Primary, Metastatic
Stomach (Gastric) Cancer
  Childhood
Supratentorial Primitive Neuroectodermal Tumors, Childhood
T
T-Cell Lymphoma, Cutaneous—see Mycosis Fungoides and Sézary Syndrome
Testicular Cancer
  Childhood
Throat Cancer
Thymoma and Thymic Carcinoma
  Childhood
Thyroid Cancer
  Childhood
Transitional Cell Cancer of the Renal Pelvis and Ureter
Trophoblastic Tumor, Gestational
U
Unknown Primary, Carcinoma of
  Childhood
Unusual Cancers of Childhood
Ureter and Renal Pelvis, Transitional Cell Cancer
Urethral Cancer
Uterine Cancer, Endometrial
Uterine Sarcoma
V
Vaginal Cancer
  Childhood
Vulvar Cancer
W
Waldenström Macroglobulinemia
Wilms Tumor
Women's Cancers
Y
Young Adults, Cancer in as may be taken from the list of cancers provided by the National Cancer Institute at the National Institutes of Health.

In each and any aspect of the present invention the PKN3 inhibitor may be a compound which is selected from the group comprising an siRNA directed against an mRNA coding for PKN3, an antisense oligonucleotide directed against an mRNA coding for PKN3, a ribozyme directed against an mRNA coding for PKN3, an shRNA directed against an mRNA coding for PKN3, an miRNA or antagomir directed against an mRNA coding for PKN3, an aptamer directed against PKN3, a spiegelmer directed against PKN3, an antibody directed against PKN3, an anticalin directed against PKN3, a small molecule. Each and any of the above classes of compounds are known to a person skilled in the art and a PKN3 inhibitor of each any of said classes can be generated by a person skilled in the art by applying standard technology.

The manufacture of an antibody specific for VEGFR1 in its diverse forms is known to the one skilled in the art and, for example, described in Harlow, E., and Lane, D., "Antibodies: A Laboratory Manual," Cold Spring Harbor Laboratory, Cold Spring Harbor, N.Y., (1988). Preferably, monoclonal antibodies may be used in connection with the present invention which may be manufactured according to the protocol of Cesar and Milstein and further developments based thereon. Antibodies as used herein, include, but are not limited to, complete antibodies, antibody fragments or derivatives such as Fab fragments, Fc fragments and single-stranded antibodies, as long as they are suitable and capable of binding to VEGFR1 as disclosed herein. Apart from monoclonal antibodies also polyclonal antibodies may be used and/or generated. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988). Preferably, the antibodies used for therapeutical purposes are humanized or human antibodies as defined above.

The antibodies which may be used according to the present invention may have one or several markers or labels. Such markers or labels may be useful to detect the antibody either in its diagnostic application or its therapeutic application. Preferably the markers and labels are selected from the group comprising avidine, streptavidine, biotin, gold and fluorescein and used, e.g., in ELISA methods. These and further markers as well as methods are, e.g. described in Harlow, E., and Lane, D., "Antibodies: A Laboratory Manual," Cold Spring Harbor Laboratory, Cold Spring Harbor, N.Y., (1988).

"Anticalins" are, among others, described in German patent application DE 197 42 706.

Aptamers are D-nucleic acids which are either single stranded or double stranded and which specifically interact with a target molecule. The manufacture or selection of aptamers is, e.g., described in European patent EP 0 533 838. Basically the following steps are realized. First, a mixture of nucleic acids, i.e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e.g., by introducing defined chemical groups which are known to the one skilled in the art of generating aptamers. Such modification may for example reside in the introduction of an amino group at the 2'-position of the sugar moiety of the nucleotides. Aptamers are currently used as therapeutical agents. However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The thus obtained small molecule may then be subject to further derivatisation and modification to optimise its physical, chemical, biological and/or medical characteristics such as toxicity, specificity, biodegradability and bioavailability.

The generation or manufacture of spiegelmers which may be used or generated according to the present invention using VEGFR1 as disclosed herein, is based on a similar principle. The manufacture of spiegelmers is described in the international patent application WO 98/08856. Spiegelmers are L-nucleic acids, which means that they are composed of L-nucleotides rather than aptamers which are composed of D-nucleotides as aptamers are. Spiegelmers are characterized by the fact that they have a very high stability in biological system and, comparable to aptamers, specifically interact with the target molecule against which they are directed. In the purpose of generating spiegelmers, a heterogonous population of D-nucleic acids is created and this population is contacted with the optical antipode of the target molecule, in the present case for example with the D-enantiomer of the naturally occurring L-enantiomer of the protein kinase N beta. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

Ribozymes are catalytically active nucleic acids which preferably consist of RNA which basically comprises two moieties. The first moiety shows a catalytic activity whereas the second moiety is responsible for the specific interaction with the target nucleic acid, in the present case the nucleic acid coding for VEGFR1 as disclosed herein. Upon interaction between the target nucleic acid and the second moiety of the ribozyme, typically by hybridisation and Watson-Crick base pairing of essentially complementary stretches of bases on the two hybridising strands, the catalytically active moiety may become active which means that it catalyses, either intramolecularly or intermolecularly, the target nucleic acid in case the catalytic activity of the ribozyme is a phosphodiesterase activity. Subsequently, there may be a further degradation of the target nucleic acid which in the end results in the degradation of the target nucleic acid as well as the protein derived from the said target nucleic acid due to a lack of newly synthesized VEGFR1 as disclosed herein and a turn-over of prior existing VEGFR1 as disclosed herein. Ribozymes, their use and design principles are known to the one skilled in the art, and, for example described in Doherty and Doudna (Ribozym structures and mechanism. Annu ref Biophys. Biomolstruct. 2001; 30:457-75) and Lewin and Hauswirth (Ribozyme Gene Therapy: Applications for molecular medicine. 2001 7: 221-8).

Antisense oligonucleotides are as such equally known in the art as is their use for the manufacture of a medicament and as a diagnostic agent, respectively. Basically, antisense oligonucleotides hybridise based on base complementarity, with a target RNA, preferably with a mRNA, thereby activate RNase H. RNase H is activated by both phosphodiester and phosphorothioate-coupled DNA. Phosphodiester-coupled DNA, however, is rapidly degraded by cellular nucleases with the exception of phosphorothioate-coupled DNA. These resistant, non-naturally occurring DNA derivatives do not inhibit RNase H upon hybridisation with RNA. In other words, antisense polynucleotides are only effective as DNA RNA hybride complexes. Examples for this kind of antisense oligonucleotides are described, among others, in U.S. Pat. No. 5,849,902 and U.S. Pat. No. 5,989,912. In other words, based on the nucleic acid sequence of the target molecule which in the present case is the nucleic acid coding for VEGFR1 as disclosed herein, either from the target protein from which a respective nucleic acid sequence may in principle be deduced, or by knowing the nucleic acid sequence as such, particularly the mRNA, suitable antisense oligonucleotides may be designed base on the principle of base complementarity.

siRNA is a double stranded RNA having typically a length of about 19 to about 23 nucleotides. The sequence of one of the two RNA strands corresponds to the sequence of the target nucleic acid such as the nucleic acid coding for target molecule, to be degraded. In other words, knowing the nucleic acid sequence of the target molecule, in the present case VEGFR1 in its various forms described herein, preferably the mRNA sequence, a double stranded RNA may be designed with one of the two strands being complementary to said, e.g. mRNA of the target molecule and, upon application of said siRNA to a system containing the gene, genomic DNA, hnRNA or mRNA coding for the target molecule, the respective target nucleic acid will be degraded and thus the level of the respective protein be reduced. The basic principles of designing, constructing and using said siRNA as medicament and diagnostic agent, respectively, is, among others, described in international patent applications WO 00/44895 and WO 01/75164.

Based on the aforementioned design principles, it is possible to generate such siRNA, antisense oligonucleotide and ribozyme, respectively, once the nucleic acid sequence coding for the target molecule is known. This is also true for precursor molecules of nucleic acid such as hnRNA, cDNA and the like, including genomic nucleic acid. Of course, also knowing the respective antisense strand may allow the design of such nucleic acid based compounds given the basic principle of base pair complementarity, preferably based on Watson-Crick base pairing. Accordingly, a further aspect of the present invention is related to specific siRNAs, ribozymes and antisense nucleotides which are directed against or specific for protein kinase N-beta. In the following, this is further illustrated by siRNA, however, this applies to antisense oligonucleotides and ribozymes as well, as will be acknowledged by the ones skilled in the art.

Such siRNA comprises preferably a length of from 15 to 25 nucleotides, whereby this means actually any length comprising 15, 16, 17, 18, 20, 21, 22, 23, 24 or 25 nucleotides. In further embodiments, the siRNA may even exhibit more nucleotides. According the design principles well known in the art, respective siRNA can be generated. Accordingly, the siRNA claimed herein comprises a stretch of preferably any nucleotide length from 15 to 25 consecutive nucleotides which is either at least partially complementary to the sense or to the antisense strand encoding the target molecule, and a second ribonucleotide strand which is at least partially complementary to the first one and thus to the antisense strand and sense strand respectively, encoding the target molecule. Any design principle known in the art of generation or manufacture of siRNA may be applied to this kind of duplex structure. The siRNA space disclosed herein comprises siRNA molecules the antisense strand of which starts with a nucleotides which corresponds to nucleotide no. 1 of a the target molecule as specified above. Further such siRNA molecules start with a nucleotide which corresponds to nucleotide no 2 of the target molecule encoding sequence as specified above, and so on. This kind of scanning over the target molecule encoding sequence is repeated so as to provide all possible siRNA molecules which can be directed against the target molecule. The length of any of the siRNA molecules thus generated may be any length suitable for siRNA, more particularly any length as specified above. Preferably, the various siRNA molecule of the siRNA molecule space disclosed herein, overlap except the most 5' terminal nucleotide of the antisense strand or sense strand. It is obvious that the thus obtained antisense sequences have to complemented through base pairing so as to form the at least partially double-stranded structure required for a functionally active siRNA.

MicroRNA for use in therapeutic applications are, for example, described in Soifer H S et al. (Soifer H S et al., Molecular therapy, vol. 15, no. 12, December 2007, pages 2070-2079).

Antagomirs for use in therapeutic applications are, for example, described in Stenvang J & Kauppinen S (Stenvang J & Kauppinen S, Expert Opin. Biol. Ther. (2008) 8(1), pages 59-81).

A preferred embodiment the PKN3 inhibitor is an siRNA which is double-stranded (ds 23 mer) having the following composition and structure, respectively:

```
                          (SEQ ID NO: 11)
5' 5u8u7c6g8a6g5c7u7a6g5c5 3'

                          (SEQ ID NO: 12)
3' a6c6g8u7c5u7a8g6g5u7a8a 5'
```

with unmodified ribonucleotides being as indicated and modified ribonucleotides being represented as follows:

5: 2'-O-Methyl-u,

6: 2'-O-Methyl-a,

7: 2'-O-Methyl-c,

8: 2'-O-Methyl-g.

In a further preferred embodiment of the various aspects of the present invention the PKN3 inhibitor is a composition referred to in the prior art and herein as Atu027. The active pharmaceutical ingredient (API) of Atu027 is a PKN3-specific siRNA. The siRNA is a double stranded RNA molecule containing naturally occurring 2'-O-Methyl-modifications. The 2'-O-methyl modifications stabilize the RNA by protection from nuclease attack. The double strand (ds-23 mer) is composed of the following sequences:

```
                          (SEQ ID NO: 11)
5' 5u8u7c6g8a6g5c7u7a6g5c5 3'

                          (SEQ ID NO: 12)
3' a6c6g8u7c5u7a8g6g5u7a8a 5'
```

with unmodified ribonucleotides being as indicated and modified ribonucleotides being represented as follows:

5: 2'-O-Methyl-u,

6: 2'-O-Methyl-a,

7: 2'-O-Methyl-c,

8: 2'-O-Methyl-g.

For production of Atu027 the PKN3-specific siRNA is formulated with positively charged liposomes composed of three lipids, i.e. the cationic AtuFect01, the neutral, fusogenic DPyPE helperlipid and the PEGylated lipid MPEG-2000-DSPE in a molar ratio of 50/49/1 to deliver the negatively charged siRNA in lipoplexed form. AtuFect01 and DPyPE helperlipid are novel excipients. The third lipid MPEG-2000-DSPE is a known excipient. The structure of the 3 lipids is presented below:

Cationic lipid AtuFect01: ((β-(L-Arginyl)-2,3-L-diamino-propionic acid-N-palmityl-N-oleyl-amide tri-hydrochloride)

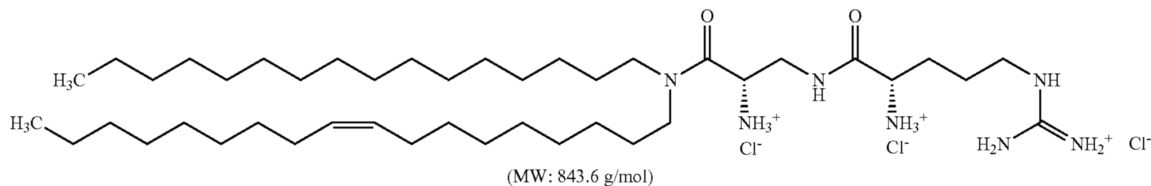 [SMILES: CCCCCCCC/C=C\CCCCCCCCN(CCCCCCCCCCCCCCCC)C(=O)[C@@H]([NH3+])CNC(=O)[C@@H]([NH3+])CCCNC(N)=[NH2+] ; [Cl-] ; [Cl-] ; [Cl-]]

(MW: 843.6 g/mol)

Fusogenic/helperlipid DPyPE: 1,2-Diphytanoyl-sn-glycero-3-phosphoethanolamine

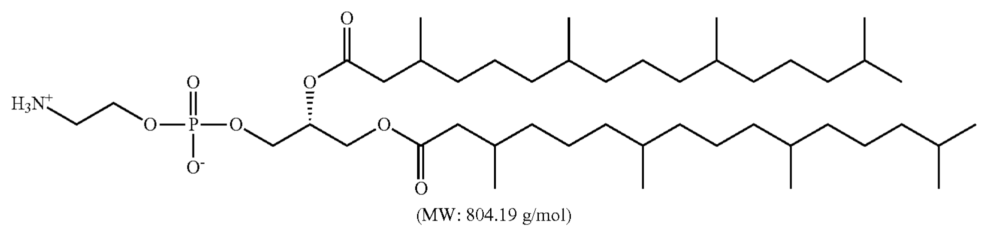 [SMILES: CC(C)CCCC(C)CCCC(C)CCCC(C)CC(=O)OC[C@H](COP(=O)([O-])OCC[NH3+])OC(=O)CC(C)CCCC(C)CCCC(C)CCCC(C)C]

(MW: 804.19 g/mol)

PEG-lipid MPEG-2000-DSPE: N-(Carbonyl-methoxypolyethyleneglycol-2000)-1,2-distearoyl-sn-glycero-3-phosphoethanolamine sodium salt

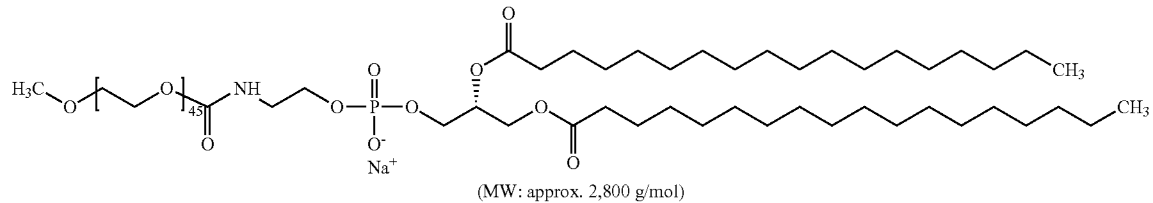

(MW: approx. 2,800 g/mol)

It is within the present invention that any of the PKN3 inhibitors disclosed herein can be used in connection with each and any aspect of the present invention, including the method of the present invention and the PKN3 inhibitor for use in a method for the treatment of a subject suffering from or being at risk of suffering from a disease of the present invention.

It is within the present invention that any of the disease disclosed herein can be used in connection with each and any aspect of the present invention, including the method of the present invention and the PKN3 inhibitor for use in a method for the treatment of a subject suffering from or being at risk of suffering from a disease of the present invention.

It is also within the present invention that any of the VEGFR1 and nucleic acid coding therefor disclosed herein can be used in connection with each and any aspect of the present invention, including the method of the present invention and the PKN3 inhibitor for use in a method for the treatment of a subject suffering from or being at risk of suffering from a disease of the present invention.

Methods for the detection of VEGFR1 are known in the art and include, but are not limited to anti-VEGFR1 antibodies. In embodiments of the various aspects of the present invention VEGFR1 is detected by means of ELISA. However, other means are known to a person skilled in the art such as detection by mass spectrometry and the like.

In connection with the various aspects of the present invention a sample is a sample of a body fluid, whereby the body fluid is selected from the group comprising blood, plasma, liquor, urine and saliva. Preferred samples are blood samples and plasma samples.

Methods for the detection of a nucleic acid coding for VEGFR1 are also known in the art and include, but are not limited to PCR and RT-PCR.

VEGFR1 and soluble VEGFR1 (sVEGFR1) are known in the art and described, among others, in Caine G J et al. (Caine, G J, European Journal of Clinical Investigation (2003), 33, 883-890) or Barleon B et al. (Barleon B et al., Angionesis 4: 143-154 (2001)). Barleaon B et al. (supra) also disclose that the titre of soluble VEGFR1 is about 160 pg/ml in healthy volunteers.

The present invention is now further illustrated by the attached Figs and examples from which further feature, embodiments and advantages of the present invention may be taken.

The following list summarizes some of the SEQ ID NOs and provide an indication as to what they represent.

| | |
|---|---|
| SEQ ID NO: 1 | amino acid sequence of soluble VEGFR1 or VEGFR1 variant 2 |

-continued

| | |
|---|---|
| SEQ ID NO: 2 | nucleotide sequence coding for soluble VEGFR1 or VEGFR1 transcript variant 2 |
| SEQ ID NO: 3 | amino acid sequence of VEGFR1 variant 1 |
| SEQ ID NO: 4 | nucleotide sequence coding for VEGFR1 transcript variant 1 |
| SEQ ID NO: 5 | amino acid sequence of VEGFR1 variant 3 |
| SEQ ID NO: 6 | nucleotide sequence coding for VEGFR1 transcript variant 3 |
| SEQ ID NO: 7 | amino acid sequence of VEGFR1 variant 4 |
| SEQ ID NO: 8 | nucleotide sequence coding for VEGFR1 transcript variant 4 |
| SEQ ID NO: 9 | amino acid sequence of PKN3 |
| SEQ ID NO: 10 | nucleotide sequence coding for PKN3 |

BRIEF DESCRIPTION OF THE FIGURES

FIG. 1 is a diagram indicating PKN3 knock down, VEGFR1 expression and VEGFR2 expression in PC-3 cells. Human PC-3 cell line was obtained from American Type Culture Collection and cultivated according to the ATCC's recommendation. Cell line was transfected with Luciferase AtuPLEX and Atu027, respectively. Briefly, about 16 h after cell seeding siRNA-lipoplex solution diluted in 10% serum containing medium was added to the cells to achieve transfection concentration of 20 nM siRNA. After transfection (24 h, 48 h, 72 h, and 96 h), cells were lysed, total RNA was isolated and subjected to qRT-PCR. Graphs show respective mRNA level as mean of technical replicate relative to untreated @ 24 h. A decrease in VEGFR1 but not VEGFR2 expression in response to PKN3 knock down is observed.

FIG. 2 is a diagram indicating PKN3 knock down, VEGFR1 expression and VEGFR2 expression in MDA-MB-435 cells. Human MDA-MB-435 cell line was obtained from American Type Culture Collection and cultivated according to the ATCC's recommendation. Cell line was transfected with Luciferase AtuPLEX and Atu027, respectively. Briefly, about 16 h after cell seeding siRNA-lipoplex solution diluted in 10% serum containing medium was added to the cells to achieve transfection concentration of 20 nM siRNA. After transfection (24 h, 48 h, 72 h, and 96 h), cells were lysed, total RNA was isolated and subjected to qRT-PCR. Graphs show respective mRNA level as mean of technical replicate relative to untreated @ 24 h. A decrease in VEGFR1 but not VEGFR2 expression in response to PKN3 knock down is observed.

FIG. 13 represents SEQ ID NO: 1.

FIG. 14 represents SEQ ID NO: 2.

FIG. 15 represents SEQ ID NO: 3.

FIG. 16 represents SEQ ID NO: 4.

FIG. 17 represents SEQ ID NO: 5.

FIG. 18 represents SEQ ID NO: 6.

FIG. 19 represents SEQ ID NO: 7.

FIG. 20 represents SEQ ID NO: 8.

FIG. 21 represents SEQ ID NO: 9.

FIG. 22 represents SEQ ID NO: 10.

EXAMPLES

Example 1

Figure 3:
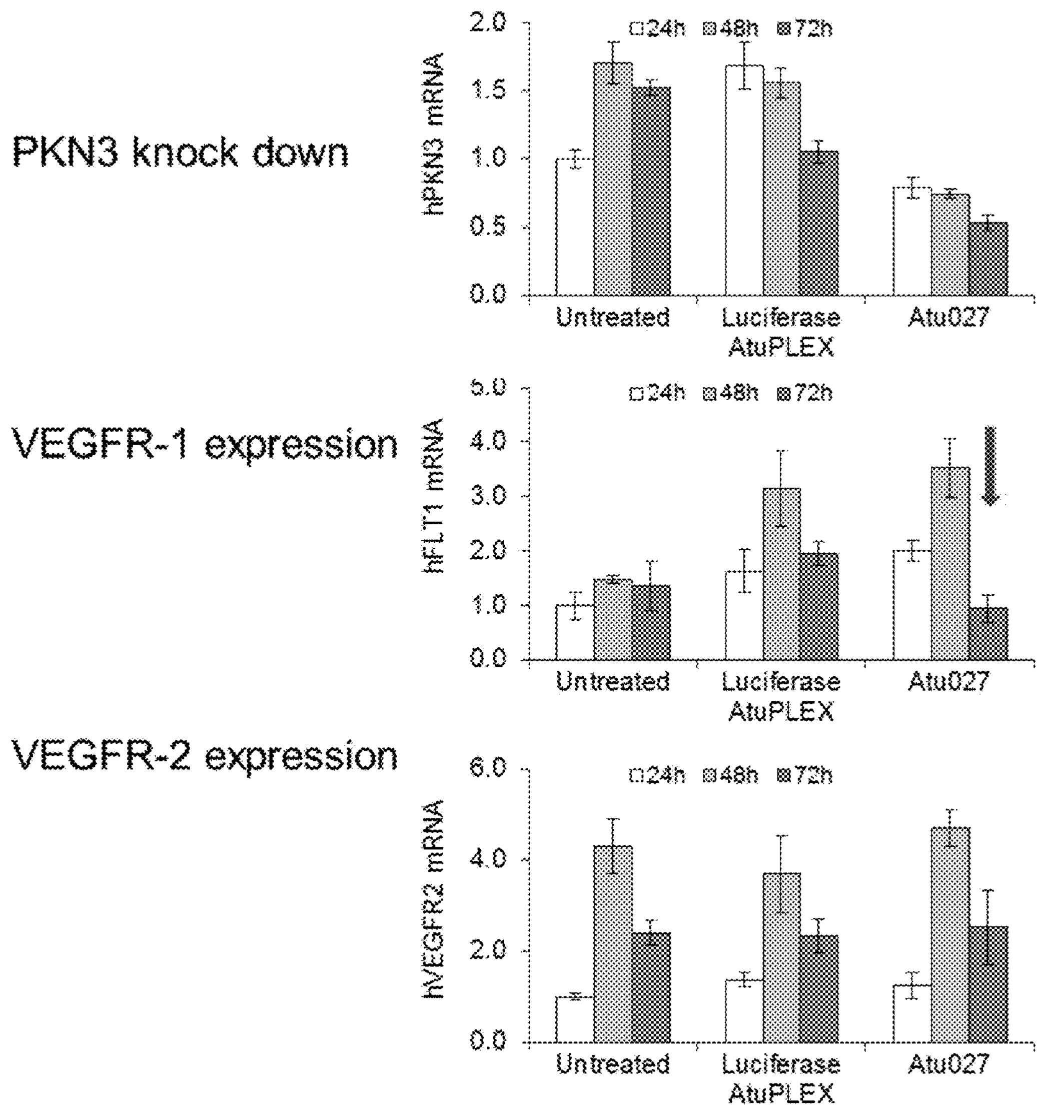
FIG. 3 is a diagram indicating PKN3 knock down, VEGFR1 expression and VEGFR2 expression in SKBR3 cells. Human SKBR3 cell line was obtained from American Type Culture Collection and cultivated according to the ATCC's recommendation. Cell line was transfected with Luciferase AtuPLEX and Atu027, respectively. Briefly, about 12 h after cell seeding siRNA-lipoplex solution diluted in 10% serum containing medium was added to the cells to achieve transfection concentration of 20 nM siRNA. After transfection (24 h, 48 h, 72 h, and 96 h), cells were lysed, total RNA was isolated and subjected to qRT-PCR. Graphs show respective mRNA level as mean of technical replicate relative to untreated @24 h. A decrease in VEGFR1 but not VEGFR2 expression in response to PKN3 knock down is observed.

Synthesis of RNAi Molecule (AtuRNAi) for In Vitro Studies

The siRNA molecules (AtuRNAi) of this invention are described in Table 1. These molecules were synthesized by BioSpring GmbH (Frankfurt a. M., Germany).

TABLE 1

| siRNA name | sequence 5' to 3' | SEQ ID NO |
|---|---|---|
| PKN3 s | agacuugaggacuuccuggacaa | 13 |
| PKN3 as | uuguccaggaaguccucaagucu | 14 |
| Luciferase s | aucacguacgcggaauacuucga | 15 |
| Luciferase as | ucgaaguauuccgcguacgugau | 16 |

Nucleotides with 2'-O-methyl modifications are underlined; "s" stands for the sense strand; and "as" stands for the antisense strand.

The duplexes formed by "PKN3 as" and "PKN3 s", and formed by "Luciferase as" and "Luciferase s" lack 3'-overhangs and are chemically stabilized by alternating 2'-O-methyl sugar modifications on both strands, whereby unmodified nucleotides face modified ones on the opposite strand (Table 1). These duplexes are also referred to herein as PKN3 and Luciferase and were resolved in water to obtain a stock concentration of 1 μM.

Example 2

Formulation of the AtuPLEX

The AtuPLEX formulation was prepared as essentially described in Santel et al. (Santel et al. Gene Therapy (2006) 13, 1222-1234). Cationic liposomes comprising the novel cationic lipid AtuFECT01 ((β-L-arginyl-2,3-L-diaminopropionic acid-N-palmityl-N-oleyl-amide trihydrochloride), the neutral phospholipid 1,2-diphytanoyl-sn-glycero-3-phosphoethanolamine (DPyPE) and the PEGylated lipid N-(Carbonyl-methoxypolyethyleneglycol-2000)-1,2-distearoyl-sn-glycero-3-phosphoethanolamine sodium salt (DSPE-PEG) in a molar ratio of 50/49/1 were prepared by lipid film re-hydration in 270 mM sterile RNase-free sucrose solution to a total lipid concentration of 4.335 mg/ml. Subsequently, the multilamellar dispersion was further processed by high-pressure homogenization using an EmulsiFlex C3 device (Avestin, Inc., Ottawa, Canada).

To generate siRNA-lipoplexes (AtuPLEX), the obtained liposomal dispersion was mixed with an equal volume of a 0.5625 mg/ml solution of siRNA in 270 mM sucrose, resulting in a calculated charge ratio of nucleic acid backbone phosphates to cationic lipid nitrogen atoms of approximately 1:4. The size of the liposome and the lipoplex dispersion and the zeta potential were measured using a Zetasizer Nano-ZS (Malvern Instruments, Worcestershire, UK).

The active pharmaceutical ingredient (API) of Atu027 is the PKN3-siRNA. The siRNA is a double stranded RNA molecule containing naturally occurring 2'-O-Methyl-modifications. The 2'-O-methyl modifications stabilize the RNA by protection from nuclease attack.

The double strand (ds-23 mer) is composed of the following sequence:

```
                                    (SEQ ID NO: 11)
5' 5u8u7c6g8a6g5c7u7a6g5c5 3'

                                    (SEQ ID NO: 12)
3' a6c6g8u7c5u7a8g6g5u7a8a 5'
```

Unmodified ribonucleotides: x;

Modifications: 5: 2'-O-Methyl-u, 6: 2'-O-Methyl-a, 7: 2'-O-Methyl-c, 8: 2'-O-Methyl-g.

For Atu027 production PKN3-siRNA is formulated with positively charged liposomes composed of three lipids, i.e. the cationic AtuFect01, the neutral, fusogenic DPyPE helperlipid and the PEGylated lipid MPEG-2000-DSPE in a molar ratio of 50/49/1 to deliver the negatively charged siRNA in lipoplexed form. AtuFect01 and DPyPE helperlipid are novel excipients. The third lipid MPEG-2000-DSPE is a known excipient. The structure of the 3 lipids is presented below:

Cationic lipid AtuFect01: ((β-(L-arginyl)-2,3-L-diaminopropionic acid-N-palmityl-N-oleyl-amide tri-hydrochloride)

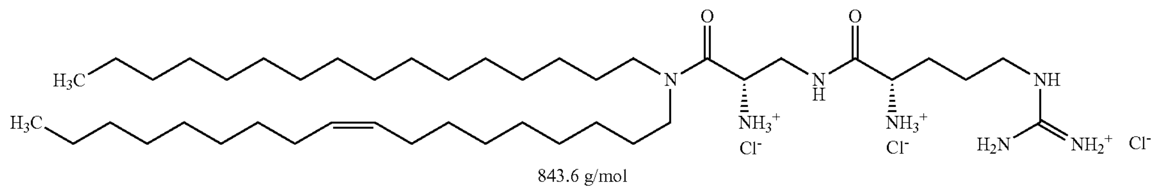 [SMILES: CCCCCCCC/C=C\CCCCCCCCN(CCCCCCCCCCCCCCCC)C(=O)[C@@H]([NH3+])CNC(=O)[C@@H]([NH3+])CCCNC(N)=[NH2+] ; [Cl-] ; [Cl-] ; [Cl-]]

843.6 g/mol

Fusogenic/helperlipid DPyPE: 1,2-Diphytanoyl-sn-Glycero-3-Phosphoethanolamine

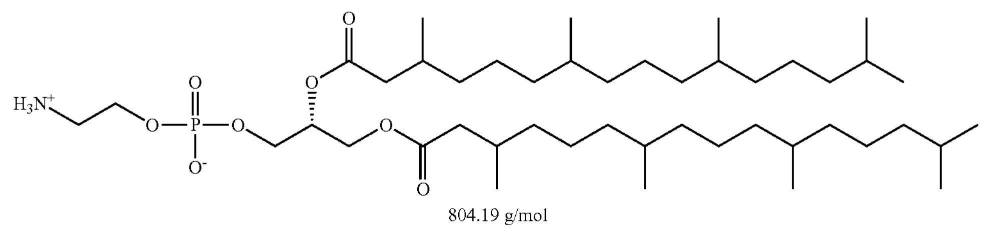 [SMILES: CC(C)CCCC(C)CCCC(C)CCCC(C)CC(=O)OC[C@H](COP(=O)([O-])OCC[NH3+])OC(=O)CC(C)CCCC(C)CCCC(C)CCCC(C)C]

804.19 g/mol

-

PEG-lipid MPEG-2000-DSPE: N-(Carbonyl-methoxypolyethyleneglycol-2000)-1,2-distearoyl-sn-glycero-3-phosphoethanolamine sodium salt

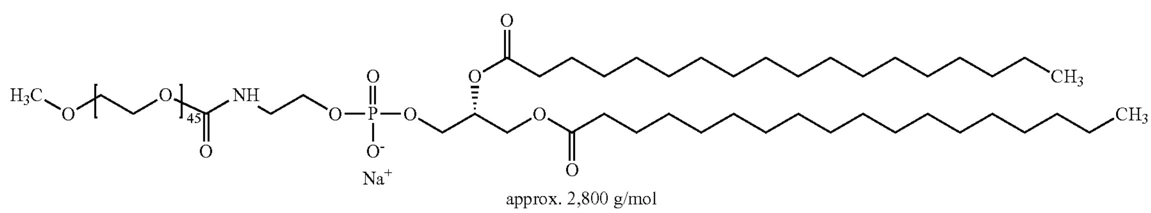

approx. 2,800 g/mol

Example 3

Expression of VEGFR-1 in Response to In Vitro Gene Silencing of Human PKN3 in Human Prostate Cancer PC-3 Cells $3\times10^5$ PC-3 cells were plated in 10-cm dishes, transfected 16 h later with 20 nM of the siRNA as described in Example 1 and 1 μg/ml liposome were prepared as described in Example 2, whereby the liposome consisted of the cationic lipid β-(L-arginyl)-2,3-L-diaminopropionic acid-N-palmityl-N-oleyl-amide tri-hydrochloride (AtuFECT01), the fusogenic lipid 1,2-diphytanoyl-sn-glycero-3-phosphoethanolamine (DPyPE) and the PEGylated lipid MPEG-2000-DSPE in a molar ratio of 50/49/1. Cells were lysed for RNA extraction 24 h, 48 h, 72 h and 96 h after transfection, respectively.

Total RNA was prepared with the InviTrap® Spin Cell RNA Mini Kit (Invitek, Berlin, Germany). Inhibition of PKN3 mRNA expression, expression of VEGFR1 and VEGFR2 mRNA was detected by real time RT-PCR (TaqMan) analysis using 300 nM PKN3, VEGFR1 and VEGFR2 specific forward and reverse primer and 100 nM probe. The sequences of the primers in TaqMan are listed in the following table, whereby UPR means upper primer, LWR means lower primer, and PRB means probe.

TABLE 2

| Name | Primer/ Probe | Sequence 5' to 3' | SEQ ID NO |
|---|---|---|---|
| Human PKN3 | UPR | CACTTTGGGAAGGTCCTCCTG | 17 |
| | PRB | FAM-TTCAAGGGGACAGGGAAATACTACGCCA-BHQ1 | 18 |
| | LWR | CCTCCTGCTTCTTCAGTGCTTT | 19 |
| Human VEGFR1 | UPR | CCCCGATTATGTGAGAAAAGGA | 20 |
| | PRB | FAM-CGACTTCCTCTGAAATGGATGGCTCCTG-BHQ1 | 21 |
| | LWR | CGCTCTTGGTGCTGTAGATTTG | 22 |
| Human VEGFR2 | UPR | TCTGCCTACCTCACCTGTTTCC | 23 |
| | PRB | FAM-ATGGAGGAGGAGGAAGTATGTGACCCCA-TAMRA | 24 |
| | LWR | TGACTGATTCCTGCTGTGTTGTC | 25 |

The reaction was carried out in 25 μl and assayed on the StepOnePlus™ Real-Time PCR System (Applied Biosystems) according to the manufacturer's instructions under the following conditions: 48° C. for 30 min, 95° C. for 10 min, followed by 40 cycles of 15 s at 95° C. and 1 min at 60° C. mRNA amounts are shown relative to untreated control lysed 24 h after transfection.

The results are shown in FIG. 1 indicating in vitro a marked decrease in VEGFR1 but not VEGFR2 mRNA expression in response to PKN3 knock down 72 h and 96 h post-transfection in human prostate cancer PC-3 cells.

Example 4

Expression of VEGFR-1 in Response to In Vitro Gene Silencing of Human PKN3 in Human Breast Carcinoma MDA-MB-435 Cells $3\times10^5$ MDA-MB-435 cells were plated in 10-cm dishes, transfected 16 h later with 20 nM of the siRNA as described in Example 1 and 1 μg/ml liposome were prepared as described in Example 2, whereby the liposome consisted of the cationic lipid β-(L-arginyl)-2,3-L-diaminopropionic acid-N-palmityl-N-oleyl-amide tri-hydrochloride (AtuFECT01), the fusogenic lipid 1,2-diphytanoyl-sn-glycero-3-phosphoethanolamine (DPyPE) and the PEGylated lipid MPEG-2000-DSPE in a molar ratio of 50/49/1. Cells were lysed for RNA extraction 24 h, 48 h, 72 h and 96 h after transfection, respectively.

Total RNA was prepared with the InviTrap® Spin Cell RNA Mini Kit (Invitek, Berlin, Germany). Inhibition of PKN3 mRNA expression, expression of VEGFR1 and VEGFR2 mRNA was detected by real time RT-PCR (TaqMan) analysis as described in example 3. mRNA amounts are shown relative to untreated control lysed 24 h after transfection.

The results are shown in FIG. 2 indicating in vitro a marked decrease in VEGFR1 but not VEGFR2 mRNA expression in response to PKN3 knock down at all time-points analyzed (24 h, 48 h, 72 h and 96 h post-transfection) in human breast carcinoma MDA-MB-435 cells.

Example 5

Expression of VEGFR-1 in Response to In Vitro Gene Silencing of Human PKN3 in Human Ovarian Cancer SKBR3 Cells $3\times10^5$ SKBR3 cells were plated in 10-cm dishes, transfected 16 h later with 20 nM of the siRNA as described in Example 1 and 1 μg/ml liposome were prepared as described in Example 2, whereby the liposome consisted of the cationic lipid β-(L-arginyl)-2,3-L-diaminopropionic acid-N-palmityl-N-oleyl-amide tri-hydrochloride (AtuFECT01), the fusogenic lipid 1,2-diphytanoyl-sn-glycero-3-phosphoethanolamine (DPyPE) and the PEGylated lipid MPEG-2000-DSPE in a molar ratio of 50/49/1. Cells were lysed for RNA extraction 24 h, 48 h and 72 h after transfection, respectively.

Total RNA was prepared with the InviTrap® Spin Cell RNA Mini Kit (Invitek, Berlin, Germany). Inhibition of PKN3 mRNA expression, expression of VEGFR1 and VEGFR2 mRNA was detected by real time RT-PCR (TaqMan) analysis as described in example 3. mRNA amounts are shown relative to untreated control lysed 24 h after transfection.

The results are shown in FIG. 3 indicating in vitro a marked decrease in VEGFR1 but not VEGFR2 mRNA expression in response to PKN3 knock down 72 h post-transfection in human ovarian cancer SKBR3 cells.

Example 6

Design of Clinical Phase I Study with Atu027

Figure 4:
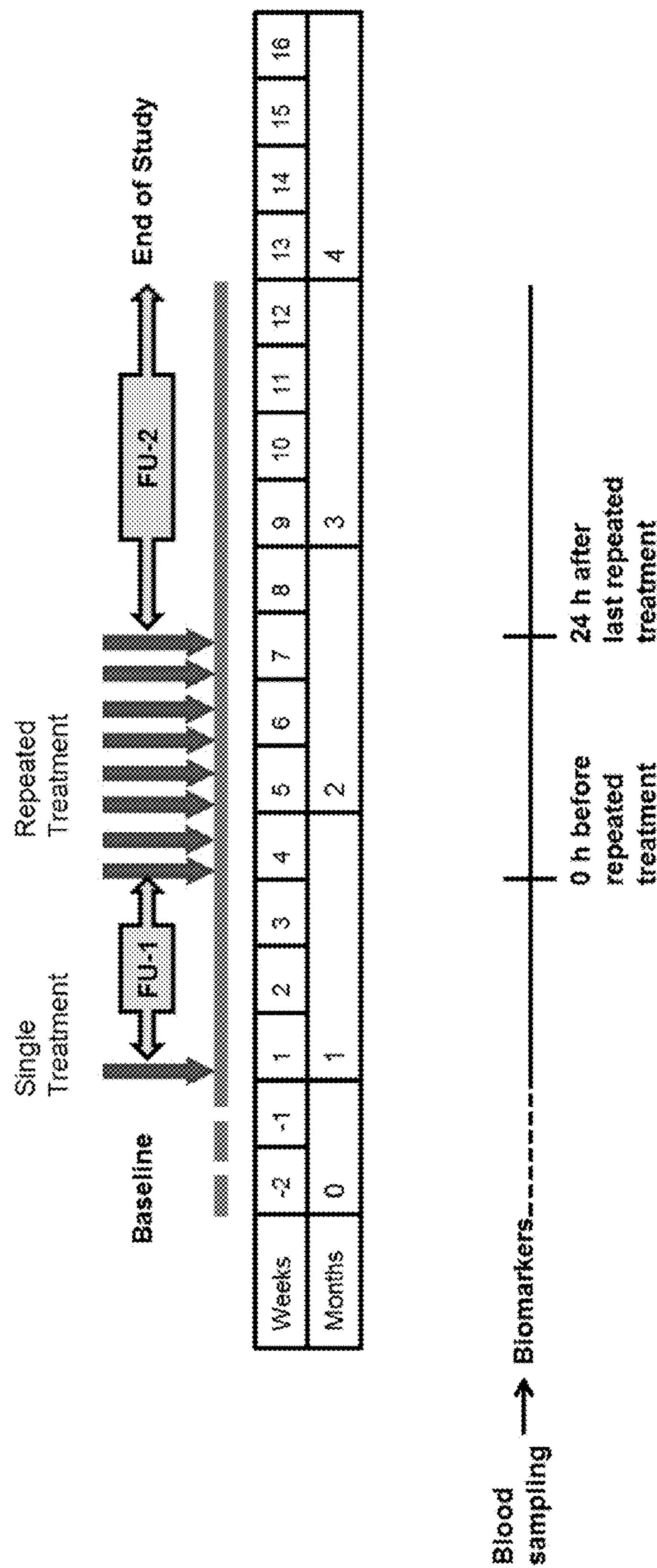
FIG. 4 is a representation of the design of a clinical phase I study. Before (0 h) and 24 h after the last (24 h) repeated treatment with Atu027 blood was withdrawn for biomarker analysis.

The Phase I study with Atu027 "A prospective, open label, single-centre, dose finding phase I study with Atu027 (an siRNA formulation) in subjects with advanced solid cancer—Atu027-I-01" (EudraCT No. 2008-005588-32/NCT00938574) was conducted. Study design is shown in FIG. 4. Before (0 h) and 24 h after the last (24 h) repeated 4-h intravenous infusion treatment with Atu027 blood was withdrawn for biomarker analysis. EDTA plasma was prepared by centrifugation according to standard protocols and stored at −20° C.

Example 7

Biomarker Analysis in Plasma of Humans Treated with Atu027

Before (0 h) and 24 h after the last (24 h) repeated treatment with Atu027 blood was withdrawn from nine patients and EDTA plasma was prepared. Samples were analyzed in a multiplexed immunoassay for concentration of respective analytes using the Luminex technology.

Figure 5:
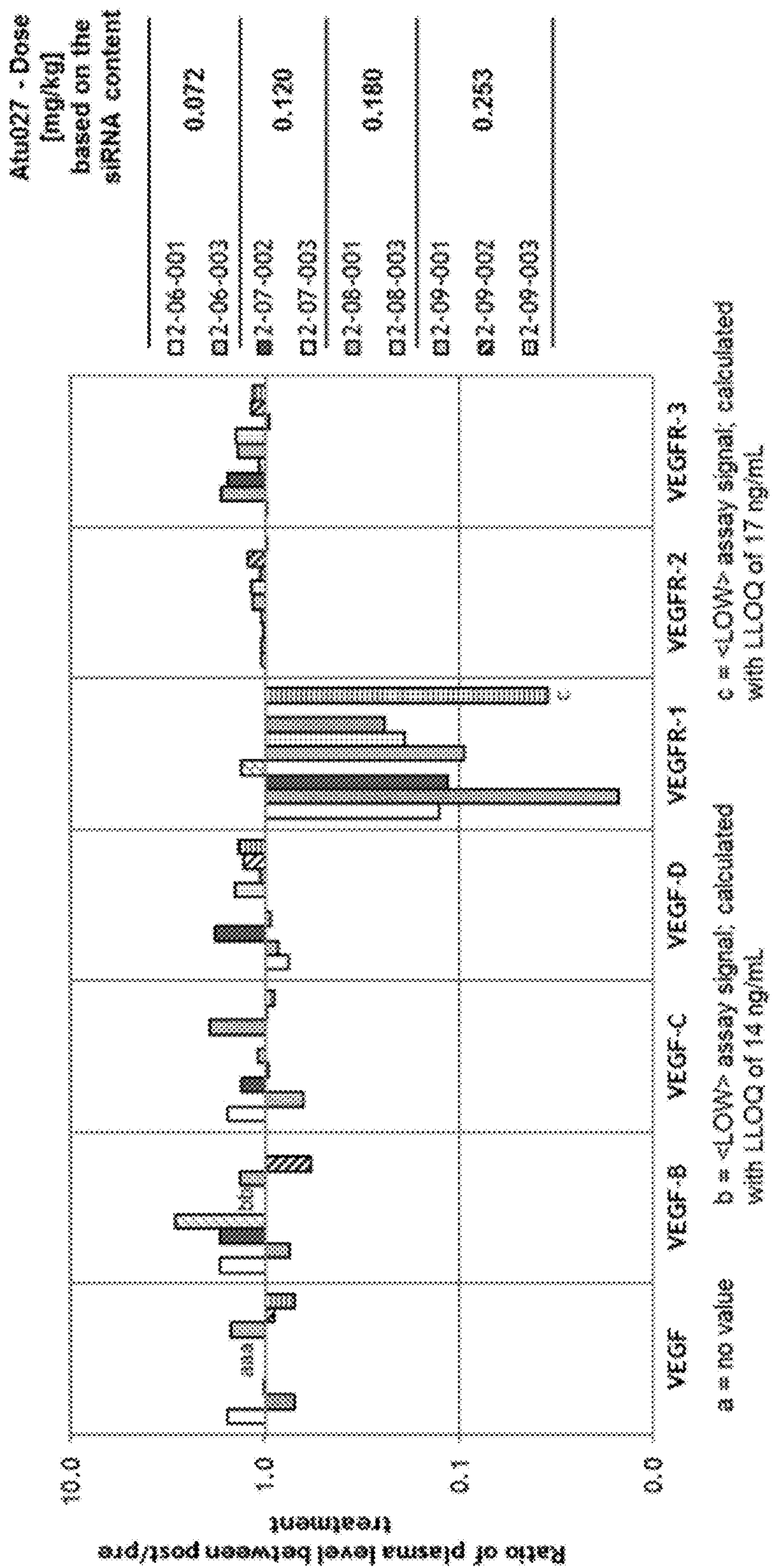
FIG. 5 shows the result of a biomarker analysis in plasma from humans treated with Atu027. Before (0 h) and 24 h after the last (24 h) repeated treatment with Atu027 blood was withdrawn from 9 patients and plasma was prepared. Samples were analyzed for biomarker analyte concentration. In the graph the ratio of post/pre treatment plasma level is shown for the VEGF isoforms and their receptors.
Figure 6:
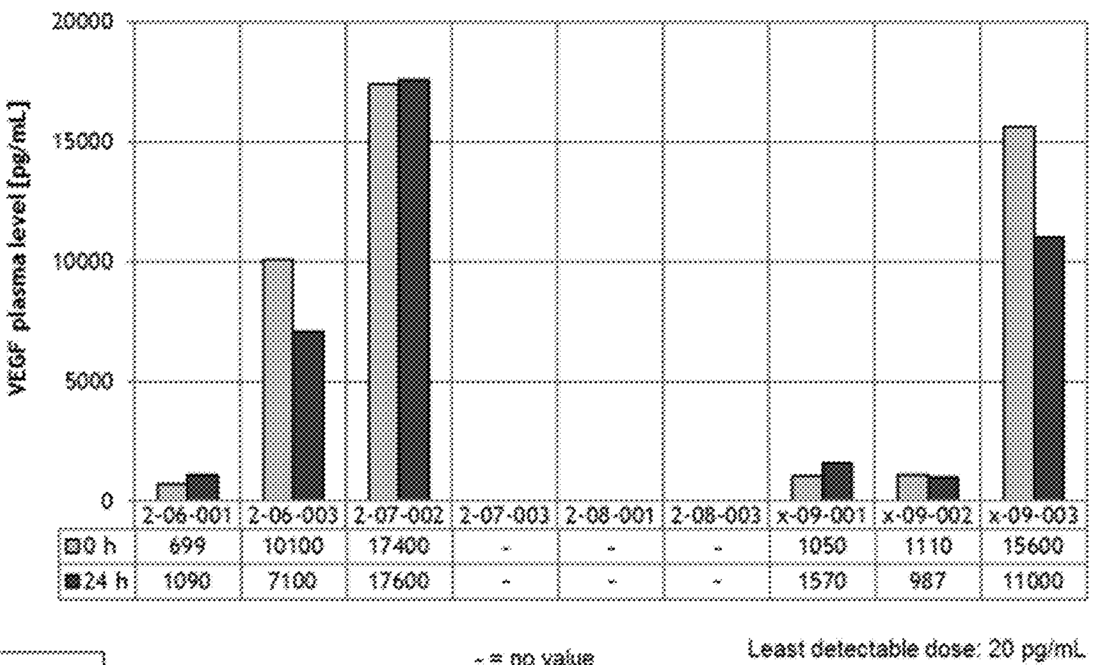
FIG. 6 shows the result of a biomarker analysis in plasma from humans treated with Atu027: single analytes—VEGF. Before (0 h) and 24 h after the last (24 h) repeated treatment with Atu027 blood was withdrawn from 9 patients and plasma was prepared. Samples were analyzed for biomarker analyte concentration. In the graph the absolute values for VEGF are presented.
Figure 7:
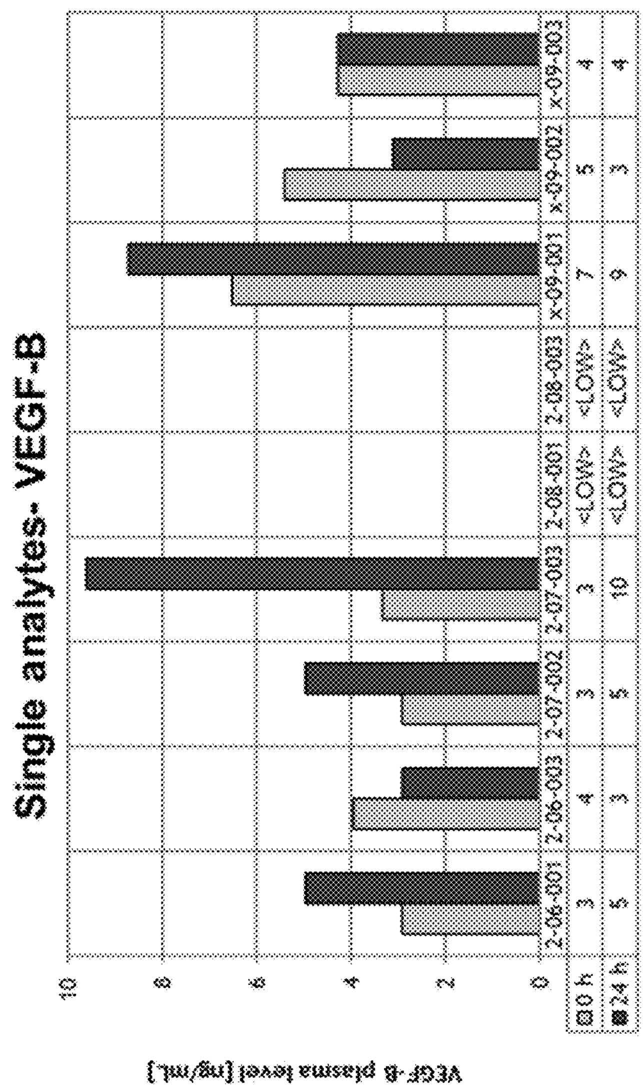
FIG. 7 shows the result of a biomarker analysis in plasma from humans treated with Atu027: single analytes—VEGF-B. Before (0 h) and 24 h after the last (24 h) repeated treatment with Atu027 blood was withdrawn from 9 patients and plasma was prepared. Samples were analyzed for biomarker analyte concentration. In the graph the absolute values for VEGF-B are presented.
Figure 8:
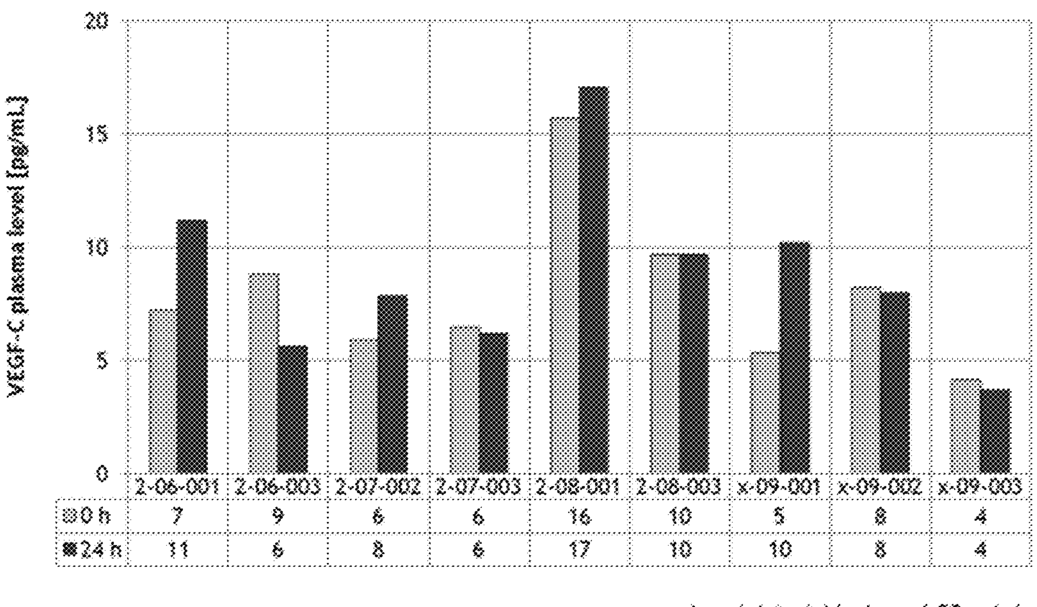
FIG. 8 shows the result of a biomarker analysis in plasma from humans treated with Atu027: single analytes—VEGF-C. Before (0 h) and 24 h after the last (24 h) repeated treatment with Atu027 blood was withdrawn from 9 patients and plasma was prepared. Samples were analyzed for biomarker analyte concentration. In the graph the absolute values for VEGF-C are presented.
Figure 9:
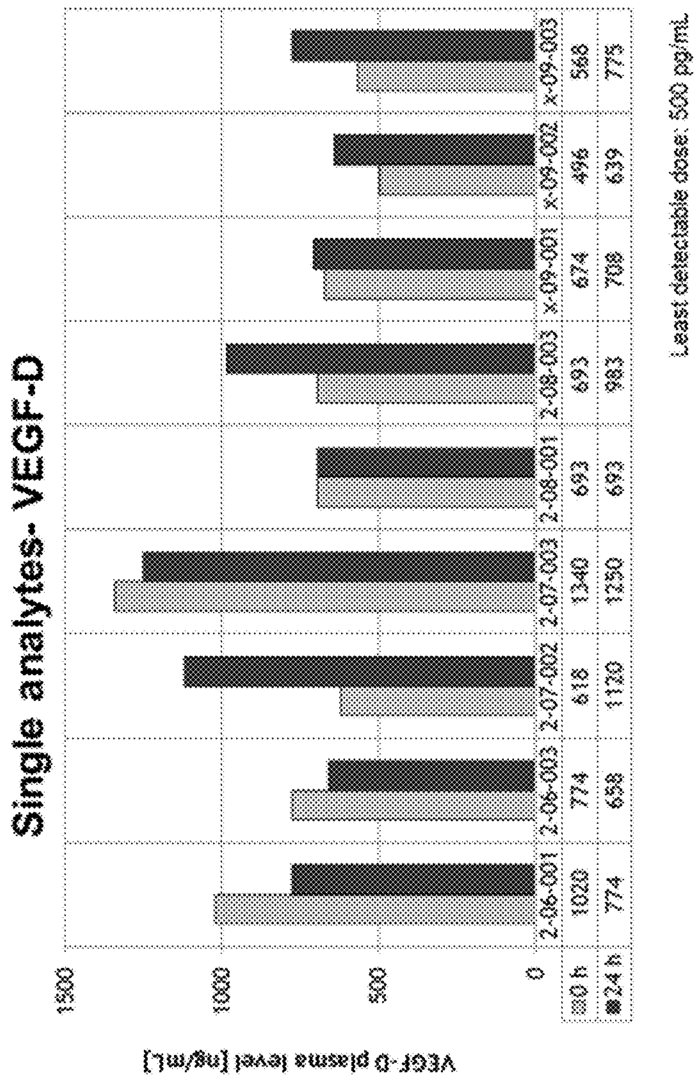
FIG. 9 shows the result of a biomarker analysis in plasma from humans treated with Atu027: single analytes—VEGF-D. Before (0 h) and 24 h after the last (24 h) repeated treatment with Atu027 blood was withdrawn from 9 patients and plasma was prepared. Samples were analyzed for biomarker analyte concentration. In the graph the absolute values for VEGF-D are presented.
Figure 10:
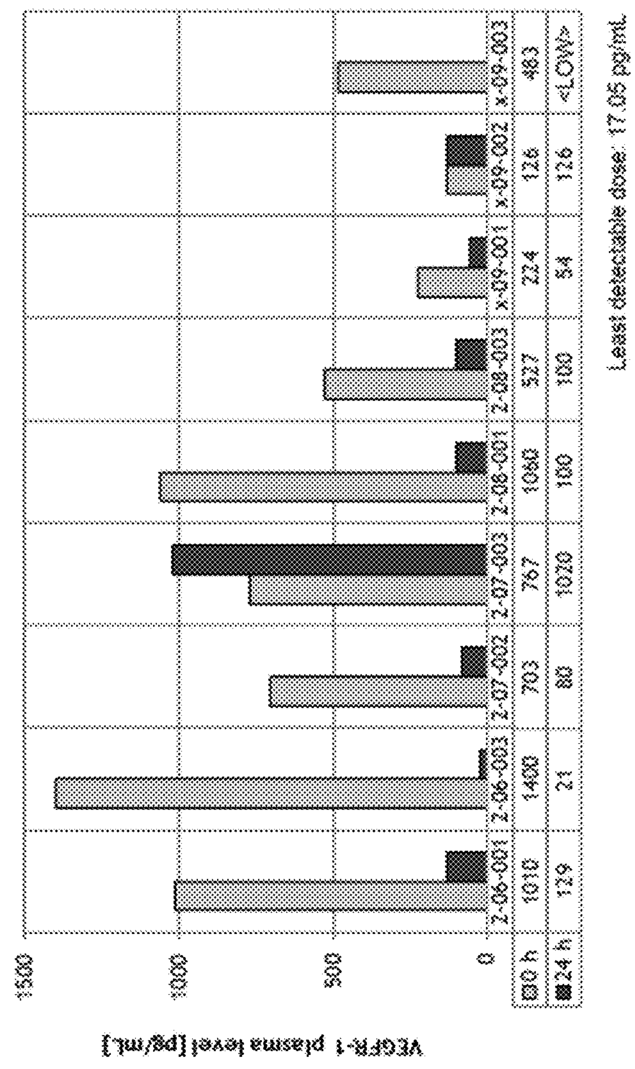
FIG. 10 shows the result of a biomarker analysis in plasma from humans treated with Atu027: single analytes—VEGFR1 (which is also referred to as VEGFR-1). Before (0 h) and 24 h after the last (24 h) repeated treatment with Atu027 blood was withdrawn from 9 patients and plasma was prepared. Samples were analyzed for biomarker analyte concentration. In the graph the absolute values for VEGFR-1 are presented. In 7 out of 9 patient samples, VEGFR-1 was decreased after repeated Atu027 treatment.
Figure 11:
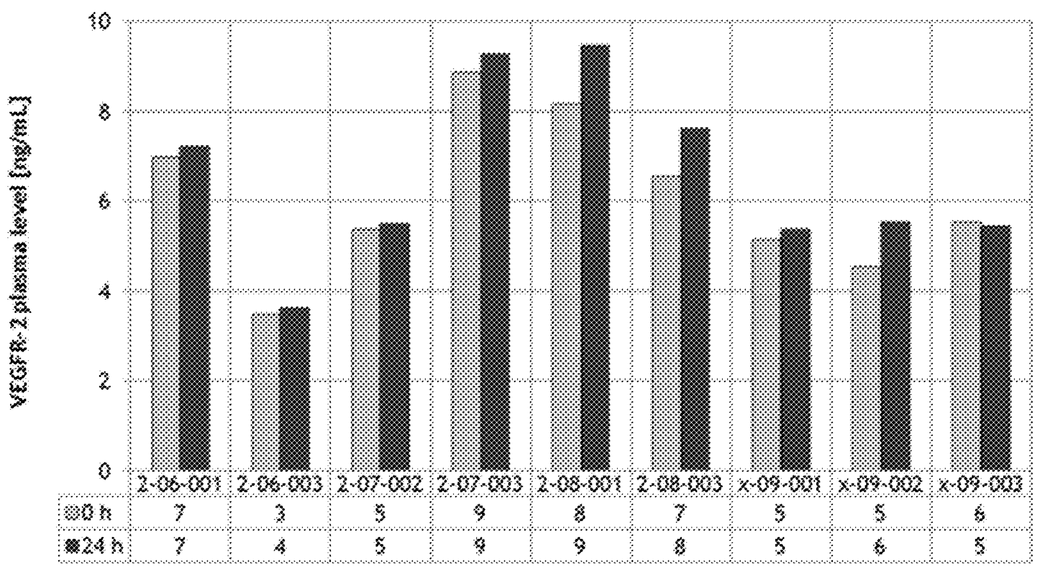
FIG. 11 shows the result of a biomarker analysis in plasma from humans treated with Atu027: single analytes—VEGFR2 (which is also referred to as VEGFR-2). Before (0 h) and 24 h after the last (24 h) repeated treatment with Atu027 blood was withdrawn from 9 patients and plasma was prepared. Samples were analyzed for biomarker analyte concentration. In the graph the absolute values for VEGFR-2 is presented.
Figure 12:
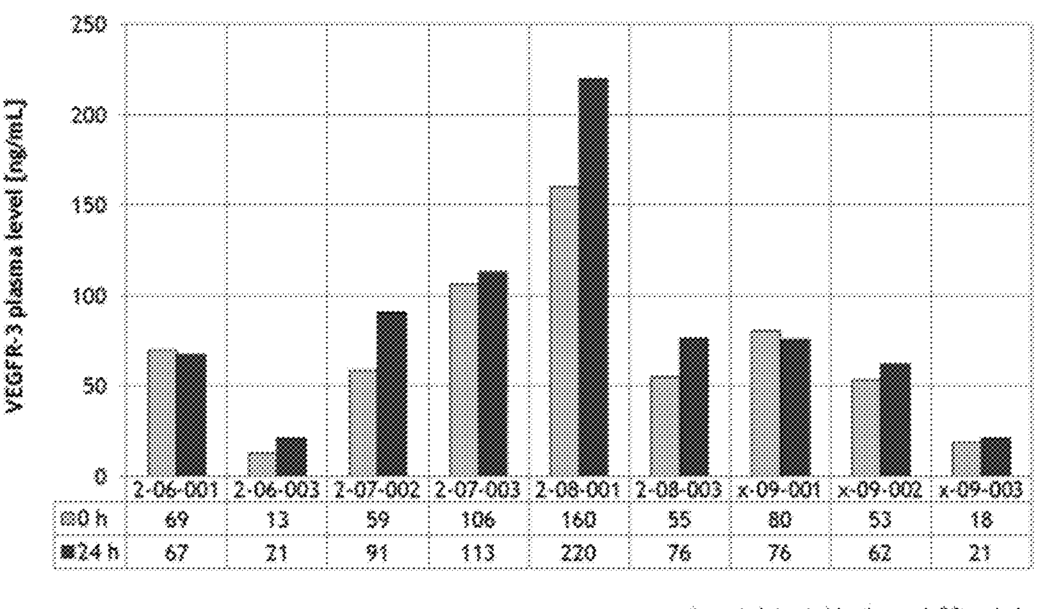
FIG. 12 shows the result of a biomarker analysis in plasma from humans treated with Atu027: single analytes—VEGFR3 (which is also referred to as VEGFR-3). Before (0 h) and 24 h after the last (24 h) repeated treatment with Atu027 blood was withdrawn from 9 patients and plasma was prepared. Samples were analyzed for biomarker analyte concentration. In the graph the absolute values for VEGFR-3 is presented.

In FIG. 5 the ratio of post/pre treatment plasma level (24 h level divided by the 0 h value) in the individual patient is shown for the VEGF isoforms VEGF, VEGF-B, VEGF-C, VEGF-D and their receptors VEGFR1, VEGFR2 and VEGFR3. The Atu027 doses based on the siRNA content are given in the right table. In seven out of nine patients VEGFR1 level were markedly decreased after Atu027 treatment.

In addition to the Atu027 doses indicated in FIG. 5 doses of 0.036 mg/kg Atu027 (based on siRNA content) were administered to three patients whereby two patients showed a marked decrease in the ratio of soluble FLT-1 (sFLT-1) post/pretreatment.

The absolute plasma level of the single analytes VEGF, VEGF-B, VEGF-C, VEGF-D, VEGFR1, VEGFR2 and VEGFR3 are shown in graphs and tables in FIG. 6, FIG. 7, FIG. 8, FIG. 9, FIG. 10, FIG. 11 and FIG. 12. Again, a marked decrease of VEGFR1 concentration after treatment could be detected (FIG. 10) whereas the VEGF, VEGF-B, VEGF-C, VEGF-D, VEGFR2 and VEGFR3 level remained unchanged in most patients and slightly increased or decreased in single individuals.

The features of the present invention disclosed in the specification, the claims and/or the drawings may both separately and in any combination thereof be material for realizing the invention in various forms thereof.

We claim:

1. A method of treating a subject and determining the responsiveness of the subject to treatment with a protein kinase N beta (PKN3) inhibitor comprising:

determining the level of a VEGFR1 or of a nucleic acid coding for a VEGFR1 in a sample from the subject prior to the treatment of said subject, administering a PKN3 inhibitor to said subject having a disease treatable with said PKN3 inhibitor;

determining the level of a VEGFR1 or of a nucleic acid coding for a VEGFR1 in a sample from the subject after the subject has been subjected to the method of treatment; and identifying the subject as a responder to said treatment with said PKN3 inhibitor if the level of a VEGFR1 or a nucleic acid coding for a VEGFR1 in a sample from the subject after the subject having been subjected to the method of treatment is decreased compared to the level of a VEGFR1 or a nucleic acid coding for a VEGFR1 in a sample from the subject prior to the subject having being subjected to the method of treatment; and administering said PKN3 inhibitor to a subject identified as a responder to said treatment.

2. The method according to claim 1, wherein the decrease in level of the VEGFR1 or the nucleic acid coding for the VEGFR1 is a decrease of 10% or more, of 20% or more, 40% or more, 60% or more or 80% or more.

3. The method according to claim 1, wherein the VEGFR1 is VEGFR1, VEGFR1 variant 2, VEGFR1 variant 1, VEGFR1 variant 3, VEGFR1 variant 4, soluble VEGFR1, or soluble VEGFR1 variant 2 or is a nucleic acid encoding VEGFR1, VEGFR1 variant 2, VEGFR1 variant 1, VEGFR1 variant 3, VEGFR1 variant 4, soluble VEGFR1, or soluble VEGFR1 variant 2.

4. The method according to claim 1, wherein the PKN3 inhibitor is an siRNA as follows:

```
                                        (SEQ ID NO: 11)
5' 5u8u7c6g8a6g5c7u7a6g5c5 3'

                                        (SEQ ID NO: 12)
3' a6c6g8u7c5u7a8g6g5u7a8a 5'
```

with unmodified ribonucleotides being as indicated and modified ribonucleotides being represented as follows:

5: 2'-O-Methyl-u,
6: 2'-O-Methyl-a,
7: 2'-O-Methyl-c,
8: 2'-O-Methyl-g.

* * * * *

UNITED STATES PATENT AND TRADEMARK OFFICE

CERTIFICATE OF CORRECTION

PATENT NO. : 9,133,515 B2
APPLICATION NO. : 13/894650
DATED : September 15, 2015
INVENTOR(S) : Klaus Giese et al.

It is certified that error appears in the above-identified patent and that said Letters Patent is hereby corrected as shown below:

IN THE SPECIFICATION

Column 7,
Line 55, "29$^{th}$ and 30$^{th}$" should read --29$^{th}$, 30$^{th}$--.

Column 30,
Lines 18-19, "((β-(L-arginyl)-2,3-L-diaminopropionic acid-N-palmityl-N-oleyl-amide tri-hydrochloride)" should read --(β-(L-arginyl)-2,3-L-diaminopropionic acid-N-palmityl-N-oleyl-amide tri-hydrochloride)--.

Signed and Sealed this
Twenty-second Day of March, 2016

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 687
<212> TYPE: PRT
<213> ORGANISM: Homo sapiens
<220> FEATURE:
<221> NAME/KEY: MISC_FEATURE
<222> LOCATION: (1)..(687)
<223> OTHER INFORMATION: Soluble VEGFR1

<400> SEQUENCE: 1

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160
```

```
Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575
```

```
Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685


<210> SEQ ID NO 2
<211> LENGTH: 6499
<212> TYPE: DNA
<213> ORGANISM: Homo sapiens
<220> FEATURE:
<221> NAME/KEY: misc_feature
<222> LOCATION: (1)..(6499)
<223> OTHER INFORMATION: Soluble VEGFR1

<400> SEQUENCE: 2

atcgaggtcc gcgggaggct cggagcgcgc caggcggaca ctcctctcgg ctcctccccg     60

gcagcggcgg cggctcggag cgggctccgg ggctcgggtg cagcggccag cgggcgcctg    120

gcggcgagga ttacccgggg aagtggttgt ctcctggctg gagccgcgag acgggcgctc    180

agggcgcggg gccggcggcg gcgaacgaga ggacggactc tggcggccgg gtcgttggcc    240

gcggggagcg cgggcaccgg gcgagcaggc cgcgtcgcgc tcaccatggt cagctactgg    300

gacaccgggg tcctgctgtg cgcgctgctc agctgtctgc ttctcacagg atctagttca    360

ggttcaaaat taaaagatcc tgaactgagt ttaaaaggca cccagcacat catgcaagca    420

ggccagacac tgcatctcca atgcaggggg gaagcagccc ataaatggtc tttgcctgaa    480

atggtgagta aggaaagcga aaggctgagc ataactaaat ctgcctgtgg aagaaatggc    540

aaacaattct gcagtacttt aaccttgaac acagctcaag caaaccacac tggcttctac    600

agctgcaaat atctagctgt acctacttca aagaagaagg aaacagaatc tgcaatctat    660

atatttatta gtgatacagg tagacctttc gtagagatgt acagtgaaat ccccgaaatt    720

atacacatga ctgaaggaag ggagctcgtc attccctgcc gggttacgtc acctaacatc    780

actgttactt taaaaaagtt tccacttgac actttgatcc ctgatggaaa acgcataatc    840

tgggacagta gaaagggctt catcatatca aatgcaacgt acaaagaaat agggcttctg    900

acctgtgaag caacagtcaa tgggcatttg tataagacaa actatctcac acatcgacaa    960

accaatacaa tcatagatgt ccaaataagc acaccacgcc cagtcaaatt acttagaggc   1020

catactcttg tcctcaattg tactgctacc actcccttga acacgagagt tcaaatgacc   1080

tggagttacc ctgatgaaaa aaataagaga gcttccgtaa ggcgacgaat tgaccaaagc   1140

aattcccatg ccaacatatt ctacagtgtt cttactattg acaaaatgca gaacaaagac   1200

aaaggacttt atacttgtcg tgtaaggagt ggaccatcat tcaaatctgt taacacctca   1260

gtgcatatat atgataaagc attcatcact gtgaaacatc gaaaacagca ggtgcttgaa   1320

accgtagctg gcaagcggtc ttaccggctc tctatgaaag tgaaggcatt tccctcgccg   1380
```

-continued

```
gaagttgtat ggttaaaaga tgggttacct gcgactgaga aatctgctcg ctatttgact   1440
cgtggctact cgttaattat caaggacgta actgaagagg atgcagggaa ttatacaatc   1500
ttgctgagca taaaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc accccctgtaa ccataatcat tccgaagcaa ggtgtgactt ttgttccaat   1740
aatgaagagt cctttatcct ggatgctgac agcaacatgg gaaacagaat tgagagcatc   1800
actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt ttcatgttaa cttggaaaaa   1980
atgccgacgg aaggagagga cctgaaactg tcttgcacag ttaacaagtt cttatacaga   2040
gacgttactt ggattttact gcggacagtt aataacagaa caatgcacta cagtattagc   2100
aagcaaaaaa tggccatcac taaggagcac tccatcactc ttaatcttac catcatgaat   2160
gtttccctgc aagattcagg cacctatgcc tgcagagcca ggaatgtata cacaggggaa   2220
gaaatcctcc agaagaaaga aattacaatc agaggtgagc actgcaacaa aaaggctgtt   2280
ttctctcgga tctccaaatt taaaagcaca aggaatgatt gtaccacaca aagtaatgta   2340
aaacattaaa ggactcatta aaaagtaaca gttgtctcat atcatcttga tttattgtca   2400
ctgttgctaa ctttcaggct cggaggagat gctcctccca aaatgagttc ggagatgata   2460
gcagtaataa tgagaccccc gggccccagc tctgggcccc ccattcaggc cgagggggct   2520
gctccggggg gccgacttgg tgcacgtttg gatttggagg atccctgcac tgccttctct   2580
gtgtttgttg ctcttgctgt tttctcctgc ctgataaaca acaacttggg atgatccttt   2640
ccttccattt tgatgccaac ctctttttat ttttaagtgt tgaagctgca caaactgaat   2700
aatttaaaca aatgctggtt tctgccaaag atggacacga ataagttaat tttccagctc   2760
agaatgagta cagttgaatt tgagactctg tcggacttct gcctggtttt atttgggact   2820
atttcatctg ctcttgattt gtaaatagca cctggatagc aagttataat gcttatttat   2880
ttgaaaatgc tttttttttt tttacgttaa gcacatttat cttgaactgg agcttctaaa   2940
atgggcccca ggggtgcaag atgttggtgt aattcagaga tagtaaaggt ttatcgcagt   3000
gtgaattata agagtccatc caaatcaacg tcccctccct cctctcatgc gatccaggta   3060
attatgcagt tagtgccaca gtagactagc ctagcaaagg gtttgctcct tgctgtctct   3120
gactgcacca cacagctatt gatggcagct gaaagaaagt ggatcatgcc ttaattttaa   3180
atattcctgt cctctggtta ttattttaag gaacttcatc atgttaaaat gacagcattc   3240
aaaggtgtac cacaatcaat ttatcaagga aataaaggct attgtaacca gagatttaat   3300
gcattcttct aaatgtaaat ttaaaatttg ccctttaaaa aagtccactt tccccatatg   3360
caaatgttaa taggattttt atggggatta agaagcggca aaactacaga agcagaattc   3420
aaagtaattt aaaaaataca caccagtttt aaatcaagag aagttgtaat ctcttgtttt   3480
aagcttgcgt ttgagggaaa atgacttttt caccaattta atatgcattg ttctgttgtt   3540
tttatttatg attgatcatt atatgtgact tgcataaact atttaaaaaa aaaaactata   3600
atgaccaaaa tagccatggc tgagaaacac agtggctggg cagttcaata ggaggtgaca   3660
atatgacaac ttctcaagct tgggaactca ccagactgtt tcctccttta ggtaacagat   3720
tctgtcccac ggctaaactt gtctttcacg tgggaattgc ttttgtcaaa cgtgaaagag   3780
```

```
taaacaatag catttcccca gaatgccagt tttatggagc cccaaatgct ctgaaaacaa   3840
ttagtaacct ggaagttgtc agcccaaagg aaagaaaaat caattgtatc ttgaaatttt   3900
acctatggct ctttggcctg gcttctttgt tcattataag ttagtgtgtt ccttcaggaa   3960
acaatgcctt aataccatag aacatggggg ccttaatagt tgctaacatt aaaaaagcaa   4020
acagaatgat tgagggatcc ttatgaaaac aaaatggtga attggacatg cagaacctac   4080
catttccttc ccctgtttgc aatttttgtg gggaggggag gatgttagta tttacaaaag   4140
atgattttaa gaacttccaa gagatgagtt taagaattcc atagagtatt agttgttcac   4200
tgtgtaatta atccttccgg agagtctttt tttttttttt taaagaaact tttgggtggg   4260
ttttgttttt tattagttac cctaggggta tgttaccctg ggtatgaag ggaggtgaag    4320
ataacggagg ggggagaaaa aaaaaaggag aaaaaaggag cctaaaatgg ggaataattg   4380
aaatggaaca gggggtgtga ggctggttcc tcagtcccca ttccaaacgg aggatagaag   4440
ctgtgtattt atgtgacctg gcagatctct ggggccataa cactgaaaag tgaaagaacc   4500
tggtgggcag ctatctttgg ctactgataa ccagcagaaa tgtctgttaa ttctgatttt   4560
ctcaatttga agggatcagc tacactgtta aattttggaa agccactacc tacttccatc   4620
aagtaactta ggtttcgaaa tatgggttca acgcacctcc cttattcaaa atgtcaaaat   4680
agattattat aatgtataaa gtaagaattg acaaaatatg attcttgggt tgattggtca   4740
tttagaaact agccaaaagt gagactttta atgtagaaca tttttcagaa atgggtacaa   4800
agaaaaatgc atattactgt atatttcaga gtgtttatgt gaaccttgta tttaattgag   4860
agtcccatgt acgttctgca gcctttttgc tgcttctatc atctgaagtt tgtgtagtac   4920
aaataaggcc tttgggattc ttaatgacat ttatgttaaa atgttctctt ctctttaaac   4980
accgttttcc aatccacctg tcagggagtc caaatcgtgt ctgtgttgat gatgctatac   5040
tttgtagcta gaaaaacaat tttagtgttg tgggctctgt attcagactt cctttttaca   5100
agaccgatgg gcagtgatag attattttat catatttaat gcatgggaaa tagtgtgctg   5160
aggaagctat taaaagtata actcagtgaa ttgggtctga gttttaaatg agatatttca   5220
aaattggctt gccactgtaa aagcgactaa ataataatat gatactgttc tttatgatct   5280
tgtcatgttt cactgatatg tttggggtct tcactatgta aaaaatgtca aaattgtaat   5340
gagcaagcat gtacaagtag tcgtaaatca aaggttttaa acaggactgc attttcaatt   5400
aggaaaagct gtttggcaga tagcatccaa tgcaaaaaca gaaatatcgt aacgttctgc   5460
ttagtgggca agataagata ggaaagacat gctcaaagag gcaaaagaat cattgctatc   5520
attcattcta cactagtttg aagaagtttt tgtacatcag agcacttcct tcagcacact   5580
tttttgcctt cagatttcat tttttataaa atgagaagac taatgataaa ctgtagaaat   5640
caaaatttat tgagaaatct gtttctccta acagatagta accctgccat gatatactac   5700
ttcaacaatg ttataaaatt tatgtgataa tatacatttt aacctgggat ttctaaattg   5760
ctttaacaaa tgctaatcct gagagttgcc ctgcaggact caaaagggaa aggttttggg   5820
acgtggcaga accctgcagg gacatggaat taaggccatt gcaatgtatc atctttgtag   5880
cattgtcatc actcctaagc tgccttcaca gttttagtac actaagatga ggaaatcgaa   5940
aatgggcaga gaaagctcat actgtataat tgaagacagt gacagagaac gtgtcagtta   6000
tgccaaaact cttttgattt ctgttccagg atttccaaca agaggggaaa ggaatgactt   6060
gggagggtgg gaaagacatt aggagttgtt tttattttt accttggaag ctttagctac    6120
```

```
caatccagta ccctcctaac tagaatgtat acacatcagc aggactgact gactacttca   6180

ttagagatat actgtactca ttgggggcct tgggggtact gctgttctta tgtgggattt   6240

taatgttgta atgtattgca tcttaatgta ttgaattcat tttgttgtac tatattggtt   6300

ggcattttat taaaataaat tgtattgtat catatttgta tgttttaaga gaaaataata   6360

taaaatacaa tatttgtact attatatagt gcaaaaacta caaatctgtg cctctgcctc   6420

ttgaattaat tctttggttg cttgcatttg ggaagggaat ggagaaagga aagaaccaat   6480

aaagctttca aagttcaag                                                6499


<210> SEQ ID NO 3
<211> LENGTH: 1338
<212> TYPE: PRT
<213> ORGANISM: Homo sapiens
<220> FEATURE:
<221> NAME/KEY: MISC_FEATURE
<222> LOCATION: (1)..(1338)
<223> OTHER INFORMATION: VEGFR1 variant 3

<400> SEQUENCE: 3

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285
```

```
Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700
```

```
Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                 1000                1005

Gly Met  Glu Phe Leu Ser Ser  Arg Lys Cys Ile His  Arg Asp Leu
    1010                1015                1020

Ala Ala  Arg Asn Ile Leu Leu  Ser Glu Asn Asn Val  Val Lys Ile
    1025                1030                1035

Cys Asp  Phe Gly Leu Ala Arg  Asp Ile Tyr Lys Asn  Pro Asp Tyr
    1040                1045                1050

Val Arg  Lys Gly Asp Thr Arg  Leu Pro Leu Lys Trp  Met Ala Pro
    1055                1060                1065

Glu Ser  Ile Phe Asp Lys Ile  Tyr Ser Thr Lys Ser  Asp Val Trp
    1070                1075                1080

Ser Tyr  Gly Val Leu Leu Trp  Glu Ile Phe Ser Leu  Gly Gly Ser
    1085                1090                1095

Pro Tyr  Pro Gly Val Gln Met  Asp Glu Asp Phe Cys  Ser Arg Leu
    1100                1105                1110

Arg Glu  Gly Met Arg Met Arg  Ala Pro Glu Tyr Ser  Thr Pro Glu
```

```
    1115                1120                1125

Ile Tyr  Gln Ile Met Leu Asp  Cys Trp His Arg Asp  Pro Lys Glu
    1130                1135                1140

Arg Pro  Arg Phe Ala Glu Leu  Val Glu Lys Leu Gly  Asp Leu Leu
    1145                1150                1155

Gln Ala  Asn Val Gln Gln Asp  Gly Lys Asp Tyr Ile  Pro Ile Asn
    1160                1165                1170

Ala Ile  Leu Thr Gly Asn Ser  Gly Phe Thr Tyr Ser  Thr Pro Ala
    1175                1180                1185

Phe Ser  Glu Asp Phe Phe Lys  Glu Ser Ile Ser Ala  Pro Lys Phe
    1190                1195                1200

Asn Ser  Gly Ser Ser Asp Asp  Val Arg Tyr Val Asn  Ala Phe Lys
    1205                1210                1215

Phe Met  Ser Leu Glu Arg Ile  Lys Thr Phe Glu Glu  Leu Leu Pro
    1220                1225                1230

Asn Ala  Thr Ser Met Phe Asp  Asp Tyr Gln Gly Asp  Ser Ser Thr
    1235                1240                1245

Leu Leu  Ala Ser Pro Met Leu  Lys Arg Phe Thr Trp  Thr Asp Ser
    1250                1255                1260

Lys Pro  Lys Ala Ser Leu Lys  Ile Asp Leu Arg Val  Thr Ser Lys
    1265                1270                1275

Ser Lys  Glu Ser Gly Leu Ser  Asp Val Ser Arg Pro  Ser Phe Cys
    1280                1285                1290

His Ser  Ser Cys Gly His Val  Ser Glu Gly Lys Arg  Arg Phe Thr
    1295                1300                1305

Tyr Asp  His Ala Glu Leu Glu  Arg Lys Ile Ala Cys  Cys Ser Pro
    1310                1315                1320

Pro Pro  Asp Tyr Asn Ser Val  Val Leu Tyr Ser Thr  Pro Pro Ile
    1325                1330                1335
```

<210> SEQ ID NO 4
<211> LENGTH: 7123
<212> TYPE: DNA
<213> ORGANISM: Homo sapiens
<220> FEATURE:
<221> NAME/KEY: misc_feature
<222> LOCATION: (1)..(7123)
<223> OTHER INFORMATION: VEGFR1 transcript variat 1

<400> SEQUENCE: 4

```
atcgaggtcc gcgggaggct cggagcgcgc caggcggaca ctcctctcgg ctcctccccg     60

gcagcggcgg cggctcggag cgggctccgg ggctcgggtg cagcggccag cgggcgcctg    120

gcggcgagga ttacccgggg aagtggttgt ctcctggctg gagccgcgag acgggcgctc    180

agggcgcggg gccggcggcg gcgaacgaga ggacggactc tggcggccgg gtcgttggcc    240

gcggggagcg cgggcaccgg gcgagcaggc cgcgtcgcgc tcaccatggt cagctactgg    300

gacaccgggg tcctgctgtg cgcgctgctc agctgtctgc ttctcacagg atctagttca    360

ggttcaaaat taaaagatcc tgaactgagt ttaaaaggca cccagcacat catgcaagca    420

ggccagacac tgcatctcca atgcaggggg gaagcagccc ataaatggtc tttgcctgaa    480

atggtgagta aggaaagcga aaggctgagc ataactaaat ctgcctgtgg aagaaatggc    540

aaacaattct gcagtacttt aaccttgaac acagctcaag caaaccacac tggcttctac    600

agctgcaaat atctagctgt acctacttca aagaagaagg aaacagaatc tgcaatctat    660

atatttatta gtgatacagg tagacctttc gtagagatgt acagtgaaat ccccgaaatt    720
```

```
atacacatga ctgaaggaag ggagctcgtc attccctgcc gggttacgtc acctaacatc    780
actgttactt taaaaaagtt tccacttgac actttgatcc ctgatggaaa acgcataatc    840
tgggacagta gaaagggctt catcatatca aatgcaacgt acaaagaaat agggcttctg    900
acctgtgaag caacagtcaa tgggcatttg tataagacaa actatctcac acatcgacaa    960
accaatacaa tcatagatgt ccaaataagc acaccacgcc cagtcaaatt acttagaggc   1020
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt tccctcgccg   1380
gaagttgtat ggttaaaaga tgggttacct gcgactgaga aatctgctcg ctatttgact   1440
cgtggctact cgttaattat caaggacgta actgaagagg atgcagggaa ttatacaatc   1500
ttgctgagca taaaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc accccctgtaa ccataatcat tccgaagcaa ggtgtgactt ttgttccaat   1740
aatgaagagt cctttatcct ggatgctgac agcaacatgg gaaacagaat tgagagcatc   1800
actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt ttcatgttaa cttggaaaaa   1980
atgccgacgg aaggagagga cctgaaactg tcttgcacag ttaacaagtt cttatacaga   2040
gacgttactt ggattttact gcggacagtt aataacagaa caatgcacta cagtattagc   2100
aagcaaaaaa tggccatcac taaggagcac tccatcactc ttaatcttac catcatgaat   2160
gtttccctgc aagattcagg cacctatgcc tgcagagcca ggaatgtata cacaggggaa   2220
gaaatcctcc agaagaaaga aattacaatc agagatcagg aagcaccata cctcctgcga   2280
aacctcagtg atcacacagt ggccatcagc agttccacca ctttagactg tcatgctaat   2340
ggtgtccccg agcctcagat cacttggttt aaaaacaacc acaaaataca acaagagcct   2400
ggaattattt taggaccagg aagcagcacg ctgtttattg aaagagtcac agaagaggat   2460
gaaggtgtct atcactgcaa agccaccaac cagaagggct ctgtggaaag ttcagcatac   2520
ctcactgttc aaggaacctc ggacaagtct aatctggagc tgatcactct aacatgcacc   2580
tgtgtggctg cgactctctt ctggctccta ttaaccctct ttatccgaaa aatgaaaagg   2640
tcttcttctg aaataaagac tgactaccta tcaattataa tggacccaga tgaagttcct   2700
ttggatgagc agtgtgagcg gctcccttat gatgccagca agtgggagtt tgcccgggag   2760
agacttaaac tgggcaaatc acttggaaga ggggcttttg gaaaagtggt tcaagcatca   2820
gcatttggca ttaagaaatc acctacgtgc cggactgtgg ctgtgaaaat gctgaaagag   2880
ggggccacgg ccagcgagta caaagctctg atgactgagc taaaaatctt gacccacatt   2940
ggccaccatc tgaacgtggt taacctgctg ggagcctgca ccaagcaagg agggcctctg   3000
atggtgattg ttgaatactg caaatatgga aatctctcca actacctcaa gagcaaacgt   3060
```

```
gacttatttt ttctcaacaa ggatgcagca ctacacatgg agcctaagaa agaaaaaatg   3120
gagccaggcc tggaacaagg caagaaacca agactagata gcgtcaccag cagcgaaagc   3180
tttgcgagct ccggctttca ggaagataaa agtctgagtg atgttgagga agaggaggat   3240
tctgacggtt tctacaagga gcccatcact atggaagatc tgatttctta cagttttcaa   3300
gtggccagag gcatggagtt cctgtcttcc agaaagtgca ttcatcggga cctggcagcg   3360
agaaacattc ttttatctga gaacaacgtg gtgaagattt gtgattttgg ccttgcccgg   3420
gatatttata agaaccccga ttatgtgaga aaaggagata ctcgacttcc tctgaaatgg   3480
atggctcctg aatctatctt tgacaaaatc tacagcacca agagcgacgt gtggtcttac   3540
ggagtattgc tgtgggaaat cttctcctta ggtgggtctc catacccagg agtacaaatg   3600
gatgaggact tttgcagtcg cctgagggaa ggcatgagga tgagagctcc tgagtactct   3660
actcctgaaa tctatcagat catgctggac tgctggcaca gagacccaaa agaaaggcca   3720
agatttgcag aacttgtgga aaaactaggt gatttgcttc aagcaaatgt acaacaggat   3780
ggtaaagact acatcccaat caatgccata ctgacaggaa atagtgggtt tacatactca   3840
actcctgcct tctctgagga cttcttcaag gaaagtattt cagctccgaa gtttaattca   3900
ggaagctctg atgatgtcag atacgtaaat gctttcaagt tcatgagcct ggaaagaatc   3960
aaaacctttg aagaactttt accgaatgcc acctccatgt ttgatgacta ccagggcgac   4020
agcagcactc tgttggcctc tcccatgctg aagcgcttca cctggactga cagcaaaccc   4080
aaggcctcgc tcaagattga cttgagagta accagtaaaa gtaaggagtc ggggctgtct   4140
gatgtcagca ggcccagttt ctgccattcc agctgtgggc acgtcagcga aggcaagcgc   4200
aggttcacct acgaccacgc tgagctggaa aggaaaatcg cgtgctgctc cccgccccca   4260
gactacaact cggtggtcct gtactccacc ccacccatct agagtttgac acgaagcctt   4320
atttctagaa gcacatgtgt atttataccc ccaggaaact agcttttgcc agtattatgc   4380
atatataagt ttacaccttt atctttccat gggagccagc tgctttttgt gattttttta   4440
atagtgcttt tttttttttg actaacaaga atgtaactcc agatagagaa atagtgacaa   4500
gtgaagaaca ctactgctaa atcctcatgt tactcagtgt tagagaaatc cttcctaaac   4560
ccaatgactt ccctgctcca acccccgcca cctcagggca cgcaggacca gtttgattga   4620
ggagctgcac tgatcaccca atgcatcacg taccccactg ggccagccct gcagcccaaa   4680
acccagggca acaagcccgt tagccccagg gatcactggc tggcctgagc aacatctcgg   4740
gagtcctcta gcaggcctaa gacatgtgag gaggaaaagg aaaaaaagca aaaagcaagg   4800
gagaaaagag aaaccgggag aaggcatgag aaagaatttg agacgcacca tgtgggcacg   4860
gagggggacg gggctcagca atgccatttc agtggcttcc cagctctgac ccttctacat   4920
ttgagggccc agccaggagc agatggacag cgatgagggg acattttctg gattctggga   4980
ggcaagaaaa ggacaaatat ctttttttgga actaaagcaa attttagaac tttacctatg   5040
gaagtggttc tatgtccatt ctcattcgtg gcatgttttg atttgtagca ctgagggtgg   5100
cactcaactc tgagcccata cttttggctc ctctagtaag atgcactgaa aacttagcca   5160
gagttaggtt gtctccaggc catgatggcc ttacactgaa aatgtcacat tctattttgg   5220
gtattaatat atagtccaga cacttaactc aatttcttgg tattattctg ttttgcacag   5280
ttagttgtga aagaaagctg agaagaatga aaatgcagtc ctgaggagag gagttttctc   5340
catatcaaaa cgagggctga tggaggaaaa aggtcaataa ggtcaaggga aaccccgtc   5400
tctataccaa ccaaaccaat tcaccaacac agttgggacc caaaacacag gaagtcagtc   5460
```

```
acgtttcctt ttcatttaat ggggattcca ctatctcaca ctaatctgaa aggatgtgga   5520

agagcattag ctggcgcata ttaagcactt taagctcctt gagtaaaaag gtggtatgta   5580

atttatgcaa ggtatttctc cagttgggac tcaggatatt agttaatgag ccatcactag   5640

aagaaaagcc cattttcaac tgctttgaaa cttgcctggg gtctgagcat gatgggaata   5700

gggagacagg gtaggaaagg gcgcctactc ttcagggtct aaagatcaag tgggccttgg   5760

atcgctaagc tggctctgtt tgatgctatt tatgcaagtt agggtctatg tatttatgat   5820

gtctgcacct tctgcagcca gtcagaagct ggagaggcaa cagtggattg ctgcttcttg   5880

gggagaagag tatgcttcct tttatccatg taatttaact gtagaacctg agctctaagt   5940

aaccgaagaa tgtatgcctc tgttcttatg tgccacatcc ttgtttaaag gctctctgta   6000

tgaagagatg ggaccgtcat cagcacattc cctagtgagc ctactggctc ctggcagcgg   6060

cttttgtgga agactcacta gccagaagag aggagtggga cagtcctctc caccaagatc   6120

taaatccaaa caaaagcagg ctagagccag aagagaggac aaatctttgt tcttcctctt   6180

ctttacatac gcaaaccacc tgtgacagct ggcaatttta taaatcaggt aactggaagg   6240

aggttaaaca cagaaaaaag aagacctcag tcaattctct acttttttt tttttccaa   6300

atcagataat agcccagcaa atagtgataa caaataaaac cttagctatt catgtcttga   6360

tttcaataat taattcttaa tcattaagag accataataa atactccttt tcaagagaaa   6420

agcaaaacca ttagaattgt tactcagctc cttcaaactc aggtttgtag catacatgag   6480

tccatccatc agtcaaagaa tggttccatc tggagtctta atgtagaaag aaaaatggag   6540

acttgtaata atgagctagt tacaaagtgc ttgttcatta aaatagcact gaaaattgaa   6600

acatgaatta actgataata ttccaatcat ttgccattta tgacaaaaat ggttggcact   6660

aacaaagaac gagcacttcc tttcagagtt tctgagataa tgtacgtgga acagtctggg   6720

tggaatgggg ctgaaaccat gtgcaagtct gtgtcttgtc agtccaagaa gtgacaccga   6780

gatgttaatt ttagggaccc gtgccttgtt tcctagccca caagaatgca aacatcaaac   6840

agatactcgc tagcctcatt taaattgatt aaaggaggag tgcatctttg gccgacagtg   6900

gtgtaactgt atgtgtgtgt gtgtgtgtgt gtgtgtgtgt gtgtgtgggt gtatgtgtgt   6960

tttgtgcata actatttaag gaaactggaa ttttaaagtt acttttatac aaaccaagaa   7020

tatatgctac agatataaga cagacatggt ttggtcctat atttctagtc atgatgaatg   7080

tattttgtat accatcttca tataataaac ttccaaaaac aca                     7123
```

<210> SEQ ID NO 5
<211> LENGTH: 733
<212> TYPE: PRT
<213> ORGANISM: Homo sapiens
<220> FEATURE:
<221> NAME/KEY: MISC_FEATURE
<222> LOCATION: (1)..(733)
<223> OTHER INFORMATION: VEGFR1 variant 3

<400> SEQUENCE: 5

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
```

```
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480
```

```
Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Glu Leu Tyr Thr Ser Thr Ser Pro Ser Ser Ser Ser Ser Ser Pro
705                 710                 715                 720

Leu Ser Ser Ser Ser Ser Ser Ser Ser Ser Ser Ser Ser
                725                 730
```

<210> SEQ ID NO 6
<211> LENGTH: 2968
<212> TYPE: DNA
<213> ORGANISM: Homo sapiens
<220> FEATURE:
<221> NAME/KEY: misc_feature
<222> LOCATION: (1)..(2968)
<223> OTHER INFORMATION: VEGFR1 transcript variant 3

<400> SEQUENCE: 6

```
atcgaggtcc gcgggaggct cggagcgcgc caggcggaca ctcctctcgg ctcctccccg     60

gcagcggcgg cggctcggag cgggctccgg ggctcgggtg cagcggccag cgggcgcctg    120

gcggcgagga ttacccgggg aagtggttgt ctcctggctg gagccgcgag acgggcgctc    180

agggcgcggg gccggcggcg gcgaacgaga ggacggactc tggcggccgg gtcgttggcc    240

gcggggagcg cgggcaccgg gcgagcaggc cgcgtcgcgc tcaccatggt cagctactgg    300

gacaccgggg tcctgctgtg cgcgctgctc agctgtctgc ttctcacagg atctagttca    360

ggttcaaaat taaaagatcc tgaactgagt ttaaaaggca cccagcacat catgcaagca    420

ggccagacac tgcatctcca atgcaggggg gaagcagccc ataaatggtc tttgcctgaa    480

atggtgagta aggaaagcga aaggctgagc ataactaaat ctgcctgtgg aagaaatggc    540
```

```
aaacaattct gcagtacttt aaccttgaac acagctcaag caaaccacac tggcttctac    600
agctgcaaat atctagctgt acctacttca aagaagaagg aaacagaatc tgcaatctat    660
atatttatta gtgatacagg tagacctttc gtagagatgt acagtgaaat ccccgaaatt    720
atacacatga ctgaaggaag ggagctcgtc attccctgcc gggttacgtc acctaacatc    780
actgttactt taaaaaagtt tccacttgac actttgatcc ctgatggaaa acgcataatc    840
tgggacagta gaaagggctt catcatatca aatgcaacgt acaaagaaat agggcttctg    900
acctgtgaag caacagtcaa tgggcatttg tataagacaa actatctcac acatcgacaa    960
accaatacaa tcatagatgt ccaaataagc acaccacgcc cagtcaaatt acttagaggc   1020
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt tccctcgccg   1380
gaagttgtat ggttaaaaga tgggttacct gcgactgaga aatctgctcg ctatttgact   1440
cgtggctact cgttaattat caaggacgta actgaagagg atgcagggaa ttatacaatc   1500
ttgctgagca taaaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc accccctgtaa ccataatcat tccgaagcaa ggtgtgactt ttgttccaat   1740
aatgaagagt cctttatcct ggatgctgac agcaacatgg gaaacagaat tgagagcatc   1800
actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt ttcatgttaa cttggaaaaa   1980
atgccgacgg aaggagagga cctgaaactg tcttgcacag ttaacaagtt cttatacaga   2040
gacgttactt ggattttact gcggacagtt aataacagaa caatgcacta cagtattagc   2100
aagcaaaaaa tggccatcac taaggagcac tccatcactc ttaatcttac catcatgaat   2160
gtttccctgc aagattcagg cacctatgcc tgcagagcca ggaatgtata cacaggggaa   2220
gaaatcctcc agaagaaaga aattacaatc agagatcagg aagcaccata cctcctgcga   2280
aacctcagtg atcacacagt ggccatcagc agttccacca ctttagactg tcatgctaat   2340
ggtgtccccg agcctcagat cacttggttt aaaaacaacc acaaaataca acaagagcct   2400
gaactgtata catcaacgtc accatcgtca tcgtcatcat caccattgtc atcatcatca   2460
tcatcgtcat catcatcatc atcatagcta tcatcattat catcatcatc atcatcatca   2520
tcatagctac catttattga aaactattat gtgtcaactt caaagaactt atcctttagt   2580
tggagagcca agacaatcat aacaataaca aatggccggg catggtggct cacgcctgta   2640
atcccagcac tttgggaggc caaggcaggt ggatcatttg aggtcaggag ttcaagacca   2700
gcctgaccaa gatggtgaaa tgctgtctct attaaaaata caaaattagc caggcatggt   2760
ggctcatgcc tgtaatgcca gctactcggg aggctgagac aggagaatca cttgaaccca   2820
ggaggcagag gttgcaggga gccgagatcg tgtactgcac tccagcctgg gcaacaagag   2880
cgaaactccg tctcaaaaaa caaataaata aataaataaa taaacagaca aaattcactt   2940
```

```
tttattctat taaacttaac atacatgc                              2968


<210> SEQ ID NO 7
<211> LENGTH: 541
<212> TYPE: PRT
<213> ORGANISM: Homo sapiens
<220> FEATURE:
<221> NAME/KEY: MISC_FEATURE
<222> LOCATION: (1)..(541)
<223> OTHER INFORMATION: VEGFR1 variant 4

<400> SEQUENCE: 7

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
```

```
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Leu Pro Pro Ala Asn Ser Ser Phe Met Leu Pro
        515                 520                 525

Pro Thr Ser Phe Ser Ser Asn Tyr Phe His Phe Leu Pro
    530                 535                 540


<210> SEQ ID NO 8
<211> LENGTH: 1911
<212> TYPE: DNA
<213> ORGANISM: Homo sapiens
<220> FEATURE:
<221> NAME/KEY: misc_feature
<222> LOCATION: (1)..(1911)
<223> OTHER INFORMATION: VEGFRa transcript variant 4

<400> SEQUENCE: 8

atcgaggtcc gcgggaggct cggagcgcgc caggcggaca ctcctctcgg ctcctccccg      60

gcagcggcgg cggctcggag cgggctccgg ggctcgggtg cagcggccag cgggcgcctg     120

gcggcgagga ttacccgggg aagtggttgt ctcctggctg gagccgcgag acgggcgctc     180

agggcgcggg gccggcggcg gcgaacgaga ggacggactc tggcggccgg gtcgttggcc     240

gcggggagcg cgggcaccgg gcgagcaggc cgcgtcgcgc tcaccatggt cagctactgg     300

gacaccgggg tcctgctgtg cgcgctgctc agctgtctgc ttctcacagg atctagttca     360

ggttcaaaat taaaagatcc tgaactgagt ttaaaaggca cccagcacat catgcaagca     420

ggccagacac tgcatctcca atgcaggggg gaagcagccc ataaatggtc tttgcctgaa     480

atggtgagta aggaaagcga aaggctgagc ataactaaat ctgcctgtgg aagaaatggc     540

aaacaattct gcagtacttt aaccttgaac acagctcaag caaaccacac tggcttctac     600

agctgcaaat atctagctgt acctacttca aagaagaagg aaacagaatc tgcaatctat     660

atatttatta gtgatacagg tagacctttc gtagagatgt acagtgaaat ccccgaaatt     720

atacacatga ctgaaggaag ggagctcgtc attccctgcc gggttacgtc acctaacatc     780

actgttactt taaaaaagtt tccacttgac actttgatcc ctgatggaaa acgcataatc     840

tgggacagta gaaagggctt catcatatca aatgcaacgt acaaagaaat agggcttctg     900
```

```
acctgtgaag caacagtcaa tggcatttg tataagacaa actatctcac acatcgacaa    960
accaatacaa tcatagatgt ccaaataagc acaccacgcc cagtcaaatt acttagaggc   1020
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt tccctcgccg   1380
gaagttgtat ggttaaaaga tgggttacct gcgactgaga aatctgctcg ctatttgact   1440
cgtggctact cgttaattat caaggacgta actgaagagg atgcagggaa ttatacaatc   1500
ttgctgagca taaaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc acccctgtaa ccataatcat tccgaagcaa ggtgtgactt ttgttccaat   1740
aatgaagagt cctttatcct ggatgctgac agcaacatgg gaaacagaat tgagagcatc   1800
actcagcgca tggcaataat agaaggaaag aataagcttc caccagctaa cagttctttc   1860
atgttgccac ctacaagctt ctcttccaac tacttccatt tccttccgtg a             1911
```

<210> SEQ ID NO 9
<211> LENGTH: 889
<212> TYPE: PRT
<213> ORGANISM: Homo sapiens
<220> FEATURE:
<221> NAME/KEY: MISC_FEATURE
<222> LOCATION: (1)..(880)
<223> OTHER INFORMATION: PKN3

<400> SEQUENCE: 9

```
Met Glu Glu Gly Ala Pro Arg Gln Pro Gly Pro Ser Gln Trp Pro Pro
1               5                   10                  15

Glu Asp Glu Lys Glu Val Ile Arg Arg Ala Ile Gln Lys Glu Leu Lys
            20                  25                  30

Ile Lys Glu Gly Val Glu Asn Leu Arg Arg Val Ala Thr Asp Arg Arg
        35                  40                  45

His Leu Gly His Val Gln Gln Leu Leu Arg Ser Ser Asn Arg Arg Leu
    50                  55                  60

Glu Gln Leu His Gly Glu Leu Arg Glu Leu His Ala Arg Ile Leu Leu
65                  70                  75                  80

Pro Gly Pro Gly Pro Gly Pro Ala Glu Pro Val Ala Ser Gly Pro Arg
                85                  90                  95

Pro Trp Ala Glu Gln Leu Arg Ala Arg His Leu Glu Ala Leu Arg Arg
            100                 105                 110

Gln Leu His Val Glu Leu Lys Val Lys Gln Gly Ala Glu Asn Met Thr
        115                 120                 125

His Thr Cys Ala Ser Gly Thr Pro Lys Glu Arg Lys Leu Leu Ala Ala
    130                 135                 140

Ala Gln Gln Met Leu Arg Asp Ser Gln Leu Lys Val Ala Leu Leu Arg
145                 150                 155                 160

Met Lys Ile Ser Ser Leu Glu Ala Ser Gly Ser Pro Glu Pro Gly Pro
                165                 170                 175
```

```
Glu Leu Leu Ala Glu Glu Leu Gln His Arg Leu His Val Glu Ala Ala
            180                 185                 190

Val Ala Glu Gly Ala Lys Asn Val Val Lys Leu Leu Ser Ser Arg Arg
        195                 200                 205

Thr Gln Asp Arg Lys Ala Leu Ala Glu Ala Gln Ala Gln Leu Gln Glu
    210                 215                 220

Ser Ser Gln Lys Leu Asp Leu Leu Arg Leu Ala Leu Glu Gln Leu Leu
225                 230                 235                 240

Glu Gln Leu Pro Pro Ala His Pro Leu Arg Ser Arg Val Thr Arg Glu
                245                 250                 255

Leu Arg Ala Ala Val Pro Gly Tyr Pro Gln Pro Ser Gly Thr Pro Val
            260                 265                 270

Lys Pro Thr Ala Leu Thr Gly Thr Leu Gln Val Arg Leu Leu Gly Cys
        275                 280                 285

Glu Gln Leu Leu Thr Ala Val Pro Gly Arg Ser Pro Ala Ala Ala Leu
    290                 295                 300

Ala Ser Ser Pro Ser Glu Gly Trp Leu Arg Thr Lys Ala Lys His Gln
305                 310                 315                 320

Arg Gly Arg Gly Glu Leu Ala Ser Glu Val Leu Ala Val Leu Lys Val
                325                 330                 335

Asp Asn Arg Val Val Gly Gln Thr Gly Trp Gly Gln Val Ala Glu Gln
            340                 345                 350

Ser Trp Asp Gln Thr Phe Val Ile Pro Leu Glu Arg Ala Arg Glu Leu
        355                 360                 365

Glu Ile Gly Val His Trp Arg Asp Trp Arg Gln Leu Cys Gly Val Ala
    370                 375                 380

Phe Leu Arg Leu Glu Asp Phe Leu Asp Asn Ala Cys His Gln Leu Ser
385                 390                 395                 400

Leu Ser Leu Val Pro Gln Gly Leu Leu Phe Ala Gln Val Thr Phe Cys
                405                 410                 415

Asp Pro Val Ile Glu Arg Arg Pro Arg Leu Gln Arg Gln Glu Arg Ile
            420                 425                 430

Phe Ser Lys Arg Arg Gly Gln Asp Phe Leu Arg Arg Ser Gln Met Asn
        435                 440                 445

Leu Gly Met Ala Ala Trp Gly Arg Leu Val Met Asn Leu Leu Pro Pro
    450                 455                 460

Cys Ser Ser Pro Ser Thr Ile Ser Pro Pro Lys Gly Cys Pro Arg Thr
465                 470                 475                 480

Pro Thr Thr Leu Arg Glu Ala Ser Asp Pro Ala Thr Pro Ser Asn Phe
                485                 490                 495

Leu Pro Lys Lys Thr Pro Leu Gly Glu Glu Met Thr Pro Pro Pro Lys
            500                 505                 510

Pro Pro Arg Leu Tyr Leu Pro Gln Glu Pro Thr Ser Glu Glu Thr Pro
        515                 520                 525

Arg Thr Lys Arg Pro His Met Glu Pro Arg Thr Arg Arg Gly Pro Ser
    530                 535                 540

Pro Pro Ala Ser Pro Thr Arg Lys Pro Pro Arg Leu Gln Asp Phe Arg
545                 550                 555                 560

Cys Leu Ala Val Leu Gly Arg Gly His Phe Gly Lys Val Leu Leu Val
                565                 570                 575

Gln Phe Lys Gly Thr Gly Lys Tyr Tyr Ala Ile Lys Ala Leu Lys Lys
            580                 585                 590
```

```
Gln Glu Val Leu Ser Arg Asp Glu Ile Glu Ser Leu Tyr Cys Glu Lys
        595                 600                 605

Arg Ile Leu Glu Ala Val Gly Cys Thr Gly His Pro Phe Leu Leu Ser
    610                 615                 620

Leu Leu Val Cys Phe Gln Thr Ser Ser His Ala Arg Phe Val Thr Glu
625                 630                 635                 640

Phe Val Pro Gly Gly Asp Leu Met Met Gln Ile His Glu Asp Val Phe
                645                 650                 655

Pro Glu Pro Gln Ala Arg Phe Tyr Val Ala Cys Val Val Leu Gly Leu
            660                 665                 670

Gln Phe Leu His Glu Lys Lys Ile Ile Tyr Arg Asp Leu Lys Leu Asp
        675                 680                 685

Asn Leu Leu Leu Asp Ala Gln Gly Phe Leu Lys Ile Ala Asp Phe Gly
    690                 695                 700

Leu Cys Lys Glu Gly Ile Gly Phe Gly Asp Arg Thr Ser Thr Phe Cys
705                 710                 715                 720

Gly Thr Pro Glu Phe Leu Ala Pro Glu Val Leu Thr Gln Glu Ala Tyr
                725                 730                 735

Thr Gln Ala Val Asp Trp Trp Ala Leu Gly Val Leu Leu Tyr Glu Met
            740                 745                 750

Leu Val Gly Glu Cys Pro Phe Pro Gly Asp Thr Glu Glu Glu Val Phe
        755                 760                 765

Asp Cys Ile Val Asn Met Asp Ala Pro Tyr Pro Gly Phe Leu Ser Val
    770                 775                 780

Gln Gly Leu Glu Phe Ile Gln Lys Leu Leu Gln Lys Cys Pro Glu Lys
785                 790                 795                 800

Arg Leu Gly Ala Gly Glu Gln Asp Ala Glu Glu Ile Lys Val Gln Pro
                805                 810                 815

Phe Phe Arg Thr Thr Asn Trp Gln Ala Leu Leu Ala Arg Thr Ile Gln
            820                 825                 830

Pro Pro Phe Val Pro Thr Leu Cys Gly Pro Ala Asp Leu Arg Tyr Phe
        835                 840                 845

Glu Gly Glu Phe Thr Gly Leu Pro Pro Ala Leu Thr Pro Pro Ala Pro
    850                 855                 860

His Ser Leu Leu Thr Ala Arg Gln Gln Ala Ala Phe Arg Asp Phe Asp
865                 870                 875                 880

Phe Val Ser Glu Arg Phe Leu Glu Pro
                885
```

```
<210> SEQ ID NO 10
<211> LENGTH: 2670
<212> TYPE: DNA
<213> ORGANISM: Homo sapiens
<220> FEATURE:
<221> NAME/KEY: misc_feature
<222> LOCATION: (1)..(2670)
<223> OTHER INFORMATION: PKN3

<400> SEQUENCE: 10

atggaggagg gggcgccgcg gcagcctggg ccgagccagt ggcccccaga ggatgagaag      60

gaggtgatcc gccgggccat ccagaaagag ctgaagatca aggagggggt ggagaacctg     120

cggcgcgtgg ccacagaccg ccgccacttg ggccatgtgc agcagctgct gcggtcctcc     180

aaccgccgcc tggagcagct gcatggcgag ctgcgggagc tgcacgcccg aatcctgctg     240

cccggccctg ggcctggccc agctgagcct gtggcctcag gaccccggcc gtgggcagag     300
```

```
cagctcaggg ctcggcacct agaggctctc cggaggcagc tgcatgtgga gctgaaggtg    360
aaacaggggg ctgagaacat gacccacacg tgcgccagtg gcacccccaa ggagaggaag    420
ctccttgcag ctgcccagca gatgctgcgg gacagccagc tgaaggtggc cctgctgcgg    480
atgaagatca gcagcctgga ggccagtggg tccccggagc cagggcctga gctactggcg    540
gaggagctac agcatcgact gcacgttgag gcagcggtgg ctgagggcgc caagaacgtg    600
gtgaaactgc ttagtagccg gagaacacag gaccgcaagg cactggctga ggcccaggcc    660
cagctacagg agtcctctca gaaactggac ctcctgcgcc tggccttgga gcagctgctg    720
gagcaactgc ctcctgccca ccctttgcgc agcagagtga cccgagagtt gcgggctgcg    780
gtgcctggat acccccagcc ttcagggaca cctgtgaagc ccaccgccct aacagggaca    840
ctgcaggtcc gcctcctggg ctgtgaacag ttgctgacag ccgtgcctgg gcgctcccca    900
gcggccgcac tggccagcag cccctccgag ggctggcttc ggaccaaggc caagcaccag    960
cgtggccgag gcgagcttgc cagtgaggtg ctggctgtgc taaaggtgga caaccgtgtt   1020
gtggggcaga cgggctgggg gcaggtggcc gaacagtcct gggaccagac ctttgtcatc   1080
ccactggagc gagcccgtga gctggagatt ggggtacact ggcgggactg gcggcagcta   1140
tgtggcgtgg ccttcctgag acttgaagac ttcctggaca atgcctgtca ccaactgtcc   1200
ctcagcctgg taccgcaggg actgcttttt gcccaggtga ccttctgcga tcctgtcatt   1260
gagaggcggc cccggctgca gaggcaggaa cgcatcttct ctaaacgcag aggccaggac   1320
ttcctgaggc gttcgcagat gaacctcggc atggcggcct gggggcgcct cgtcatgaac   1380
ctgctgcccc cctgcagctc ccgagcaca atcagccccc ctaaaggatg ccctcggacc   1440
ccaacaacac tgcgagaggc ctctgaccct gccactccca gtaatttcct gcccaagaag   1500
accccccttgg gtgaagagat gacaccccca cccaagcccc cacgcctcta cctcccccag   1560
gagccaacat ccgaggagac tccgcgcacc aaacgtcccc atatggagcc taggactcga   1620
cgtgggccat ctccaccagc ctcccccacc aggaaacccc ctcggcttca ggacttccgc   1680
tgcttagctg tgctgggccg ggacactttt gggaaggtcc tcctggtcca gttcaagggg   1740
acagggaaat actacgccat caaagcactg aagaagcagg aggtgctcag ccgggacgag   1800
atagagagcc tgtactgcga gaagcggatc ctggaggctg tgggctgcac agggcaccct   1860
ttcctgctct ccctccttgt ctgcttccag acctccagcc atgcccgctt tgtgactgag   1920
tttgtgcctg gtggtgacct catgatgcag atccacgagg atgtcttccc cgagccccag   1980
gcccgcttct acgtggcttg tgttgtcctg ggctgcagt tcttacacga gaagaagatc   2040
atttacaggg acctgaagtt ggataacctt ctgctggatg cccagggatt cctgaagatc   2100
gcagactttg gactctgcaa ggaagggatc ggcttcgggg accggactag caccttctgt   2160
ggcaccccgg agttcctggc tcccgaggtg ctgacccagg aggcatacac acaggccgtc   2220
gactggtggg cgctgggtgt gctgctctac gagatgctgg tgggtgagtg cccgttccca   2280
ggggacacag aggaagaggt gtttgactgc atcgtcaaca tggacgcccc ctaccccggc   2340
tttctgtcgg tgcaagggct tgagttcatt cagaagctcc tccagaagtg cccggagaag   2400
cgcctcgggg caggtgagca ggatgccgag gagatcaagg tccagccatt cttcaggacc   2460
accaactggc aagccctgct cgcccgcacc atccagcccc ccttcgtgcc taccctgtgt   2520
ggccctgcgg acctgcgcta ctttgagggc gagttcacag ggctgccgcc tgccctgacc   2580
ccacctgcac cccacagcct cctcactgcc cgccaacagg ccgccttccg ggacttcgac   2640
tttgtgtcag agcgattcct ggaaccctga                                   2670
```

<210> SEQ ID NO 11
<211> LENGTH: 23
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-Methyl
<220> FEATURE:
<221> NAME/KEY: misc_feature
<222> LOCATION: (3)..(3)
<223> OTHER INFORMATION: 2'-O-Methyl
<220> FEATURE:
<221> NAME/KEY: misc_feature
<222> LOCATION: (5)..(5)
<223> OTHER INFORMATION: 2'-O-Methyl
<220> FEATURE:
<221> NAME/KEY: misc_feature
<222> LOCATION: (7)..(7)
<223> OTHER INFORMATION: 2'-O-Methyl
<220> FEATURE:
<221> NAME/KEY: misc_feature
<222> LOCATION: (9)..(9)
<223> OTHER INFORMATION: 2'-O-Methyl
<220> FEATURE:
<221> NAME/KEY: misc_feature
<222> LOCATION: (11)..(11)
<223> OTHER INFORMATION: 2'-O-Methyl
<220> FEATURE:
<221> NAME/KEY: misc_feature
<222> LOCATION: (13)..(13)
<223> OTHER INFORMATION: 2'-O-Methyl
<220> FEATURE:
<221> NAME/KEY: misc_feature
<222> LOCATION: (15)..(15)
<223> OTHER INFORMATION: 2'-O-Methyl
<220> FEATURE:
<221> NAME/KEY: misc_feature
<222> LOCATION: (17)..(17)
<223> OTHER INFORMATION: 2'-O-Methyl
<220> FEATURE:
<221> NAME/KEY: misc_feature
<222> LOCATION: (19)..(19)
<223> OTHER INFORMATION: 2'-O-Methyl
<220> FEATURE:
<221> NAME/KEY: misc_feature
<222> LOCATION: (21)..(21)
<223> OTHER INFORMATION: 2'-O-Methyl
<220> FEATURE:
<221> NAME/KEY: misc_feature
<222> LOCATION: (23)..(23)
<223> OTHER INFORMATION: 2'-O-Methyl

<400> SEQUENCE: 11
uuguccagga aguccucaag ucu 23

<210> SEQ ID NO 12
<211> LENGTH: 23
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-O-Methyl
<220> FEATURE:
<221> NAME/KEY: misc_feature
<222> LOCATION: (4)..(4)
<223> OTHER INFORMATION: 2'-O-Methyl
<220> FEATURE:
<221> NAME/KEY: misc_feature
<222> LOCATION: (6)..(6)

<223> OTHER INFORMATION: 2'-O-Methyl
<220> FEATURE:
<221> NAME/KEY: misc_feature
<222> LOCATION: (8)..(8)
<223> OTHER INFORMATION: 2'-O-Methyl
<220> FEATURE:
<221> NAME/KEY: misc_feature
<222> LOCATION: (10)..(10)
<223> OTHER INFORMATION: 2'-O-Methyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(14)
<223> OTHER INFORMATION: 2'-O-Methyl
<220> FEATURE:
<221> NAME/KEY: misc_feature
<222> LOCATION: (16)..(16)
<223> OTHER INFORMATION: 2'-O-Methyl
<220> FEATURE:
<221> NAME/KEY: misc_feature
<222> LOCATION: (18)..(18)
<223> OTHER INFORMATION: 2'-O-Methyl
<220> FEATURE:
<221> NAME/KEY: misc_feature
<222> LOCATION: (20)..(20)
<223> OTHER INFORMATION: 2'-O-Methyl
<220> FEATURE:
<221> NAME/KEY: misc_feature
<222> LOCATION: (22)..(22)
<223> OTHER INFORMATION: 2'-O-Methyl

<400> SEQUENCE: 12
agacuugagg acuuccugga caa 23

<210> SEQ ID NO 13
<211> LENGTH: 23
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-O-Methyl
<220> FEATURE:
<221> NAME/KEY: misc_feature
<222> LOCATION: (4)..(4)
<223> OTHER INFORMATION: 2'-O-Methyl
<220> FEATURE:
<221> NAME/KEY: misc_feature
<222> LOCATION: (6)..(6)
<223> OTHER INFORMATION: 2'-O-Methyl
<220> FEATURE:
<221> NAME/KEY: misc_feature
<222> LOCATION: (8)..(8)
<223> OTHER INFORMATION: 2'-O-Methyl
<220> FEATURE:
<221> NAME/KEY: misc_feature
<222> LOCATION: (10)..(10)
<223> OTHER INFORMATION: 2'-O-Methyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(14)
<223> OTHER INFORMATION: 2'-O-Methyl
<220> FEATURE:
<221> NAME/KEY: misc_feature
<222> LOCATION: (16)..(16)
<223> OTHER INFORMATION: 2'-O-Methyl
<220> FEATURE:
<221> NAME/KEY: misc_feature
<222> LOCATION: (18)..(18)
<223> OTHER INFORMATION: 2'-O-Methyl
<220> FEATURE:
<221> NAME/KEY: misc_feature
<222> LOCATION: (20)..(20)
<223> OTHER INFORMATION: 2'-O-Methyl
<220> FEATURE:
<221> NAME/KEY: misc_feature
<222> LOCATION: (22)..(22)
<223> OTHER INFORMATION: 2'-O-Methyl

<400> SEQUENCE: 13
agacuugagg acuuccugga caa 23

<210> SEQ ID NO 14
<211> LENGTH: 23
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-Methyl
<220> FEATURE:
<221> NAME/KEY: misc_feature
<222> LOCATION: (3)..(3)
<223> OTHER INFORMATION: 2'-O-Methyl
<220> FEATURE:
<221> NAME/KEY: misc_feature
<222> LOCATION: (5)..(5)
<223> OTHER INFORMATION: 2'-O-Methyl
<220> FEATURE:
<221> NAME/KEY: misc_feature
<222> LOCATION: (7)..(7)
<223> OTHER INFORMATION: 2'-O-Methyl
<220> FEATURE:
<221> NAME/KEY: misc_feature
<222> LOCATION: (9)..(9)
<223> OTHER INFORMATION: 2'-O-Methyl
<220> FEATURE:
<221> NAME/KEY: misc_feature
<222> LOCATION: (11)..(11)
<223> OTHER INFORMATION: 2'-O-Methyl
<220> FEATURE:
<221> NAME/KEY: misc_feature
<222> LOCATION: (13)..(13)
<223> OTHER INFORMATION: 2'-O-Methyl
<220> FEATURE:
<221> NAME/KEY: misc_feature
<222> LOCATION: (15)..(15)
<223> OTHER INFORMATION: 2'-O-Methyl
<220> FEATURE:
<221> NAME/KEY: misc_feature
<222> LOCATION: (17)..(17)
<223> OTHER INFORMATION: 2'-O-Methyl
<220> FEATURE:
<221> NAME/KEY: misc_feature
<222> LOCATION: (19)..(19)
<223> OTHER INFORMATION: 2'-O-Methyl
<220> FEATURE:
<221> NAME/KEY: misc_feature
<222> LOCATION: (21)..(21)
<223> OTHER INFORMATION: 2'-O-Methyl
<220> FEATURE:
<221> NAME/KEY: misc_feature
<222> LOCATION: (23)..(23)
<223> OTHER INFORMATION: 2'-O-Methyl

<400> SEQUENCE: 14
uuguccagga aguccucaag ucu 23

<210> SEQ ID NO 15
<211> LENGTH: 23
<212> TYPE: RNA

<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-O-Methyl
<220> FEATURE:
<221> NAME/KEY: misc_feature
<222> LOCATION: (4)..(4)
<223> OTHER INFORMATION: 2'-O-Methyl
<220> FEATURE:
<221> NAME/KEY: misc_feature
<222> LOCATION: (6)..(6)
<223> OTHER INFORMATION: 2'-O-Methyl
<220> FEATURE:
<221> NAME/KEY: misc_feature
<222> LOCATION: (8)..(8)
<223> OTHER INFORMATION: 2'-O-Methyl
<220> FEATURE:
<221> NAME/KEY: misc_feature
<222> LOCATION: (10)..(10)
<223> OTHER INFORMATION: 2'-O-Methyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(14)
<223> OTHER INFORMATION: 2'-O-Methyl
<220> FEATURE:
<221> NAME/KEY: misc_feature
<222> LOCATION: (16)..(16)
<223> OTHER INFORMATION: 2'-O-Methyl
<220> FEATURE:
<221> NAME/KEY: misc_feature
<222> LOCATION: (18)..(18)
<223> OTHER INFORMATION: 2'-O-Methyl
<220> FEATURE:
<221> NAME/KEY: misc_feature
<222> LOCATION: (20)..(20)
<223> OTHER INFORMATION: 2'-O-Methyl
<220> FEATURE:
<221> NAME/KEY: misc_feature
<222> LOCATION: (22)..(22)
<223> OTHER INFORMATION: 2'-O-Methyl

<400> SEQUENCE: 15
aucacguacg cggaauacuu cga 23

<210> SEQ ID NO 16
<211> LENGTH: 23
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-Methyl
<220> FEATURE:
<221> NAME/KEY: misc_feature
<222> LOCATION: (3)..(3)
<223> OTHER INFORMATION: 2'-O-Methyl
<220> FEATURE:
<221> NAME/KEY: misc_feature
<222> LOCATION: (5)..(5)
<223> OTHER INFORMATION: 2'-O-Methyl
<220> FEATURE:
<221> NAME/KEY: misc_feature
<222> LOCATION: (7)..(7)
<223> OTHER INFORMATION: 2'-O-Methyl
<220> FEATURE:
<221> NAME/KEY: misc_feature
<222> LOCATION: (9)..(9)
<223> OTHER INFORMATION: 2'-O-Methyl

```
<220> FEATURE:
<221> NAME/KEY: misc_feature
<222> LOCATION: (11)..(11)
<223> OTHER INFORMATION: 2'-O-Methyl
<220> FEATURE:
<221> NAME/KEY: misc_feature
<222> LOCATION: (13)..(13)
<223> OTHER INFORMATION: 2'-O-Methyl
<220> FEATURE:
<221> NAME/KEY: misc_feature
<222> LOCATION: (15)..(15)
<223> OTHER INFORMATION: 2'-O-Methyl
<220> FEATURE:
<221> NAME/KEY: misc_feature
<222> LOCATION: (17)..(17)
<223> OTHER INFORMATION: 2'-O-Methyl
<220> FEATURE:
<221> NAME/KEY: misc_feature
<222> LOCATION: (19)..(19)
<223> OTHER INFORMATION: 2'-O-Methyl
<220> FEATURE:
<221> NAME/KEY: misc_feature
<222> LOCATION: (21)..(21)
<223> OTHER INFORMATION: 2'-O-Methyl
<220> FEATURE:
<221> NAME/KEY: misc_feature
<222> LOCATION: (23)..(23)
<223> OTHER INFORMATION: 2'-O-Methyl

<400> SEQUENCE: 16

ucgaaguauu ccgcguacgu gau                                              23


<210> SEQ ID NO 17
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 17

cactttggga aggtcctcct g                                                21


<210> SEQ ID NO 18
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 18

ttcaagggga cagggaaata ctacgcca                                         28


<210> SEQ ID NO 19
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 19

cctcctgctt cttcagtgct tt                                               22
```

<210> SEQ ID NO 20
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 20
ccccgattat gtgagaaaag ga 22

<210> SEQ ID NO 21
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 21
cgacttcctc tgaaatggat ggctcctg 28

<210> SEQ ID NO 22
<211> LENGTH: 23
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 22
cgctcttggt gctgtagatt ttg 23

<210> SEQ ID NO 23
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 23
tctgcctacc tcacctgttt cc 22

<210> SEQ ID NO 24
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 24
atggaggagg aggaagtatg tgacccca 28

<210> SEQ ID NO 25
<211> LENGTH: 23
<212> TYPE: DNA
<213> ORGANISM: Artificial

-continued

```
<220> FEATURE:
<223> OTHER INFORMATION: Synthetic
<220> FEATURE:
<221> NAME/KEY: misc_feature
<223> OTHER INFORMATION: Primer/Probe

<400> SEQUENCE: 25

tgactgattc ctgctgtgtt gtc                                        23
```